(12) United States Patent
Miller et al.

(10) Patent No.: US 9,955,946 B2
(45) Date of Patent: May 1, 2018

(54) CAROTID BODY ABLATION WITH A TRANSVENOUS ULTRASOUND IMAGING AND ABLATION CATHETER

(71) Applicant: CIBIEM, INC., Los Altos, CA (US)

(72) Inventors: Jason Michael Miller, Los Altos, CA (US); Yegor D. Sinelnikov, Port Jefferson, NY (US); Zoar Jacob Engelman, Salt Lake City, UT (US); Martin M. Grasse, San Francisco, CA (US); Michael Brick Markham, Redwood City, CA (US); Veijo T. Suorsa, Sunnyvale, CA (US); Miriam H. Taimisto, San Jose, CA (US)

(73) Assignee: Cibiem, Inc., Los Altos, CA (US)

( * ) Notice: Subject to any disclaimer, the term of this patent is extended or adjusted under 35 U.S.C. 154(b) by 177 days.

(21) Appl. No.: 14/656,635

(22) Filed: Mar. 12, 2015

(65) Prior Publication Data

US 2015/0257779 A1    Sep. 17, 2015

Related U.S. Application Data

(60) Provisional application No. 61/952,015, filed on Mar. 12, 2014, provisional application No. 62/017,148, (Continued)

(51) Int. Cl.
*A61B 8/00* (2006.01)
*A61B 8/12* (2006.01)
(Continued)

(52) U.S. Cl.
CPC .............. *A61B 8/12* (2013.01); *A61B 8/0841* (2013.01); *A61B 8/0891* (2013.01); *A61N 7/022* (2013.01);
(Continued)

(58) Field of Classification Search
CPC ....... A61B 8/12; A61B 8/0841; A61B 8/0891; A61B 2090/3925; A61B 2090/378;
(Continued)

(56) References Cited

U.S. PATENT DOCUMENTS 3,650,277 A   3/1972  Sjostrand et al.
4,011,872 A   3/1977  Komiya
(Continued)

FOREIGN PATENT DOCUMENTS

AU   2015292550 A1   1/2016
CN      1440256 A    9/2003
(Continued)

OTHER PUBLICATIONS

Sinelnikov et al.; U.S. Appl. No. 15/069,531 entitled "Carotid septum ablation with ultrasound imaging and ablation catheters," filed Mar. 14, 2016.
(Continued)

*Primary Examiner* — Sanjay Cattungal
(74) *Attorney, Agent, or Firm* — Shay Glenn LLP

(57) ABSTRACT

Methods and devices for assessing, and treating patients having sympathetically mediated disease, involving augmented peripheral chemoreflex and heightened sympathetic tone by reducing chemosensor input to the nervous system via carotid body ablation.

24 Claims, 42 Drawing Sheets

Related U.S. Application Data filed on Jun. 25, 2014, provisional application No. 62/049,980, filed on Sep. 12, 2014.

(51) Int. Cl.
*A61B 8/08* (2006.01)
*A61N 7/02* (2006.01)
*A61B 18/00* (2006.01)
*A61B 90/00* (2016.01)

(52) U.S. Cl.
CPC ............ *A61B 8/445* (2013.01); *A61B 8/4477* (2013.01); *A61B 8/481* (2013.01); *A61B 8/488* (2013.01); *A61B 2018/00023* (2013.01); *A61B 2018/00029* (2013.01); *A61B 2090/0472* (2016.02); *A61B 2090/378* (2016.02); *A61B 2090/3782* (2016.02); *A61B 2090/3784* (2016.02); *A61B 2090/3925* (2016.02); *A61B 2090/3983* (2016.02)

(58) Field of Classification Search
CPC .... A61B 2090/3784; A61B 2090/3983; A61B 2090/0472; A61B 2090/3782; A61B 2018/00029; A61B 2018/00023; A61B 8/488; A61B 8/4477; A61B 8/445; A61N 7/022
USPC .................................. 600/437–469
See application file for complete search history.

(56) References Cited

U.S. PATENT DOCUMENTS

| | | | |
|---|---|---|---|
| 4,201,219 A | 5/1980 | Bozal | |
| 4,791,931 A | 12/1988 | Slate | |
| 4,960,133 A | 10/1990 | Hewson | |
| 5,125,928 A | 6/1992 | Parins | |
| 5,139,496 A | 8/1992 | Hed et al. | |
| 5,147,294 A | 9/1992 | Smith et al. | |
| 5,325,860 A | 7/1994 | Seward et al. | |
| 5,334,193 A | 8/1994 | Nardella | |
| 5,345,940 A | 9/1994 | Seward et al. | |
| 5,348,555 A | 9/1994 | Zinnanti | |
| 5,354,271 A | 10/1994 | Voda | |
| 5,431,621 A | 7/1995 | Dory | |
| 5,435,311 A | 7/1995 | Umemura et al. | |
| 5,476,495 A | 12/1995 | Kordis et al. | |
| 5,492,126 A | 2/1996 | Hennige et al. | |
| 5,500,012 A | 3/1996 | Brucker et al. | |
| 5,588,432 A | 12/1996 | Crowley | |
| 5,722,411 A | 3/1998 | Suzuki et al. | |
| 5,735,280 A | 4/1998 | Sherman et al. | |
| 5,800,486 A | 9/1998 | Thome et al. | |
| 5,817,021 A | 10/1998 | Reichenberger | |
| 5,826,588 A | 10/1998 | Forman | |
| 5,879,295 A | 3/1999 | Li et al. | |
| 5,893,863 A | 4/1999 | Yoon | |
| 5,906,580 A | 5/1999 | Kline-Schoder et al. | |
| 5,916,213 A | 6/1999 | Haissaguerre et al. | |
| 5,919,187 A | 7/1999 | Guglielmi et al. | |
| 5,957,882 A | 9/1999 | Nita et al. | |
| 6,004,269 A | 12/1999 | Crowley et al. | |
| 6,068,629 A | 5/2000 | Haissaguerre et al. | |
| 6,071,279 A | 6/2000 | Whayne et al. | |
| 6,071,281 A | 6/2000 | Burnside et al. | |
| 6,125,857 A | 10/2000 | Silber | |
| 6,129,359 A | 10/2000 | Haas et al. | |
| 6,182,666 B1 | 2/2001 | Dobak, III | |
| 6,217,576 B1 | 4/2001 | Tu et al. | |
| 6,228,082 B1 | 5/2001 | Baker et al. | |
| 6,235,024 B1 | 5/2001 | Tu | |
| 6,306,133 B1 | 10/2001 | Tu et al. | |
| 6,355,029 B1 | 3/2002 | Joye et al. | |
| 6,379,348 B1 | 4/2002 | Onik | |
| 6,402,746 B1 | 6/2002 | Whayne et al. | |
| 6,411,852 B1 | 6/2002 | Danek et al. | |
| 6,425,867 B1 | 7/2002 | Vaezy et al. | |
| 6,454,713 B1 | 9/2002 | Ishibashi et al. | |
| 6,478,793 B1* | 11/2002 | Cosman ............ | A61B 18/1477 128/898 |
| 6,497,705 B2 | 12/2002 | Comben | |
| 6,522,926 B1 | 2/2003 | Kieval et al. | |
| 6,533,726 B1 | 3/2003 | Lizzi et al. | |
| 6,533,784 B2 | 3/2003 | Truckai et al. | |
| 6,544,187 B2 | 4/2003 | Seward | |
| 6,556,695 B1 | 4/2003 | Packer et al. | |
| 6,656,136 B1 | 12/2003 | Weng et al. | |
| 6,660,013 B2 | 12/2003 | Rabiner et al. | |
| 6,673,066 B2 | 1/2004 | Werneth | |
| 6,776,763 B2 | 8/2004 | Nix et al. | |
| 6,802,843 B2 | 10/2004 | Truckai et al. | |
| 6,905,497 B2 | 6/2005 | Truckai et al. | |
| 6,937,903 B2 | 8/2005 | Schuler et al. | |
| 7,097,641 B1 | 8/2006 | Arless et al. | |
| 7,137,963 B2 | 11/2006 | Nita et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,185,656 B2 | 3/2007 | Wakhloo et al. | |
| 7,207,989 B2 | 4/2007 | Pike et al. | |
| 7,363,076 B2 | 4/2008 | Yun et al. | |
| 7,617,005 B2 | 11/2009 | Demarais et al. | |
| 7,628,785 B2 | 12/2009 | Hadjicostis et al. | |
| 7,736,317 B2 | 6/2010 | Stephens et al. | |
| 7,736,360 B2 | 6/2010 | Mody et al. | |
| 7,738,952 B2 | 6/2010 | Yun et al. | |
| 7,766,961 B2 | 8/2010 | Patel et al. | |
| 7,853,333 B2 | 12/2010 | Demarais | |
| 7,901,450 B2 | 3/2011 | Johnson et al. | |
| 7,922,663 B2 | 4/2011 | Tran et al. | |
| 7,925,352 B2 | 4/2011 | Stack et al. | |
| 7,959,628 B2 | 6/2011 | Scheer et al. | |
| 8,002,728 B2 | 8/2011 | Chang | |
| 8,060,206 B2 | 11/2011 | Kieval et al. | |
| 8,075,554 B2 | 12/2011 | Malecki et al. | |
| 8,116,883 B2 | 2/2012 | Williams et al. | |
| 8,157,760 B2 | 4/2012 | Criado et al. | |
| 8,167,805 B2 | 5/2012 | Emery et al. | |
| 8,192,425 B2 | 6/2012 | Mirza et al. | |
| 8,192,760 B2 | 6/2012 | Hossainy et al. | |
| 8,292,879 B2 | 10/2012 | Manwaring et al. | |
| 8,295,912 B2 | 10/2012 | Gertner | |
| 8,308,709 B2 | 11/2012 | Chang | |
| 8,326,429 B2 | 12/2012 | Wenzel et al. | |
| 8,364,237 B2 | 1/2013 | Stone et al. | |
| 8,374,674 B2 | 2/2013 | Gertner | |
| 8,396,548 B2 | 3/2013 | Perry et al. | |
| 8,409,200 B2 | 4/2013 | Holcomb et al. | |
| 8,433,423 B2 | 4/2013 | Demarais | |
| 8,465,752 B2 | 6/2013 | Seward | |
| 8,469,904 B2 | 6/2013 | Gertner | |
| 8,568,399 B2 | 10/2013 | Azamian et al. | |
| 8,620,423 B2 | 12/2013 | Demarais et al. | |
| 9,060,784 B2 | 6/2015 | Coe et al. | |
| 9,089,541 B2 | 7/2015 | Azamian | |
| 9,259,271 B2* | 2/2016 | Anvari ............ | A61B 10/0266 |
| 2001/0027333 A1 | 10/2001 | Schwartz | |
| 2001/0041890 A1 | 11/2001 | Hassett et al. | |
| 2002/0002372 A1 | 4/2002 | Jahns et al. | |
| 2002/0087151 A1 | 7/2002 | Mody et al. | |
| 2002/0128639 A1 | 9/2002 | Pless et al. | |
| 2003/0009125 A1 | 1/2003 | Nita et al. | |
| 2003/0153907 A1 | 8/2003 | Suorsa et al. | |
| 2004/0054347 A1 | 3/2004 | Zadno Azizi et al. | |
| 2004/0116921 A1 | 6/2004 | Sherman et al. | |
| 2004/0176788 A1 | 9/2004 | Opolski | |
| 2004/0179788 A1 | 9/2004 | Fleenor et al. | |
| 2004/0210214 A1 | 10/2004 | Knowlton | |
| 2004/0210239 A1 | 10/2004 | Nash et al. | |
| 2005/0096642 A1 | 5/2005 | Appling et al. | |
| 2005/0096710 A1 | 5/2005 | Kieval | |
| 2005/0143378 A1 | 6/2005 | Yun et al. | |
| 2005/0153885 A1 | 7/2005 | Yun et al. | |
| 2005/0245894 A1 | 11/2005 | Zadno Azizi | |

(56) References Cited

U.S. PATENT DOCUMENTS

| | | |
|---|---|---|
| 2005/0251122 A1 | 11/2005 | Swanson |
| 2005/0288656 A1 | 12/2005 | Koerner |
| 2005/0288730 A1 | 12/2005 | Deem et al. |
| 2006/0025756 A1 | 2/2006 | Francischelli et al. |
| 2006/0064137 A1 | 3/2006 | Stone |
| 2006/0069385 A1 | 3/2006 | Lafontaine et al. |
| 2006/0111754 A1 | 5/2006 | Rezai et al. |
| 2006/0135962 A1 | 6/2006 | Kick et al. |
| 2006/0165667 A1 | 7/2006 | Laughlin et al. |
| 2006/0178621 A1 | 8/2006 | Constantz et al. |
| 2006/0195149 A1 | 8/2006 | Hopper et al. |
| 2006/0224110 A1 | 10/2006 | Scott et al. |
| 2006/0253161 A1 | 11/2006 | Libbus et al. |
| 2006/0259084 A1 | 11/2006 | Zhang et al. |
| 2006/0282131 A1 | 12/2006 | Caparso et al. |
| 2006/0287679 A1 | 12/2006 | Stone |
| 2007/0015006 A1 | 1/2007 | Lee et al. |
| 2007/0073135 A1 | 3/2007 | Lee et al. |
| 2007/0112327 A1 | 5/2007 | Yun et al. |
| 2007/0129633 A1 | 6/2007 | Lee et al. |
| 2007/0135875 A1 | 6/2007 | Demarais et al. |
| 2007/0142879 A1 | 6/2007 | Greenberg et al. |
| 2007/0150006 A1 | 6/2007 | Libbus et al. |
| 2007/0156179 A1 | 7/2007 | Karashurov |
| 2007/0208388 A1 | 9/2007 | Jahns et al. |
| 2007/0265609 A1 | 11/2007 | Thapliyal et al. |
| 2007/0299476 A1 | 12/2007 | Park et al. |
| 2008/0009916 A1 | 1/2008 | Rossing et al. |
| 2008/0009917 A1 | 1/2008 | Rossing et al. |
| 2008/0027346 A1 | 1/2008 | Litt et al. |
| 2008/0039727 A1 | 2/2008 | Babaev |
| 2008/0045936 A1 | 2/2008 | Vaska et al. |
| 2008/0058871 A1 | 3/2008 | Libbus et al. |
| 2008/0086181 A1 | 4/2008 | Amurthur et al. |
| 2008/0294158 A1 | 11/2008 | Pappone et al. |
| 2009/0043186 A1 | 2/2009 | Jung et al. |
| 2009/0131798 A1 | 5/2009 | Minar et al. |
| 2009/0299362 A1 | 12/2009 | Long et al. |
| 2010/0049031 A1 | 2/2010 | Fruland et al. |
| 2010/0063564 A1 | 3/2010 | Libbus et al. |
| 2010/0070004 A1 | 3/2010 | Hlavka |
| 2010/0100181 A1 | 4/2010 | Makower et al. |
| 2010/0152590 A1 | 6/2010 | Moore et al. |
| 2010/0160781 A1 | 6/2010 | Carter et al. |
| 2010/0168731 A1 | 7/2010 | Wu et al. |
| 2010/0168739 A1 | 7/2010 | Wu et al. |
| 2010/0179424 A1 | 7/2010 | Warnking et al. |
| 2010/0217151 A1 | 8/2010 | Gostout et al. |
| 2010/0262013 A1 | 10/2010 | Smith et al. |
| 2010/0268307 A1 | 10/2010 | Demarais et al. |
| 2010/0274219 A1 | 10/2010 | Wenzel et al. |
| 2011/0009854 A1 | 1/2011 | Babkin et al. |
| 2011/0040297 A1 | 2/2011 | Babkin et al. |
| 2011/0066085 A1 | 3/2011 | Weng et al. |
| 2011/0098699 A1 | 4/2011 | Pachon et al. |
| 2011/0104060 A1 | 5/2011 | Seward |
| 2011/0112400 A1 | 5/2011 | Emery et al. |
| 2011/0118598 A1 | 5/2011 | Gertner |
| 2011/0118600 A1 | 5/2011 | Gertner |
| 2011/0130708 A1 | 6/2011 | Perry et al. |
| 2011/0144631 A1 | 6/2011 | Elkins et al. |
| 2011/0172529 A1 | 7/2011 | Gertner |
| 2011/0190662 A1* | 8/2011 | McWeeney ............ A61B 10/04 600/567 |
| 2011/0208096 A1 | 8/2011 | Demarais et al. |
| 2011/0208174 A1 | 8/2011 | Baust |
| 2011/0208175 A1 | 8/2011 | Sobotka et al. |
| 2011/0224667 A1 | 9/2011 | Koblish et al. |
| 2011/0251487 A1 | 10/2011 | Magnin et al. |
| 2011/0251607 A1 | 10/2011 | Kruecker et al. |
| 2011/0257561 A1 | 10/2011 | Gertner et al. |
| 2011/0257562 A1 | 10/2011 | Schaer |
| 2011/0301587 A1 | 12/2011 | Deem et al. |
| 2012/0016226 A1 | 1/2012 | Gertner |
| 2012/0059437 A1 | 3/2012 | Shalev |
| 2012/0065492 A1 | 3/2012 | Gertner et al. |
| 2012/0065494 A1 | 3/2012 | Gertner et al. |
| 2012/0065554 A1 | 3/2012 | Pikus |
| 2012/0078248 A1 | 3/2012 | Worrell et al. |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0095461 A1 | 4/2012 | Herscher et al. |
| 2012/0101018 A1 | 4/2012 | Miracle et al. |
| 2012/0109018 A1 | 5/2012 | Gertner et al. |
| 2012/0130368 A1 | 5/2012 | Jenson |
| 2012/0157992 A1 | 6/2012 | Smith et al. |
| 2012/0157993 A1 | 6/2012 | Jenson et al. |
| 2012/0172680 A1 | 7/2012 | Gelfand et al. |
| 2012/0172723 A1 | 7/2012 | Gertner |
| 2012/0184952 A1 | 7/2012 | Jenson et al. |
| 2012/0199616 A1 | 8/2012 | Lamb et al. |
| 2012/0232436 A1 | 9/2012 | Warnking |
| 2012/0238918 A1 | 9/2012 | Gertner |
| 2012/0245494 A1 | 9/2012 | Gertner |
| 2012/0265227 A1 | 10/2012 | Sverdlik et al. |
| 2012/0277763 A1 | 11/2012 | Greenblatt et al. |
| 2012/0302877 A1 | 11/2012 | Harks et al. |
| 2013/0006228 A1 | 1/2013 | Johnson et al. |
| 2013/0066316 A1 | 3/2013 | Steinke et al. |
| 2013/0123625 A1 | 5/2013 | Hastings et al. |
| 2013/0123778 A1 | 5/2013 | Richardson et al. |
| 2013/0131668 A1 | 5/2013 | Schaer |
| 2013/0137980 A1 | 5/2013 | Waters et al. |
| 2013/0197555 A1 | 8/2013 | Schaer |
| 2013/0197614 A1 | 8/2013 | Gustus et al. |
| 2013/0199019 A1 | 8/2013 | Garbini et al. |
| 2013/0303876 A1* | 11/2013 | Gelfand ............... A61B 18/12 600/407 |
| 2013/0310823 A1 | 11/2013 | Gelfand et al. |
| 2013/0324987 A1 | 12/2013 | Leung et al. |
| 2013/0324989 A1* | 12/2013 | Leung ................... A61B 18/02 606/24 |
| 2014/0005706 A1 | 1/2014 | Gelfand et al. |
| 2014/0018788 A1 | 1/2014 | Engelman et al. |
| 2014/0039450 A1 | 2/2014 | Green et al. |
| 2014/0135661 A1 | 5/2014 | Garrison et al. |
| 2014/0180034 A1 | 6/2014 | Hoseit et al. |
| 2014/0180273 A1 | 6/2014 | Nair |
| 2014/0243809 A1 | 8/2014 | Gelfand et al. |
| 2014/0249423 A1 | 9/2014 | Cai et al. |
| 2014/0276771 A1 | 9/2014 | Miller et al. |
| 2014/0288015 A1 | 9/2014 | Venkateswara-Rao et al. |
| 2014/0350401 A1 | 11/2014 | Sinelnikov |
| 2015/0018725 A1 | 1/2015 | Sommer et al. |
| 2015/0045675 A1 | 2/2015 | Chernomorsky |
| 2015/0202444 A1 | 7/2015 | Franke et al. |
| 2015/0289929 A1 | 10/2015 | Toth et al. |
| 2016/0000499 A1 | 1/2016 | Lennox et al. |
| 2016/0199127 A1 | 7/2016 | Prutchi |
| 2016/0338753 A1 | 11/2016 | Ryba et al. |
| 2016/0374710 A1 | 12/2016 | Sinelnikov et al. |
| 2016/0375241 A1 | 12/2016 | Hlavka et al. |

FOREIGN PATENT DOCUMENTS

| | | |
|---|---|---|
| CN | 1905841 A | 1/2007 |
| CN | 101027097 A | 8/2007 |
| DE | 10151797 A1 | 5/2003 |
| EP | 0472368 A2 | 2/1992 |
| EP | 0819014 B1 | 2/2003 |
| EP | 2008600 A2 | 12/2008 |
| EP | 2488250 A | 8/2012 |
| EP | 1299035 B1 | 2/2013 |
| EP | 2783651 A1 | 10/2014 |
| EP | 2635348 B1 | 3/2016 |
| WO | WO97/25916 A1 | 7/1997 |
| WO | WO98/43701 A1 | 10/1998 |
| WO | WO00/25685 A1 | 5/2000 |
| WO | WO01/64123 A2 | 9/2001 |
| WO | WO02/069862 A1 | 9/2002 |
| WO | WO03/076008 A1 | 9/2003 |
| WO | WO2004/086936 A2 | 10/2004 |
| WO | WO2004/105807 A2 | 12/2004 |

(56) References Cited

FOREIGN PATENT DOCUMENTS

| | | |
|---|---|---|
| WO | WO2005/065563 A1 | 7/2005 |
| WO | WO2007/092330 A1 | 8/2007 |
| WO | WO2007/146834 A2 | 12/2007 |
| WO | WO2008/025855 A2 | 3/2008 |
| WO | WO2009/120953 A2 | 10/2009 |
| WO | WO2010/093603 A1 | 8/2010 |
| WO | WO2010/121738 A1 | 10/2010 |
| WO | WO2010/124120 A1 | 10/2010 |
| WO | WO2010/132703 A1 | 11/2010 |
| WO | WO2011/082278 A1 | 7/2011 |
| WO | WO2011/130531 A2 | 10/2011 |
| WO | WO2012/015720 A1 | 2/2012 |
| WO | WO2012/015721 A1 | 2/2012 |
| WO | WO2012/015722 A1 | 2/2012 |
| WO | WO2012/016135 A1 | 2/2012 |
| WO | WO2012/057916 A1 | 5/2012 |
| WO | WO2012/112165 A1 | 8/2012 |
| WO | WO2012/125172 A1 | 9/2012 |
| WO | WO2013/018083 A2 | 2/2013 |
| WO | WO2013/074813 A1 | 5/2013 |
| WO | WO2013/157011 A2 | 10/2013 |
| WO | WO2015/021304 A2 | 2/2015 |
| WO | WO2015/022668 A2 | 2/2015 |
| WO | WO2015/103539 A1 | 7/2015 |

OTHER PUBLICATIONS

Martin et al.; U.S. Appl. No. 15/105,599 entitled "Methods, devices and systems for carotid body ablation via a transradial or transbrachial approach," filed Jun. 17, 2016.
Gelfand et al.; U.S. Appl. No. 15/214,222 entitled "Endovascular catheters and methods for carotid body ablation," filed Jul. 19, 2016.
Abboud, F.; In search of autonomic balance: the good, the bad, and the ugly; Am J Physiol Regul Integr Comp Physiol; 298; pp. R1449-R1467; Jun. 2010.
Abdala et al; Hypertension is critically dependent on the carotid body input in the spontaneously hypertensive rat; J Physiol; 590(17); pp. 4269-4277; Sep. 2012.
Abdala et al; Peripheral chemoreceptor inputs contribute to the development of high blood pressure in spontaneously hypertensive rats(proceeding abstract); Proc Physiol Soc 23; PC22; Oxford, England; Jul. 2011 (printed Sep. 24, 2013 from: http://www.physoc.org/proceedings/abstract/Proc%20Physiol%20Soc%2023PC22).
Al-Rawi et al.; Effect of lignocaine injection in carotid sinus on baroreceptor sensitivity during carotid endarterectomy; J Vasc Surg; 39(6); pp. 1288-1294; Jun. 2004.
Anand et al.; Management of the internal carotid artery during carotid body tumor surgery; Laryngoscope; 105; pp. 231-235; Mar. 1995.
Anderson et al. (executive committee); Carotid body resection; J. Allergy Clin. Immunol.; 78(2); pp. 273-275; Aug. 1986.
Arena et al.; Prognostic value of resting end-tidal carbon dioxide in patients with heart failure; Int J Cardiol; 109(3); pp. 351-358; May 2006.
Banzett et al.; Dyspnea and pain: similarities and contrasts between two very unpleasant sensations; APS Bulletin; 11(1); 6 pgs.; Mar./Apr. 2001.
Bencini et al.; The carotid bodies in bronchial asthma; Histopathology; 18; pp. 195-200; Mar. 1991.
Bencini, A.; Reduction of reflex bronchotropic impulses as a result of carotid body surgery; International Surgery; 54(6); pp. 415-423; Dec. 1970.
Bernstein et al.; Current status of glomectomy; (The Amer. Acad. of Allergy, Abstracts of papers given at Ann. Meeting, Feb. 3-7, 1978, Boston MA; J. Allergy; 41(2); pp. 88-89; Feb. 1968.
Bishop, Jr. et al.; Paragangliomas of the neck; Arch Surg.; 127; pp. 1441-1445; Dec. 1992.
Braunwald et al.; Carotid sinus nerve stimulation for the treatment of intractable angina pectoris: surgical technic; Annals of Surgery; 172(5); pp. 870-876; Nov. 1970.

Braunwald et al.; Carotid sinus nerve stimulation in the treatment of angina pectoris and supraventricular tachycardia; The Western Journal of Medicine; 112(3); pp. 41-50; Mar. 1970.
Capps et al.; The late effects of bilateral carotid sinus denervation in man; J Clin Invest; 17(4); pp. 385-389; Jul. 1938.
Chang et al.; Impaired response to hypoxia after bilateral carotid body resection for treatment of bronchial asthma; Chest; 73; pp. 667-669; May 1978.
Curran et al.; Glomectomy for severe bronchial asthma. A double-blind study; Am Rev Respir Dis; 93(1); pp. 84-89; Jan. 1966.
Davidson et al.; Role of the carotid bodies in breath-holding; N Engl J Med; 290(15); pp. 819-822; Apr. 1974.
de Weerd et al.; Prevalence of asymptomatic carotid artery stenosis according to age and sex: Systematic review and metaregression analysis; Stroke; 40(4); pp. 1105-1113; Apr. 2009.
Dickinson et al.; Carotid body tumour: 30 years experience; Br. J. Surg.; 73(1); pp. 14-16; Jan. 1986.
Ding et al.; Role of blood flow in carotid body chemoreflex function in heart failure; J Physiol; 589(1); pp. 245-258; Jan. 2011.
Doumas et al.; Benefits from treatment and control of patients with resistant hypertension; Int. J Hypertension; 8 pgs; Dec. 2011.
Fletcher, Jr. et al.; The surgical treatment of bronchial asthma by excision of the carotid body; J Christ Med Assoc India; 38; pp. 492-496; Sep. 1963.
Gain et al.; Anaesthesia for glomectomy in the asthmatic patient; Can Aneas Soc J; 11(4); pp. 417-424; Jul. 1964.
Giannoni et al.; Combined increased chemosensitiviy to hypoxia and hypercapnia as a prognosticator in heart failure; JACC; 53(21); pp. 1975-1980; May 2009.
Giannoni et al.; Clinical significance of chemosensitivity in chronic heart failure: influence on neurohormonal derangement, cheyne-strokes respiration and arrhythmias; Clinical Science (London); 114(7); pp. 489-497; Apr. 2008.
Grassi, G.; Renal denervation in cardiometabolic disease: Concepts, achievements and perspectives; Nutr Metab Cardiovasc Dis; 23(2); pp. 77-83; Feb. 2013 (Epub Nov. 10, 2012).
Green, M.; Observations on glomectomized asthmatic patients; Annals of Allergy; 23(5); pp. 213-219; May 1965.
Gudovsky et al.; Surgical treatment of bronchial asthma (with translation); Khirurgiia; 7; pp. 14-18; 2002 (year of pub. sufficiently earlier than effective US filed and any foreign priority date).
Guz et al.; Peripheral chemoreceptor block in man; Respiration Physiology; 1; pp. 38-40; 1966 (year of pub. sufficiently earlier than effective US filed and any foreign priority date).
Gwon et al.; Risk factors for stroke during surgery for carotid body tumors; World J Surg; 35(9); pp. 2154-2158; Sep. 2011.
Handelsman, H.; Bilateral carotid body resection as a treatment for chronic intractable bronchospastic diseases; Health Technology Assessment Series: Health Technology Assessment Report; No. 12; 13 pgs.; 1985 (year of pub. sufficiently earlier than effective US filed and any foreign priority date).
Hickey et al.; Bilateral carotid endarterectomy with attempted preservation of the carotid body function; Ann. Surg.; 175(2); pp. 268-273; Feb. 1972.
Honda et al.; Hypoxic chemosensitivity in asthmatic patients two decades after carotid body resection; J Appl Physiol.; 46(4); pp. 632-638; Apr. 1979.
Honda, Y.; Respiratory and circulatory activities in carotid body-resected humans; J Appl Physiol; 73(1); pp. 1-8; Jul. 1992.
Karashurov et al.; Radiofrequency electrostimulation of synocarotid for the treatment of bronchial asthma (with translation); Khirurgiia (Mosk); 12; pp. 4-6; 1999 (year of pub. sufficiently earlier than effective US filed and any foreign priority date).
Keim, W. F.; Carotid glomectomy in bronchial asthma; Archives of Otolaryngology; 79; pp. 225-228; Mar. 1964.
Kim et al.; Carotid artery-hypoglossal nerve relationships in the neck: an anatomical work; Neurol Res; 31; pp. 895-899; Nov. 2009.
Kline et al.; Cervical glomectomy for bronchial asthma; Journal of the Medical Society of New Jersey; 61(5); pp. 176-178; May 1964.
Leggate, J. M.; Treatment of asthma by excision of the carotid body; Postgraduate Med. Journal; 26(292)pp. 71-77; Feb. 1950.

(56) References Cited

OTHER PUBLICATIONS

Lesske et al.; Hypertension caused by chronic intermittent hypoxia—influence of chemoreceptors and sympathetic nervous system; J Hypertens; 15(12); pp. 1593-1603; Dec. 1997.
Lo et al.; Anatomical variations of the common carotid artery bifurcation; Anz J. Surg.; 76(11); pp. 970-972; Nov. 2006.
Lugliani et al.; A role for the carotid body in cardiovascular control in man; Chest; 63(5); pp. 744-750; May 1973.
Lugliani et al.; Effect of bilateral carotid-body resection on ventilatory control at rest and during exercise in man; New England J Med; 285(20); pp. 1105-1111; Nov. 1971.
Lusiani et al.; Prevalence of atherosclerotic involvement of the internal carotid artery in hypertensive patients; Int J Cardiol; 17; pp. 51-56; Oct. 1987.
Lyons et al.; Anatomical variants of the cervical sympathetic chain to be considered during neck dissection; Br J Oral Maxillofac Surg; 36(3); pp. 180-182; Jun. 1998.
Ma et al.; A retrospective study in management of carotid body tumour; Br J Oral Maxillofac Surg; 47(6); pp. 461-465; Sep. 2009.
MacGowan, W.; Removal of the carotid body for asthma: A report of 19 treated patients; Dis Chest; 51(3); pp. 278-281; Mar. 1967.
Marschke et al.; Carotid-body removal in asthma; JAMA; 191(5); p. 397; Feb. 1965.
Marshall, J.; Peripheral chemoreceptors and cardiovascular regulation; Physiological Reviews; 74(3); pp. 543-594; Jul. 1994.
Meyerson, Sheldon; A histological study of the morphology of the cervical carotid bifurcation, including descriptions of intramural neural elements (Thesis); Ohio State University; 47 pgs.; 1968 (year of pub. sufficiently earlier than effective US filed and any foreign priority date).
Myers et al.; End-tidal CO2 pressure and cardiac performance during exercise in heart failure; Med Sci Sports Exerc; 41(1); pp. 18-24; Jan. 2009.
Nadel et al.; Effect of changes in blood gas tensions and carotid sinus pressure on tracheal volume and total lung resistance to airflow; J Physiol; 163(1); pp. 13-33; Aug. 1962.
Nakayama, K.; Surgical removal of the carotid body for bronchial asthma; Chest; 40(6); pp. 595-604; Dec. 1961.
Nakayama, K.; Surgical removal of the carotid body for bronchial asthma; The Australian and the New Zealand Journal of Surgery; 31(3); pp. 214-221; Feb. 1962.
Nakayama, K.; The surgical significance of the carotid body in relation to bronchial asthma; Thoracic Surgery; Journal of the International College of Surgeons; 39(4); pp. 374-389; Apr. 1963.
Nespoulet et al.; Altitude illness is related to low hypoxic chemoresponse and low oxygenation during sleep; Eur Respir J; 40(3); pp. 673-80; Sep. 2012 (ERJ Express; epub Apr. 20, 2012).
Nguyen et al.; Carotid body detection on CT angiography; Am J Neuroradiol; 32; pp. 1096-1099; Jun.-Jul. 2011.
O'Donnell et al.; Pathophysiology of dyspnea in chronic obstructive pulmonary disease: a rountable; Proc Am Thorac Soc; 4(2); pp. 145-168; May 2007.
O'Rourke et al.; Removal of the carotid body for asthma: a preliminary report of 40 cases; The Medical Journal of Australia; 2; pp. 1040-1043; Dec. 1963.
O'Rourke et al.; Removal of the carotid body for asthma: an appraisal of results; The Medical Journal of Australia; 2; pp. 869-870; Nov. 1964.
Overholt et al.; Hidden or unsuspected brochiectasis in the asthmatic patient; JAMA; 150(5); pp. 438-441; Oct. 1952.
Overholt, R.; Glomectomy for asthma; Chest; 40; pp. 605-610; Dec. 1961.
Paliwoda et al.; Surgical removal of the carotid body and denervation of the carotid sinus for bronchial asthma; East African Medical Journal; 44(7); pp. 285-287; Jul. 1967.
Paton et al.; The carotid body as a therapeutic target for the treatment of sympathetically mediated diseases; Hypertension; 61; pp. 5-13; Jan. 2013.
Pennes; Analysis of tissue and arterial blood temperatures in the resting human forearm; J. Appl. Physiol.; 1(2); pp. 93-122; Aug. 1948.
Perret et al.; High prevalence of peripheral atherosclerosis in a rapidly developing country; Atherosclerosis; 153(1); pp. 9-21; Nov. 2000.
Phillips et al.; Results of glomectomy in chronic obstructive pulmonary disease: A four year follow-up report of 57 cases; Chest; 58(4); pp. 358-362; Oct. 1970.
Phillips, J.; Removal of the carotid body for asthma and emphysema; Southern Medical Journal; 57; pp. 1278-1281; Nov. 1964.
Phillips, J.; Treatment of obstructive bronchial diseases; Geriatrics; 21(7); pp. 137-143; Jul. 1966.
Ponikowski et al.; Peripheral chemoreceptor hypersensitivity; Circulation; 101; pp. 544-549; Jul. 2001.
Rabl et al.; Diagnosis and treatment of carotid body tumors; Thorac Cardiovasc Surg.; 41(6); pp. 340-343; Dec. 1993.
Sanghvi et al.; Carotid body tumors; Journal of Surgical Oncology; 54(3); pp. 190-192; Nov. 1993.
Sapareto et al.; Thermal dose determination in cancer therapy; Int. J. Radiat. Biol. Phys.; 10(6); pp. 787-800; Jun. 1984.
Sedwitz et al.; Should the carotid body be removed in the treatment of asthma and emphysema?; International Surgery; 57(6); pp. 467-469; Jun. 1972.
Sedwitz et al.; Unilateral excision of the carotid body in the treatment of 500 asthma patients; Vascular Diseases; 2; pp. 91-98; Mar. 1965.
Sedwitz, J.; Unilateral carotid body resectin for asthma; Jounal of the National Medical Association; 55(5); pp. 384-388; Sep. 1963.
Segal et al.; Glomectomy in the treatment of chronic bronchial asthma; NEJM; 272(2); pp. 57-63; Jan. 1965.
Segal, M.; Glomectomy for chronic bronchial asthma: A three phase study; Annals of Allergy; 23; pp. 377-384; Aug. 1965.
Severinghaus, J.; Carotid body resection for COPD?; CHEST; 95(5); pp. 1128-1129; May 1989.
Shalev, Alon; U.S. Appl. No. 61/178,049 entitled "Endovascular systems for performing interventions during ischemic conditions of the CNS by utilizing the carotid baroreceptors and chemoreceptors and methods for using same," filed May 14, 2009.
Shamblin et al.; Carotid Body Tumor; Am J Surg; 122; pp. 732-739; Dec. 1971.
Shek, J.; Excision of carotid body for advanced emphysema; Michigan State Medical Society Journal; 63; pp. 211-212; Mar. 1964.
Silva et al.; Welcome the carotid chemoreflex to the 'neural control of the circulation during exercise' club; J Physiol; 590(Pt 12) ; pp. 2835-2836; Jun. 2012.
Somfay et al.; Dose-response effect of oxygen on hyperinflation and exercise endurance in non-hypoxaemic COPD patients; European Respiratory Journal 18; pp. 77-84; Jul. 2001.
Somfay et al.; Effect of hyperoxia on gas exchange and lactate kinetics following exercise on set in nonhypoxemic COPD patients; Chest; 121(2); pp. 393-400; Feb. 2002.
Stickland et al.; Distribution during exercise in health and chronic heart failure; Circ Res; 100; pp. 1371-1378; May 2007.
Streian et al.; Glomectomy in carotid sinus syncope and associated arrythmias: Symptomatic bradycardia, atrial flutter and atrial fibrillation; Rom J Intern Med; 44(2); pp. 153-163; 2006 (year of pub. sufficiently earlier than effective US filed and any foreign priority date).
Streian et al.; Glomectomy in carotid sinus syncope; Rev. Roum. Med.—Med. Int.; 26(1); pp. 47-52; Jan.-Mar. 1988.
Syed et al.; Percutaneous superficial temporal artery access for carotid artery stenting in patients with a hostile aortic arch; J Endovasc Ther; 18(5); pp. 729-733; Oct. 2011.
Tamura et al.; A morphometric study of the carotid sinus nerve in patients with diabetes mellitus and chronic alchoholism; Journal of the Autonomic Nervous System; 23; pp. 9-15; Jun. 1988.
Tchibukmacher, N.; Surgical anatomy of carotid sinus nerve and intercarotid ganglion; Surgery, Gynecology and Obstetrics; 67; pp. 740-745; 1938 (year of pub. sufficiently earlier than effective US filing date and any foreign priority date).

(56) References Cited

OTHER PUBLICATIONS

Timmers et al.; Denervation of carotid baro- and chemoreceptors in humans; J Physiol; 553(1); pp. 3-11; Nov. 2003.
Toorop et al.; Anatomy of the carotid sinus nerve and surgical implications in carotid sinus syndrome; J Vasc Surg; 50; pp. 177-182; Jul. 2009.
Toorop et al.; Effective surgical treatment of the carotid sinus syndrome; J Cardiovasc Surg.; 50; pp. 683-686; Oct. 2009.
Tubbs et al.; Anatomic landmarks for nerves of the neck: a vade mecum for neurosurgeons; Operative Neurosurgery; 56(ONS Suppl 2); pp. ONS256-ONS260; Apr. 2005.
Van Der Mey et al.; Management of carotid body tumors; Otolaryngol Clin North Am.; 34(5); pp. 907-924; Oct. 2001.
Vermeire et al.; Carotid body resection in patients with severe chronic airflow limitation; Bull Eur Physiopathol Respir; 23 Suppl 11; pp. 165s-166s; Aug. 1987.
Ward et al.; Embolization: An adjunctive measure for removal of carotid body tumors; Laryngoscope; 98; pp. 1287-1291; Dec. 1988.
Wasserman et al.; Effect of carotid body resection on ventilatory and acid-base control during exercise; Journal of Applied Physiology; 39(3); pp. 354-358; Aug. 1975.
Wasserman et al.; Ventilation during exercise in chronic heart failure; Basic Res Cardiol; 91(suppl. 1); pp. 1-11; 1996 (year of pub. sufficiently earlier than effective US filed and any foreign priority date).
Whipp et al.; Physiologic changes following bilateral carotid-body resection in patients with chronic obstructive pulmonary disease; Chest; 101(3); pp. 656-661; Mar. 1992.
Whipp, B.J.; Carotid bodies and breathing in humans; Thorax; 49(11); pp. 1081-1084; Nov. 1994.
Williams et al.; Carotid body tumor; Arch Surg.; 127; pp. 963-968; Aug. 1992.
Winter et al.; Immediate effects of bilateral carotid body resection on total respiratory resistance and compliance in humans; Adv Exp Med Biol; 551; pp. 15-21; 2005 (year of pub. sufficiently earlier than effective US filed and any foreign priority date).
Winter, B.; Bilateral carotid body resection for asthma and emphysema; International Surgery; 57(6); pp. 458-466; Jun. 1972.
Winter, B.; Carotid body resection in chronic obstructive pulmonary disease; Chest; 100(3); p. 883; Sep. 1991.
Winter, B.; Carotid body resection: Controversy—confusion—conflict; Ann thorac Surg.; 16(6); pp. 648-659; Dec. 1973.
Wood et al.; Bilateral removal of carotid bodies for asthma; thorax; 20(6); pp. 570-573; Nov. 1965.
Khan et al.; Anatomical variations in human carotid bodies; J. Clin. Pathol.; 41(11); pp. 1196-1199; Nov. 1988.
Holton et al.; The effects of bilateral removal of the carotid bodies and denervation of the carotid sinuses in two human subjects; J. Physiol.; 181(2); pp. 365-378; Nov. 1965.
Petersen et al.; Lesion dimensions during temperature-controlled radiofrequency catheter ablation of left ventricular porcine myocardium impact of ablation site; electrode size, and convective cooling; Circulation; 99(2); pp. 319-325; Jan. 1999.
Sehirli et al.; The diameters of common carotid artery and its branches in newborns; Surg. Radiol. Anat.; 27(4); pp. 292-296; Nov. 2005.
Wittkampf et al.; Control of radiofrequency lesion size by power regulation; Circulation; 80(4); pp. 962-968; Oct. 1989.
Hlavka et al.; U.S. Appl. No. 14/811,581 entitled "Systems and methods for treating dyspnea, including via electrical afferent signal blocking," filed Jul. 28, 2015.
Ivancev et al.; Novel access technique facilitating carotid artery stenting, Vascular; 14(4); pp. 219-222; Jul. 1, 2006.
Marietta et al.; Cardiovascular stability during carotid endarterectomy: Endotracheal intubation verus laryngeal mask airway; Journal of Clinical Anesthesia; 10(1); pp. 54-57; Feb. 1, 1998.

\* cited by examiner

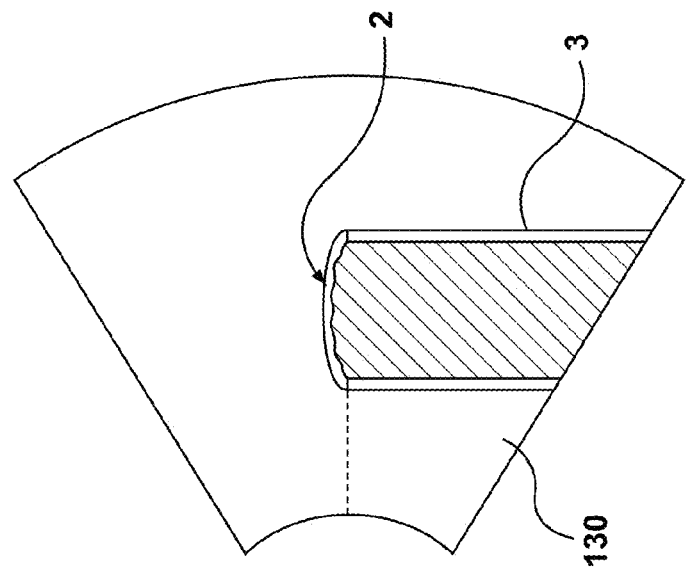
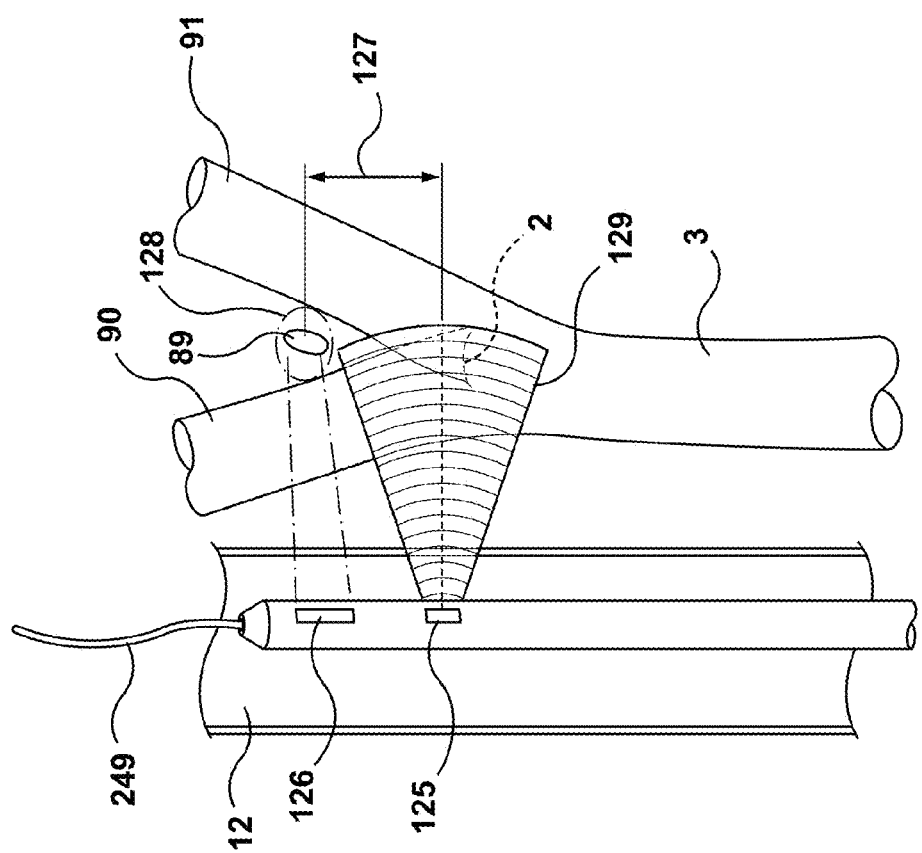
FIG. 5A
FIG. 5B

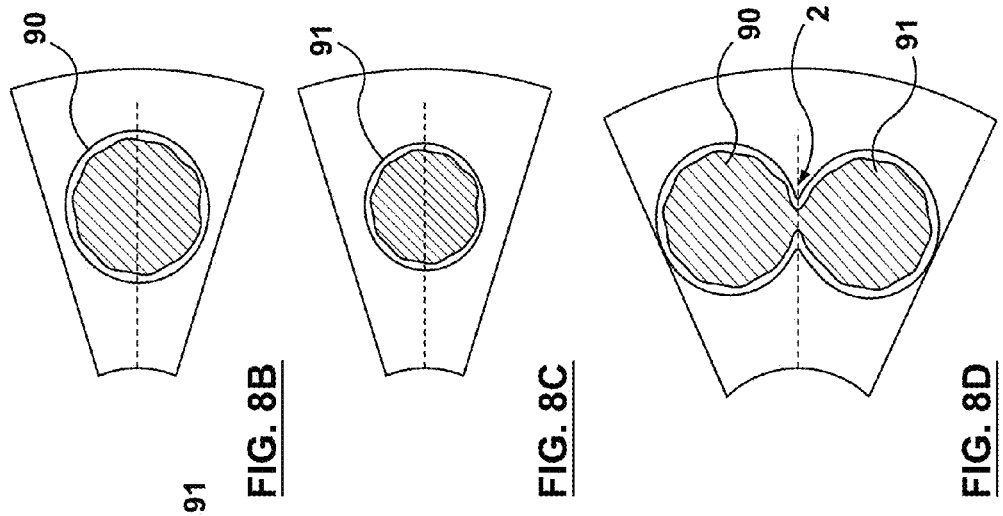
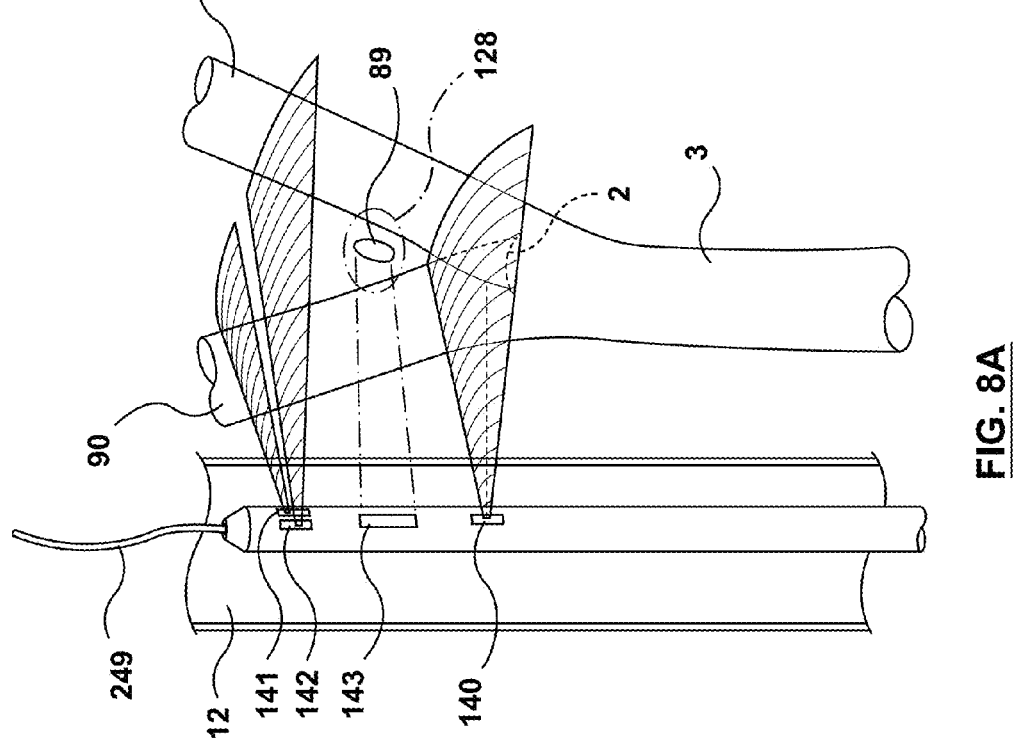
FIG. 8B
FIG. 8C
FIG. 8D
FIG. 8A

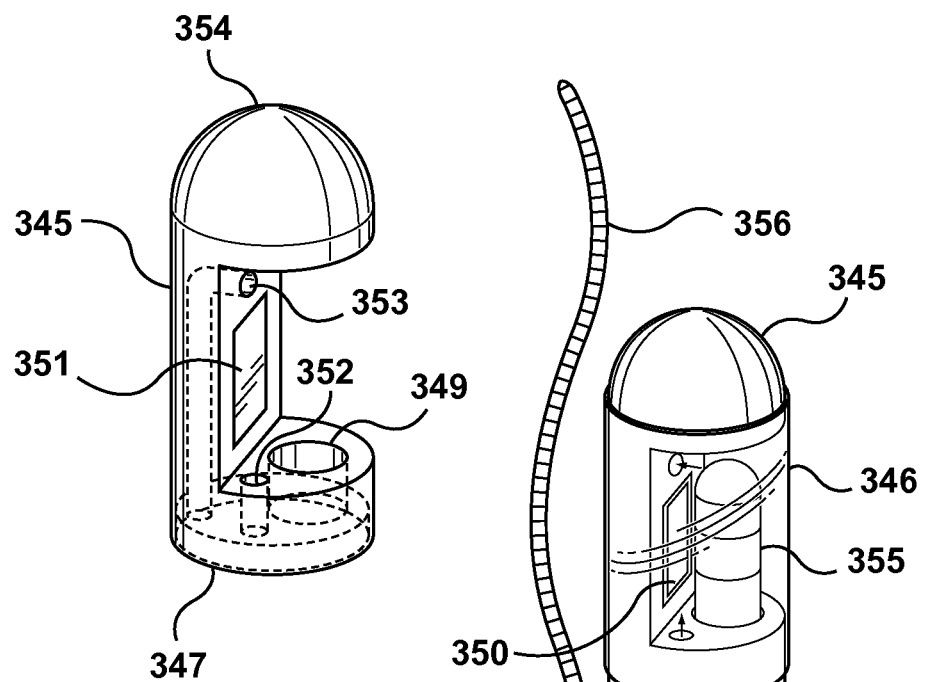
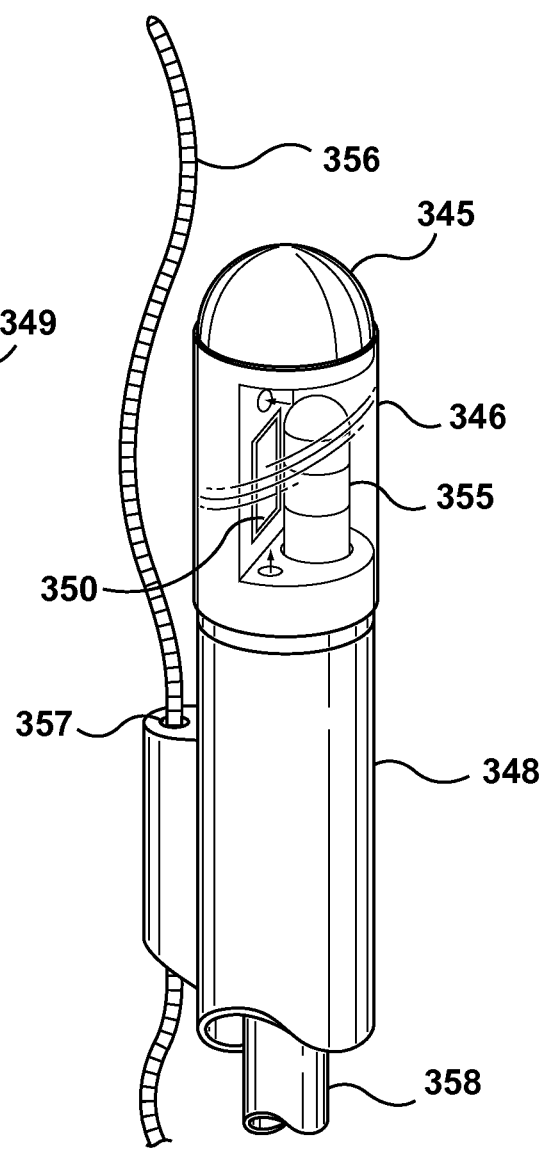
FIG. 15A
FIG. 15B

```
0002 20150115  20150117T213425
TAP residual norm 0.34W
Depth deviation mean max 0.08 0.18 mm
2.00 16 07 2.29 1.93
2.50 17 08 2.57 2.44
3.00 18 09 2.90 3.04
3.50 19 09 3.27 3.40
4.00 19 11 3.27 4.06
4.50 19 12 3.27 4.37
5.00 20 12 3.70 4.85
5.50 20 14 3.70 5.51
6.00 20 15 3.70 5.82
6.50 21 15 4.18 6.40
7.00 21 17 4.18 7.01
7.50 22 17 4.73 7.63
8.00 22 18 4.73 7.91
8.50 22 20 4.73 8.43
9.00 22 23 4.73 9.08
```

FIG. 25

CAROTID BODY ABLATION WITH A TRANSVENOUS ULTRASOUND IMAGING AND ABLATION CATHETER

INCORPORATION BY REFERENCE

This application claims priority to the following U.S. Provisional applications, which are incorporated by reference herein: App. No. 61/952,015, filed Mar. 12, 2014; App. No. 62/017,148, filed Jun. 25, 2014; and App. No. 62/049,980, filed Sep. 12, 2014.

The following applications are also incorporated herein by reference: U.S. Publication No. 2014/0005706, which published on Jan. 2, 2014; and U.S. Publication 2014/0350401, which published on Nov. 27, 2014.

All publications and patent applications mentioned in this specification are herein incorporated by reference to the same extent as if each individual publication or patent application was specifically and individually indicated to be incorporated by reference.

TECHNICAL FIELD

The present disclosure is directed generally to systems and methods for treating patients having sympathetically mediated disease associated at least in part with augmented peripheral chemoreflex or heightened sympathetic activation by ablating at least one of a carotid body, two carotid bodies, and a nerve associated therewith.

BACKGROUND

It is known that an imbalance of the autonomic nervous system is associated with several disease states. Restoration of autonomic balance has been a target of several medical treatments including modalities such as pharmacological, device-based, and electrical stimulation. For example, beta blockers are a class of drugs used to reduce sympathetic activity to treat cardiac arrhythmias and hypertension; Gelfand and Levin (U.S. Pat. No. 7,162,303) describe a device-based treatment used to decrease renal sympathetic activity to treat heart failure, hypertension, and renal failure; Yun and Yuarn-Bor (U.S. Pat. No. 7,149,574; U.S. Pat. No. 7,363,076; U.S. Pat. No. 7,738,952) describe a method of restoring autonomic balance by increasing parasympathetic activity to treat disease associated with parasympathetic attrition; Kieval, Burns and Serdar (U.S. Pat. No. 8,060,206) describe an electrical pulse generator that stimulates a baroreceptor, increasing parasympathetic activity, in response to high blood pressure; Hlavka and Elliott (US 2010/0070004) describe an implantable electrical stimulator in communication with an afferent neural pathway of a carotid body chemoreceptor to control dyspnea via electrical neuromodulation. More recently, Carotid Body Ablation (CBA) has been conceived for treating sympathetically mediated diseases.

SUMMARY

This disclosure is related to methods, devices, and systems for reducing afferent signaling between a peripheral chemoreceptor and the central nervous system. The disclosure includes methods, devices, and systems for directed energy ablation of a carotid body or its associated nerves. In particular, methods and devices for ablating tissue such as a carotid body, carotid septum or nerves associated with a carotid body that is proximate a vessel such as a vein or artery with an endovascular carotid body ablation (CBA) catheter having means for imaging and ablation.

A carotid body may be ablated by placing a directed energy emitter within or against the wall of an internal jugular vein or one of its tributaries adjacent to the carotid body of interest, then aiming and activating the directed energy emitter thereby raising the temperature of the perivenous space containing the carotid body or its nerves to an extent and duration sufficient to ablate tissue of a carotid septum, carotid body or its nerves.

In an exemplary procedure a location of perivenous space associated with a carotid body is identified, then a directed energy emitter is placed against or within the interior wall of an internal jugular vein adjacent to the identified location, then directed energy ablation parameters are selected and the directed energy emitter is activated thereby ablating the carotid body, whereby the orientation and position of the directed energy emitter and the selection of directed energy ablation parameters provides for ablation of the carotid body without substantial collateral damage to adjacent functional structures.

In a further exemplary procedure a location of extravascular space associated with a carotid body is identified, then a directed energy emitter is placed proximate to the identified location, then directed energy ablation parameters are selected and the directed energy emitter is activated thereby ablating the carotid body, whereby the position of the directed energy emitter and the selection of directed energy ablation parameters provides for ablation of the carotid body without substantial collateral damage to adjacent functional structures.

One aspect of the disclosure is an ultrasound ablation catheter configured to interact with an intravascular ultrasound ("IVUS") imaging catheter, the ultrasound ablation catheter comprising: a distal region and a proximal region; an IVUS lumen to receive therethrough an IVUS imaging catheter extending from the proximal region to the distal region; an echolucent chamber at the distal region; and an ultrasound ablation transducer within the echolucent chamber, wherein the IVUS lumen is configured to position the IVUS imaging catheter within a direction of aim of the ultrasound ablation transducer in a deployed state and out of the direction of aim in a retracted state.

One aspect of the disclosure is an ultrasound ablation catheter configured to interact with an intravascular ultrasound imaging ("IVUS") catheter having an ultrasound imaging transducer, the ultrasound ablation catheter comprising: a distal region and a proximal region; an IVUS lumen configured to receive therethrough an IVUS imaging catheter extending from the proximal region to the distal region; an echolucent chamber at the distal region; and an ultrasound ablation transducer within the echolucent chamber, wherein the IVUS lumen is configured to position the ultrasound imaging transducer of the IVUS catheter distal to the ultrasound ablation transducer such that the ultrasound ablation transducer may deliver ablation energy while the ultrasound imaging transducer is transmitting and receiving waves to provide an image while ablating.

One aspect of the disclosure is an ultrasound ablation catheter, comprising: a distal assembly comprising an ultrasound ablation transducer, an echolucent shell, and an ablation direction fiducial marker, the echolucent shell at least partially defining a distal chamber, the ultrasound ablation transducer disposed within the distal chamber, the distal assembly adapted to house therein an ultrasound imaging transducer, the ablation direction fiducial marker positioned relative to the ultrasound ablation transducer and adapted to, when an ultrasound imaging transducer is positioned and activated within the distal assembly, create an aiming artifact on an image created by the ultrasound imaging transducer, the aiming artifact adapted to be used to indicate a direction of ablation; and an elongate shaft extending proximally from the distal assembly.

One aspect of the disclosure herein is an ultrasound ablation catheter, comprising: a distal assembly comprising an ultrasound ablation transducer and a echolucent shell, the echolucent shell at least partially defining a distal chamber, the ultrasound ablation transducer disposed within the distal chamber, the distal assembly adapted to house therein an ultrasound imaging transducer, wherein the echolucent shell has a first thickness at a first axial location of the ablation ultrasound transducer, and a second thickness greater than the first thickness at a second axial location distal to a distal end of the ablation ultrasound transducer; and an elongate shaft extending proximally from the distal assembly.

One aspect of the disclosure herein is an ultrasound ablation catheter, comprising: a distal assembly comprising an ultrasound ablation transducer and a echolucent shell, the echolucent shell at least partially defining a distal chamber, the ultrasound ablation transducer disposed within the distal chamber, the distal assembly adapted to house therein an ultrasound imaging transducer; a fluid lumen, the fluid lumen in fluid communication with the ultrasound ablation transducer, the fluid lumen also comprising an electrical connector in electrical communication with the ablation ultrasound transducer; and an elongate shaft extending proximally from the distal assembly.

One aspect of the disclosure herein is an ultrasound ablation catheter, comprising: a distal assembly comprising an ultrasound ablation transducer and a echolucent shell, the echolucent shell at least partially defining a distal chamber, the ultrasound ablation transducer disposed within the distal chamber, the distal assembly adapted to house therein an ultrasound imaging transducer; an elongate shaft extending proximally from the distal assembly; and a manifold secured to and extending distally from at least a portion the elongate shaft, the ablation ultrasound transducer mounted to the manifold.

In any of the ablation catheters herein the catheter can further comprises a cooling fluid lumen for cooling the echolucent chamber. In any of the ablation catheters herein a direction of aim of the ultrasound ablation catheter can be in a radial direction from the catheter within an imaging plane generated by the IVUS imaging catheter when in a deployed state. In any of the ablation catheters herein the catheter can further comprise a mating feature at the proximal region for coupling with the IVUS imaging catheter wherein the mating feature is associated with an actuator that transitions the IVUS imaging catheter between a deployed state and a retracted state. In any of the ablation catheters herein the catheter can be configured for controllable deflection of the distal region, wherein a plane of deflection is coplanar with the ultrasound ablation transducer. In any of the ablation catheters herein the catheter can further comprise a lumen configured to receive a guidewire.

In any of the ablation catheters herein the catheter can further comprise an acoustic insulator to shield passage of ultrasound ablation energy, wherein the acoustic insulator comprises microspheres of air embedded in epoxy. The acoustic insulator can have a thickness of about 200 to 300 microns and comprises microspheres having a diameter in a range of about 15 to 25 microns and microspheres having a diameter in a range of about 180 to 210 microns. 10/126.

In any of the ablation catheters herein the catheter can further comprise a fiducial marker having a position with respect to the imaging transducer and the direction of aim of the ablation transducer. The fiducial marker can be a hollow tube filled with air. The fiducial marker can be axially aligned with the ultrasound imaging catheter when the ultrasound image transducer is in an active position in the distal assembly. The fiducial marker can be disposed relative to the ultrasound ablation transducer such that the direction of the ablation energy emitted from the ultrasound ablation transducer can be determined based on the location of the indicator on the image. The fiducial marker can be secured to the echolucent shell. The echolucent shell can comprise first and second membranes, and the fiducial marker can be secured between the first and second membranes. The fiducial marker has a curved configuration, such as a partial tubular member. The fiducial marker can be an extension of a support member disposed proximal to the ablation direction fiducial marker. The fiducial marker can be an echo-opaque material, such as stainless steel.

In any of the ablation catheters herein the ablation catheter can be configured to be inserted through a jugular vein of a patient and wherein the ultrasound ablation transducer can be configured to be placed in proximity to a target ablation site including a carotid body.

In any of the ablation catheters herein the catheter can comprise a distal assembly further comprising a lumen therein configured to receive therethrough an ultrasound imaging catheter.

In any of the ablation catheters herein the ablation transducer can be a flat transducer with an axial axis that is parallel to the longitudinal axis of the elongate shaft in a straight configuration. A flat transducer can be disposed in an outer radial portion of the distal region of the catheter.

In any of the ablation catheters herein an echolucent shell can have a first thickness at a first axial location of the ablation ultrasound transducer, and a second thickness greater than the first thickness at a second axial location distal to the ablation ultrasound transducer. The echolucent shell can comprise at least first and second membrane sections that are affixed together in the second axial location.

In any of the ablation catheters herein the catheter can further comprise a fluid lumen, the fluid lumen in fluid communication with the ultrasound ablation transducer, the fluid lumen also comprising an electrical connector in electrical communication with the ablation ultrasound transducer.

In any of the ablation catheters herein the catheter can further comprise a manifold secured to and extending distally from at least a portion the elongate shaft, and the ablation ultrasound transducer can be mounted to the manifold. The catheter can further comprise a wafer secured between the ablation ultrasound transducer and the manifold. The manifold can comprise a lumen adapted to receive an ultrasound imaging catheter therein. The manifold can further comprise at least one fluid exit lumen in communication with a proximal region of the catheter. The manifold can comprise a recess defined by side edges and a back plate, the recess adapted to receive therein the ultrasound ablation transducer, wherein the ablation transducer is secured within the recess such that the side edges extend radially outward relative to the ablation transducer to allow the free flow of cooling fluid over the ablation transducer. The manifold can be configured to induce turbulent flow of cooling fluid over the ablation transducer.

One aspect of the disclosure is a method in a computer system, comprising: receiving as input an ultrasound-based image, the ultrasound-based image derived from signals received from an ultrasound imaging transducer; determining the location of an artifact in the ultrasound-based image, the artifact having been created by a fiducial marker on an ultrasound ablation transducer in response to ultrasound waves generated by the ultrasound imaging transducer; based on the location of the artifact, determining a direction of aim of ablation energy from the ultrasound ablation transducer; and creating an augmented ultrasound-based image as output for display on a monitor, the augmented ultrasound-based image including the ultrasound-based image and the direction of aim of the of ablation energy from the ultrasound ablation transducer.

One aspect of the disclosure is a computer-implemented method comprising: receiving a video or ultrasound-based image of a target ablation site for carotid body ablation created from ultrasound signals transmitted from an ultrasound transceiver, the video or ultrasound-based image having been captured while an ultrasound ablation transducer is located proximate to the target ablation site for carotid body ablation; augmenting the video or ultrasound-based image by one or more visual aids, animations or messages, wherein the one or more visual aids, animations or messages include information regarding a direction of aim of ablation energy from the ultrasound ablation transducer for carotid body ablation; and displaying the augmented video or ultrasound-based image on a user interface.

One aspect of the disclosure is a computer-implemented method comprising: receiving a video or ultrasound-based image of a target ablation site for carotid body ablation created from ultrasound signals transmitted from an ultrasound transceiver, the video or ultrasound-based image having been captured while an ultrasound ablation transducer is located proximate to the target ablation site for carotid body ablation; augmenting the video or ultrasound-based image by one or more visual aids, animations or messages, wherein the one or more visual aids, animations or messages include information regarding an estimated location of an ablation area of an ultrasound ablation transducer being located proximate to the target ablation site for carotid body ablation; and displaying the augmented video or ultrasound-based image on a user interface.

One aspect of the disclosure is a system for imaging and ablation of a carotid body having image augmentation comprising: a catheter with an ultrasound imaging transducer and an ablation element; an ablation console; an ultrasound imaging console configured for transmitting and receiving signals to and from the imaging transducer; a computer executed algorithm that creates an ultrasound-based image from signals received from the imaging transducer; an image augmentation unit that processes the ultrasound-based image with a computer algorithm that creates an augmented image; and a monitor to display the augmented image.

In any of the methods or systems herein that can create and/or display an augmented video or ultrasound-based image, determining a location of an artifact in the ultrasound-based image can comprise recognizing a portion of the ultrasound-based image that substantially does not change shape when the orientation of the ultrasound-based image changes in response to movement of the ultrasound imaging transducer.

In any of the methods or systems herein that can create and/or display an augmented video or ultrasound-based image, one or more visual aids, animations or messages can include information regarding an estimated location of an ablation area of the ultrasound ablation transducer.

In any of the methods or systems herein that can create and/or display an augmented video or ultrasound-based image, information regarding an estimated location of an ablation area can include a direction in which the ultrasound ablation transducer is facing and/or a direction in which the ultrasound ablation transducer will deliver ablation energy.

In any of the methods or systems herein that can create and/or display an augmented video or ultrasound-based image, information regarding an estimated location of an ablation area can include an estimated depth and/or width of an ablation area of the ultrasound ablation transducer.

In any of the methods or systems herein that can create and/or display an augmented video or ultrasound-based image, information regarding an estimated location of an ablation area can includes an estimated outline of the ablation area.

In any of the methods or systems herein that can create and/or display an augmented video or ultrasound-based image, information regarding an estimated location of an ablation area of an ultrasound ablation transducer can be determined by taking into account user defined and/or automatically set parameters of an ablation procedure.

In any of the methods or systems herein that can create and/or display an augmented video or ultrasound-based image, an estimated location of an ablation area of an ultrasound ablation transducer can be determined at least partially based on a selected ablation energy profile.

In any of the methods or systems herein that can create and/or display an augmented video or ultrasound-based image, an estimated location of an ablation area of an ultrasound ablation transducer can be determined by taking into account one or more anatomical parameters of a candidate for ablation treatment.

In any of the methods or systems herein that can create and/or display an augmented video or ultrasound-based image, an estimated location of an ablation area of an ultrasound ablation transducer can be determined by taking into account information regarding ablation properties of a specific type of catheter carrying the ultrasound ablation transducer.

In any of the methods or systems herein that can create and/or display an augmented video or ultrasound-based image, information regarding ablation properties of a type of a catheter carrying the ultrasound ablation transducer can include information correlating an estimated lesion depth and/or width with ablation energy and duration for the specific type of catheter.

In any of the methods or systems herein that can create and/or display an augmented video or ultrasound-based image, one or more visual aids, animations or messages can further include information regarding a direction of aim of ablation energy from an ultrasound ablation transducer for carotid body ablation.

In any of the methods or systems herein that can create and/or display an augmented video or ultrasound-based image, information regarding the direction of aim of ablation energy from the ultrasound ablation transducer for carotid body ablation can be determined by using a position of a fiducial marker or an aiming artifact in a video or ultrasound-based image.

In any of the methods or systems herein that can create and/or display an augmented video or ultrasound-based image, a fiducial marker can be arranged in a predefined position relative to the direction of aim of an ablation catheter carrying the ultrasound ablation transducer.

In any of the methods or systems herein that can create and/or display an augmented video or ultrasound-based image, a fiducial marker can include a band or tube of echo-opaque material or structure or a structure having distinctly hyperechoic or hypoechoic material or structure compared to surrounding structures and/or surrounding tissue when located proximate to the target ablation site.

In any of the methods or systems herein that can create and/or display an augmented video or ultrasound-based image, a fiducial marker can include a piezoelectric element.

In any of the methods or systems herein that can create and/or display an augmented video or ultrasound-based image, a fiducial marker is positioned on an ablation catheter carrying the ultrasound ablation transducer to indicate on an ultrasound-based image the opposite direction of delivery of ablation energy.

In any of the methods or systems herein that can create and/or display an augmented video or ultrasound-based image, information regarding the direction of aim of ablation energy from the ultrasound ablation transducer for carotid body ablation can be determined by using a position of multiple fiducial markers or aiming artifacts in a video or ultrasound-based image.

In any of the methods or systems herein that can create and/or display an augmented video or ultrasound-based image, a video or ultrasound-based image can be created with an IVUS catheter.

In any of the methods or systems herein that can create and/or display an augmented video or ultrasound-based image, an IVUS catheter can be placed in a jugular vein of a candidate for carotid body ablation in proximity to a carotid bifurcation.

Any of the methods or systems herein that can create and/or display an augmented video or ultrasound-based image can further comprise determining a scale of the video or ultrasound-based image based of a known dimension of a catheter or aiming artifact visible in the video or ultrasound-based image.

In any of the methods or systems herein that can create and/or display an augmented video or ultrasound-based image, one or more visual aids, animations or messages can include information of one or more distances between anatomical features of the target ablation site.

In any of the methods or systems herein that can create and/or display an augmented video or ultrasound-based image, one or more distances can include one or more of a relative position of an internal jugular vein, a carotid septum, an internal carotid artery, an external carotid artery, or carotid septum boundaries to a reference point, artery diameters, changes in artery diameters, changes in relative position of anatomical features, size and relative position of an estimated ablation or created ablation.

Any of the methods or systems herein that can create and/or display an augmented video or ultrasound-based image can further comprise providing a user with ablation therapy instructions or suggestions based on the one or more distances between anatomical features of the target ablation site.

One aspect of the disclosure is a computer system for monitoring a carotid ablation procedure being configured to perform the operations of any of the methods herein. The computer systems can comprise a display configured to display augmented video or ultrasound-based image and an input interface configured for receiving the video or ultrasound-based image from an ultrasound imaging device. A computer readable medium can include instructions which when executed by a computer system let the computer system carry out the operations of any of the methods herein.

In any of the methods or systems herein that can create and/or display an augmented video or ultrasound-based image, an augmented image can be overlaid on the ultrasound-based image and indicates the direction of delivery of ablation energy, carotid arteries, an estimated ablation outline, estimated ablation depth, and estimated created ablation positions. A computer algorithm can control the ablation console using calculations of relative positions of estimated ablation position and carotid arteries.

One aspect of the disclosure a computer implemented method for determining parameters for a carotid body ablation procedure, the method comprising: receiving information characterizing a dimension of a desired ablation volume of a ultrasound carotid body ablation procedure; and automatically determining one or more ultrasound ablation delivery parameters based on the received information; and providing as output to a ultrasound ablation delivery system the delivery parameters.

One aspect of the disclosure is a method in a computer system, comprising: receiving as input a distance, measured from an ultrasound-based image derived from a signal received from an ultrasound transducer positioned in a jugular vein, from a wall of a jugular vein to a line connecting portions of an internal and external carotid arteries; determining ultrasound ablation delivery parameters based on the input distance; and providing as output to a ultrasound ablation delivery system the delivery parameters.

In any of the methods or systems herein that can determine parameters for a carotid body ablation procedure, one or more ultrasound ablation delivery parameters can include an ablation energy profile to be used by the ablation delivery system.

In any of the methods or systems herein that can determine parameters for a carotid body ablation procedure, an ablation energy profile can specify a profile of an amount of acoustic power and duration of delivery of the ablation energy during a treatment procedure.

In any of the methods or systems herein that can determine parameters for a carotid body ablation procedure, one or more ultrasound ablation delivery parameters can be determined by taking into account one or more anatomical parameters of a candidate for ablation treatment.

In any of the methods or systems herein that can determine parameters for a carotid body ablation procedure, one or more ultrasound ablation delivery parameters can be determined by taking into account information regarding ablation transducer properties of a specific catheter carrying the ultrasound ablation transducer.

In any of the methods or systems herein that can determine parameters for a carotid body ablation procedure, information regarding ablation transducer properties of a catheter carrying the ultrasound ablation transducer can include information correlating an estimated lesion depth and/or width with electrical power and duration for the specific ablation catheter.

In any of the methods or systems herein that can determine parameters for a carotid body ablation procedure, a desired ablation volume of an ultrasound carotid body ablation procedure can be automatically determined based on a video or ultrasound-based image created from ultrasound signals transmitted from an ultrasound transducer of a target ablation site for carotid body ablation.

In any of the methods or systems herein that can determine parameters for a carotid body ablation procedure, an automatic determination can include assessing position or size of one or more anatomic features in the target ablation site.

In any of the methods or systems herein that can determine parameters for a carotid body ablation procedure, one or more anatomic features can include a carotid septum, a carotid body, internal and external carotid arteries and a jugular vein.

In any of the methods or systems herein that can determine parameters for a carotid body ablation procedure, determining one or more ultrasound ablation delivery parameters can include using information retrieved from prior ablation procedures and/or evaluation of numerical models of simulation procedures.

Any of the methods or systems herein that can determine parameters for a carotid body ablation procedure can further include automatically monitoring a movement of a patient's body or head; identifying a movement that meets a predetermined significance criterion indicating a risk for the patient; and generating a signal indicating that a movement has met a predetermined significance criterion.

In any of the methods or systems herein that can determine parameters for a carotid body ablation procedure, one or more ultrasound ablation delivery parameters can include duration of energy delivery and acoustic power, wherein the acoustic power is in a range between 2 watts and 25 watts and the duration is in a range between 5 seconds and 25 seconds.

One aspect of the disclosure is a computer system for monitoring a carotid ablation procedure being configured to perform the operations of any one of the methods herein. A computer readable medium can include instructions which when executed by a computer system let the computer system carry out the operations of any of the methods herein.

BRIEF DESCRIPTION OF THE DRAWINGS

FIGS. 5A, 5B, 6A, 6B, 7A, 7B, 7C, 8A, 8B, 8C, and 8D are schematic illustrations of an ultrasound CBA catheter having one or more diagnostic catheters used to align with vascular landmarks delivered to an internal jugular vein.

FIGS. 15A and 15B are schematic illustrations of an ultrasound CBA catheter configured to accept a separate ultrasound imaging catheter.

FIG. 25 is a lesion dosimetry lookup table.

DETAILED DESCRIPTION

Figure 1:
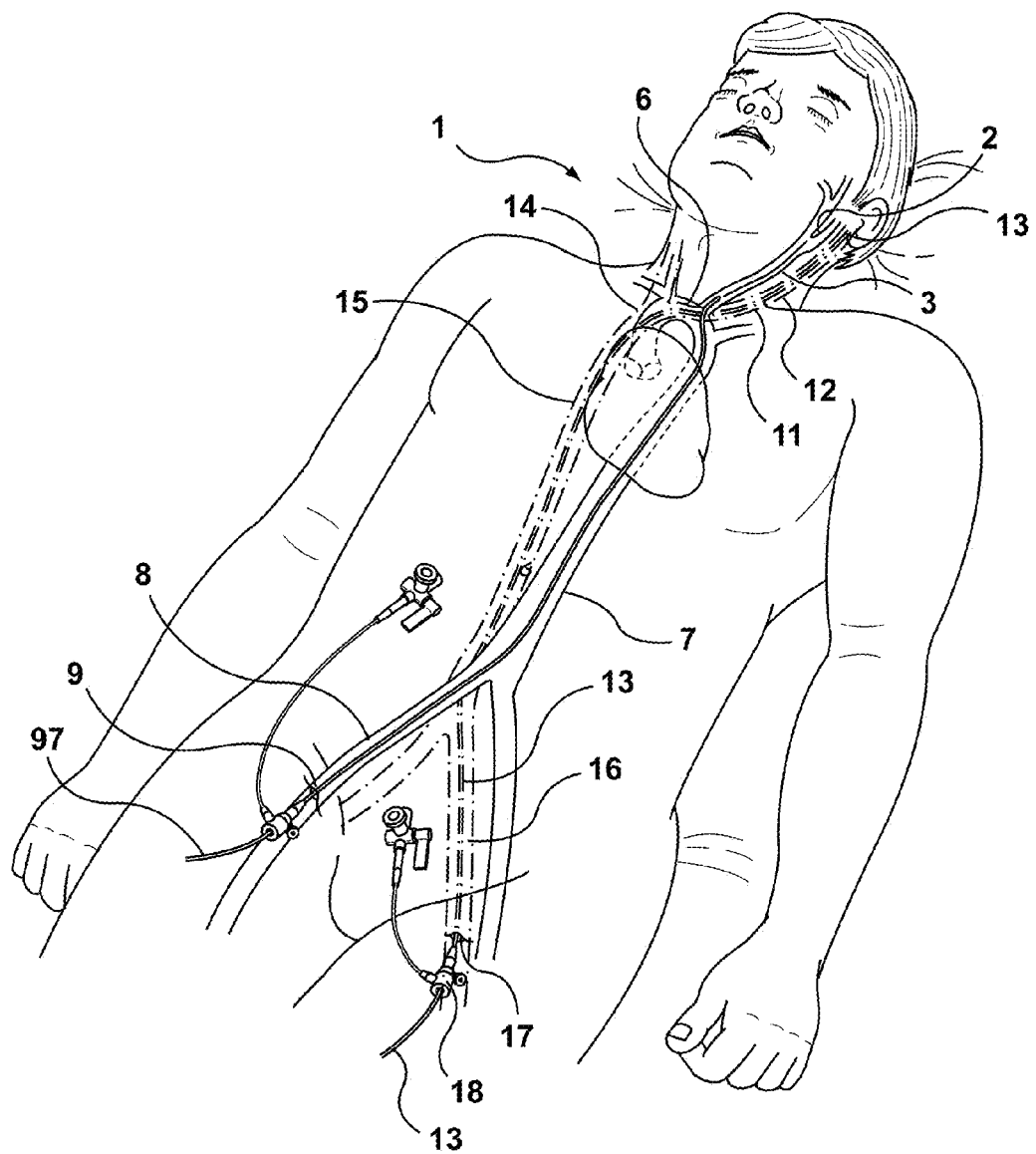
FIG. 1 depicts in simplified schematic form a placement of an endovascular directed energy ablation catheter into a patient via a femoral vein puncture.

The disclosure herein is related to systems, devices, and methods for carotid body ablation to treat patients having a sympathetically mediated disease (e.g., cardiac, renal, metabolic, or pulmonary disease such as hypertension, CHF, sleep apnea, sleep disordered breathing, diabetes, insulin resistance) at least partially resulting from augmented peripheral chemoreflex (e.g., peripheral chemoreceptor hypersensitivity, peripheral chemosensor hyperactivity) or heightened sympathetic activation. Carotid body ablation as used herein refers generally to completely or partially ablating one or both carotid bodies, carotid body nerves, intercarotid septums, or peripheral chemoreceptors. A main therapy pathway is a reduction of peripheral chemoreflex or reduction of afferent nerve signaling from a carotid body (CB), which results in a reduction of central sympathetic tone. Higher than normal chronic or intermittent activity of afferent carotid body nerves is considered enhanced chemoreflex for the purpose of this application regardless of its cause. Other important benefits such as increase of parasympathetic tone, vagal tone and specifically baroreflex and baroreceptor activity reduction of dyspnea, hyperventilation and breathing rate may be expected in some patients. Secondary to reduction of breathing rate additional increase of parasympathetic tone may be expected in some cases.

Augmented peripheral chemoreflex (e.g., carotid body activation) leads to increases in sympathetic nervous system activity, which is in turn primarily responsible for the progression of chronic disease as well as debilitating symptoms and adverse events seen in the intended patient populations. Carotid bodies contain cells that are sensitive to oxygen and carbon dioxide. Carotid bodies also respond to blood flow, blood pH, blood glucose level and possibly other variables. Thus, carotid body ablation may be a treatment for patients, for example having hypertension, heart disease or diabetes, even if chemosensitive cells are not activated.

Targets:

To inhibit or suppress a peripheral chemoreflex, anatomical targets for ablation (also referred to as targeted tissue, target ablation sites, or target sites) may include at least a portion of at least one carotid body, an aortic body, nerves associated with a peripheral chemoreceptor (e.g., carotid body nerves, carotid sinus nerve, carotid plexus), small blood vessels feeding a peripheral chemoreceptor, carotid body parenchyma, chemosensitive cells (e.g., glomus cells), tissue in a location where a carotid body is suspected to reside (e.g., a location based on pre-operative imaging or anatomical likelihood), an intercarotid septum, a portion of an intercarotid septum, a substantial part of an intercarotid septum or a combination thereof. As used herein, ablation of a carotid body may refer to ablation of any of these target ablation sites.

An intercarotid septum, which is also referred to herein as a carotid septum, is herein defined as a wedge or triangular segment of tissue with the following boundaries: a saddle of a carotid bifurcation defines a caudal aspect (i.e., an apex) of a carotid septum; facing walls of internal and external carotid arteries define two sides of the carotid septum; a cranial boundary of a carotid septum extends between these arteries and may be defined as cranial to a carotid body but caudal to any important non-target nerve structures (e.g., a hypoglossal nerve) that might be in the region, for example a cranial boundary may be about 10 mm to about 15 mm from the saddle of the carotid bifurcation; medial and lateral walls of the carotid septum are generally defined by planes approximately tangent to the internal and external carotid arteries; one of the planes is tangent to the lateral walls of the internal and external carotid arteries and the other plane is tangent to the medial walls of these arteries. An intercarotid septum is disposed between the medial and lateral walls. An intercarotid septum may contain, completely or partially, a carotid body and may be absent of important non-target structures such as a vagus nerve or sympathetic nerves or a hypoglossal nerve. An intercarotid septum may include some baroreceptors or baroreceptor nerves. An intercarotid septum may also include intercarotid plexus nerves, small blood vessels and fat. An intercarotid septum may be a target for ablation. Even if a carotid body or carotid body nerve cannot be easily identified visually to target specifically an intercarotid septum may be targeted with a high probability of ablating a carotid body and safely avoiding non-target nerves. Multiple ablations may be created within a carotid septum to cover an increased volume of tissue to increase a probability of ablating a carotid body. Multiple ablations may overlap or be discrete within a carotid septum.

Carotid body nerves are anatomically defined herein as carotid plexus nerves and carotid sinus nerves. Carotid body nerves are functionally defined herein as nerves that conduct information from a carotid body to a central nervous system. Carotid body nerves can be referred to herein as one or more nerves that are associated with the carotid body.

An ablation may be focused exclusively on targeted tissue, or be focused on the targeted tissue while safely ablating tissue proximate to the targeted tissue (e.g., to ensure the targeted tissue is ablated or as an approach to gain access to the targeted tissue). An ablation region may be as big as a peripheral chemoreceptor (e.g., carotid body or aortic body) itself, somewhat smaller, or bigger and can include one or more tissues surrounding the chemoreceptor such as blood vessels, adventitia, fascia, small blood vessels perfusing the chemoreceptor, and nerves connected to and innervating the glomus cells. An intercarotid plexus or carotid sinus nerve may be a target of ablation with an understanding that some baroreceptor nerves will be ablated together with carotid body nerves. Baroreceptors are distributed in the human arteries and have a high degree of redundancy.

Tissue may be ablated to inhibit or suppress a chemoreflex of only one of a patient's two carotid bodies. Other embodiments include ablating tissue to inhibit or suppress a chemoreflex of both of a patient's carotid bodies. In some embodiments an ablation is performed on a first carotid body, and an assessment is then performed to determine if the other carotid body should be ablated. For example, a therapeutic method may include ablation of one carotid body, measurement of resulting chemosensitivity, sympathetic activity, respiration or other parameter related to carotid body hyperactivity, and ablation of the second carotid body can be performed if desired to further reduce chemosensitivity following the unilateral ablation.

An embodiment of a therapy may substantially reduce chemoreflex without excessively reducing the baroreflex of the patient. The proposed ablation procedure may be targeted to substantially spare the carotid sinus, baroreceptors distributed in the walls of carotid arteries, particularly internal carotid arteries, and at least some of the carotid sinus nerves that conduct signals from said baroreceptors. For example, the baroreflex may be substantially spared by targeting a limited volume of ablated tissue possibly enclosing the carotid body, tissues containing a substantial number of carotid body nerves, tissues located in periadventitial space of a medial segment of a carotid bifurcation, or tissue located at the attachment of a carotid body to an artery. Said targeted ablation is enabled by visualization of the area or carotid body itself, for example by CT, CT angiography, MRI, ultrasound sonography, fluoroscopy, blood flow visualization, or injection of contrast, and positioning of an instrument in the carotid body or in close proximity while avoiding excessive damage (e.g., perforation, stenosis, thrombosis) to carotid arteries, baroreceptors, carotid sinus nerves or other important non-target nerves such as a vagus nerve or sympathetic nerves located primarily outside of the carotid septum. Thus imaging a carotid body before ablation may be instrumental in (a) selecting candidates if a carotid body is present, large enough and identified and (b) guiding therapy by providing a landmark map for an operator to guide an ablation instrument to the carotid septum, center of the carotid septum, carotid body nerves, the area of a blood vessel proximate to a carotid body, or to an area where carotid body itself or carotid body nerves may be anticipated. It may also help exclude patients in whom the carotid body is located substantially outside of the carotid septum in a position close to a vagus nerve, hypoglossal nerve, jugular vein or some other structure that can be endangered by ablation. In one embodiment only patients with a carotid body substantially located within the intercarotid septum are selected for ablation therapy.

Once a carotid body is ablated, removed or denervated, the carotid body function (e.g., carotid body chemoreflex) does not substantially return in humans, partly because in humans aortic chemoreceptors are considered undeveloped. To the contrary, once a carotid sinus baroreflex is removed it is generally compensated, after weeks or months, by the aortic or other arterial baroreceptor baroreflex. Thus, if both the carotid chemoreflex and baroreflex are removed or substantially reduced, for example by interruption of the carotid sinus nerve or intercarotid plexus nerves, the baroreflex may eventually be restored while the chemoreflex may not. The consequences of temporary removal or reduction of the baroreflex can be in some cases relatively severe and require hospitalization and management with drugs, but they generally are not life threatening, terminal or permanent. Thus, it is understood that while selective removal of carotid body chemoreflex with baroreflex preservation may be desired, it may not be absolutely necessary in some cases.

Ablation:

The term "ablation" may refer to the act of altering a tissue to suppress or inhibit its biological function or ability to respond to stimulation permanently or for an extended period of time (e.g., greater than 3 weeks, greater than 6 months, greater than a year, for several years, or for the remainder of the patient's life). Selective denervation may involve, for example, interruption of afferent nerves from a carotid body while substantially preserving nerves from a carotid sinus, which conduct baroreceptor signals, and other adjacent nerves such as hypoglossal, laryngeal, and vagal nerves. Another example of selective denervation may involve interruption of a carotid sinus nerve, or intercarotid plexus which is in communication with both a carotid body and some baroreceptors wherein chemoreflex from the carotid body is reduced permanently or for an extended period of time (e.g., years) and baroreflex is substantially restored in a short period of time (e.g., days or weeks). As used herein, the term "ablate" or a derivative thereof refers to interventions that suppress or inhibit natural chemoreceptor or afferent nerve functioning, which is in contrast to electrically neuromodulating or reversibly deactivating and reactivating chemoreceptor functioning.

Carotid Body Ablation ("CBA") as used herein refers to ablation of a target tissue wherein the desired effect is to reduce or remove the afferent neural signaling from a chemosensor (e.g., carotid body) or reducing a chemoreflex. Chemoreflex or afferent nerve activity cannot be directly measured in a practical way, thus indexes of chemoreflex such as chemosensitivity can sometimes be used instead. Chemoreflex reduction is generally indicated by a reduction of blood pressure, a reduction of an increase of ventilation and ventilation effort per unit of blood gas concentration, saturation or partial pressure change or by a reduction of central sympathetic nerve activity that can be measured indirectly. Sympathetic nerve activity can be assessed by reduction of blood pressure, measuring activity of peripheral nerves leading to muscles (MSNA), heart rate (HR), heart rate variability (HRV), production of hormones such as renin, epinephrine and angiotensin, and peripheral vascular resistance. All these parameters are measurable and can lead directly to the health improvements. In the case of CHF patients blood pH, blood $PCO_2$, degree of hyperventilation and metabolic exercise test parameters such as peak $VO_2$, and $VE/VCO_2$ slope are also important. It is believed that patients with heightened chemoreflex have low $VO_2$ and high $VE/VCO_2$ slope (index of respiratory efficiency) as a result of, for example, tachypnea and low blood $CO_2$. These parameters are also related to exercise limitations that further speed up a patient's status deterioration towards morbidity and death. It is understood that all these indexes are indirect and imperfect and intended to direct therapy to patients that are most likely to benefit or to acquire an indication of technical success of ablation rather than to prove an exact measurement of effect or guarantee a success. It has been observed that some tachyarrhythmias in cardiac patients are sympathetically mediated. Thus carotid body ablation may be instrumental in treating reversible atrial fibrillation and ventricular tachycardia.

Carotid body ablation may include methods and systems for the thermal ablation of tissue via thermal heating mechanisms. Thermal ablation may be achieved due to a direct effect on tissues and structures that are induced by the thermal stress. Additionally or alternatively, the thermal disruption may at least in part be due to alteration of vascular or peri-vascular structures (e.g., arteries, arterioles, capillaries or veins), which perfuse the carotid body and neural fibers surrounding and innervating the carotid body (e.g., nerves that transmit afferent information from carotid body chemoreceptors to the brain). Additionally or alternatively thermal disruption may be due to a healing process, fibrosis, or scarring of tissue following thermal injury, particularly when prevention of regrowth and regeneration of active tissue is desired. As used herein, thermal mechanisms for ablation may include both thermal necrosis or thermal injury or damage (e.g., via sustained heating, convective heating, resistive heating, or any combination thereof). Thermal heating mechanisms may include raising the temperature of target tissue, such as neural fibers, chemosensitive cells, all or a substantial number of carotid body cells, and small blood vessels perfusing the carotid body or its nerves, above a desired threshold, for example, above a body temperature of about 37° C. e.g., to achieve thermal injury or damage, or above a temperature of about 45° C. (e.g., above about 60° C.) to achieve thermal necrosis for a duration of time known to induce substantially irreversible ablation at the resulting temperature.

In addition to raising temperature during thermal ablation, a length of exposure to thermal stimuli may be specified to affect an extent or degree of efficacy of the thermal ablation. In some embodiments the length of exposure to thermal stimuli is between about 1 and about 60 seconds, such as between about 5 and about 30 seconds. In some embodiments the length of exposure to thermal stimuli can be, longer than or equal to about 30 seconds, or even longer than or equal to about 2 minutes. Furthermore, the length of exposure can be less than or equal to about 10 minutes, though this should not be construed as the upper limit of the exposure period. A temperature threshold, or thermal dosage, may be determined as a function of the duration of exposure to thermal stimuli. Additionally or alternatively, the length of exposure may be determined as a function of the desired temperature threshold. These and other parameters may be specified or calculated to achieve and control desired thermal ablation. Thermally-induced ablation may be achieved via indirect generation or application of thermal energy to the target tissue, such as neural fibers, chemosensitive cells, and all or a substantial number of carotid body cells, such as through application of high-intensity focused ultrasound (HIFU), partially focused ultrasound, or high intensity directed ultrasound, to the target neural fibers.

Carotid body ablation may comprise delivering an agent systemically and directing energy such as ultrasound energy to the carotid body or associated nerves to activate the agent causing impairment of the carotid body or associated nerves.

Additional and alternative methods and apparatuses may be utilized to achieve ablation.

Directed Energy Embodiments

FIG. 1 depicts in simplified schematic form an alternative embodiment of a placement of an endovascular directed energy ablation catheter 13 into a patient 1 via an endovascular approach with a femoral vein puncture 17. The distal end of the endovascular directed energy ablation catheter 13 (shown in phantom) is depicted in the left internal jugular vein 12 (shown in phantom) at the level of the left carotid artery bifurcation 2 positioned for directed energy ablation of a carotid artery. As depicted the endovascular directed energy ablation catheter 13 is inserted into the patient at insertion site 17 in the vicinity of the groin into a femoral vein 16 and advanced through the inferior vena cava 15, superior vena cava 14, left common jugular vein 11 and into the left internal jugular vein 12. Alternatively, the insertion site may be selected to gain venous access through a brachial vein, a subclavian vein, a common jugular vein 11, or any suitable peripheral vein. Furthermore, the distal end of the endovascular directed energy ablation catheter 13 may be positioned for carotid body ablation in other than the internal jugular vein 12 or one of its tributaries (e.g., a facial vein, not shown) depending on the particular vascular and neural anatomy of patient 1. Also depicted is an optional angiographic catheter 97 positioned in the common carotid artery 3 for the purpose of creating an arterial angiographic image of the region of the carotid bifurcation 2 to allow for visualization of the region and for guiding directed energy ablation of the carotid body from the internal jugular vein 12. As depicted, angiographic catheter 97 is inserted into a femoral artery 8 through insertion site 9 in the groin, then advanced through the abdominal aorta 7, the aortic arch 6 and into the left common carotid artery 3 using standard angiographic techniques. It would be understood to those skilled in the art of endovascular interventions that means other than carotid artery angiography may be used to guide transvenous directed energy ablation of a carotid body. For example, extracorporeal ultrasonic imaging of the neck may be used, as well as intra-vascular ultrasound, computed tomography angiography, and other known modalities alone or in combination. It should also be understood that while FIG. 1 illustrates a left-side carotid body ablation, a right side carotid artery ablation or bilateral carotid artery ablations can be carried out in embodiments herein.

Sonography can be instrumental in guiding both percutaneous and endovascular procedures. Sonography can be performed from the surface of the skin, such as the neck, from inside the vasculature, from inside vasculature via imaging transducers positioned in or on an ablation catheter, or from a natural orifice such as the esophagus.

A directed energy device as used herein refers to an elongate device with an energy emitter configured to emit energy, and wherein the device is configured to deliver directed energy into target tissue. In some embodiments the device includes a therapeutic ultrasound transducer (also referred to herein as an energy emitter), which can be in a distal region of the device. In methods of use, the device can be positioned in a patient's body proximate to a carotid body or an associated nerve(s) of the patient. The therapeutic ultrasound transducer is then activated and acoustic energy capable of thermally ablating tissue is delivered to the target tissue, ablating the target tissue, such as a carotid body. Directed energy can be expected generally to penetrate tissue in a way that causes volumic heating of a volume of tissue in the direction in which the energy is emitted. It is expected that as the distance from the emitter increases, the directed energy is deposited, converted into heat and deformation of tissue, and thus attenuated. There is a boundary or distance beyond which the directed energy will not penetrate in a biologically significant way because of attenuation in tissue. Volumic heating of target tissue, which occurs when using therapeutic ultrasound ablation energy as described herein, is different than conductive heating of tissue, which requires heating from the contact point, through intervening tissue, and to the target tissue. There may be, however, some degree of conductive heating that accompanies volumic heating. With directed energy, however, it is intended that volumic heating is the primary means by which the target tissue is heated. Additionally, directed energy such as therapeutic ultrasound energy does not require intimate contact with the target to be effectively delivered. Ultrasound can be transmitted through blood with approximately ten times lower absorption than in the carotid body area, for example, allowing the energy to be delivered without intimate vessel wall (e.g., carotid artery or jugular vein) contact, or even without serious regard to the distance from emitter to that wall. This can be important where a vessel wall is irregular or vulnerable.

Ultrasonic acoustic energy is produced by an ultrasonic transducer by electrically exciting the ultrasonic emitter, which is disposed on or about the elongate device (e.g., a catheter). In some embodiments ultrasonic transducers may be energized to produce directed acoustic energy from the transducer surface in a range from about 10 MHz to about 30 MHz. The transducer can be energized at a duty cycle, such as in the range from about 10% to about 100%. Focused ultrasound may have much higher energy densities localized to a small focal volume, but will typically use shorter exposure times or duty cycles. In the case of heating the tissue, the transducer will usually be energized under conditions that cause a temperature rise in the tissue to a tissue temperature of greater than about 45 degrees C. In such instances, it can be desirable to cool the luminal surface in which the elongate device is positioned, in order to reduce the risk of injury.

Embodiments of ultrasonic transducers for placement in a patient's body for ultrasonic ablation of a carotid body are described herein. Such ultrasound transducers may be employed in any carotid body ultrasound ablation device described herein. For example, any of the ultrasonic transducers herein may be incorporated in a carotid body ablation catheter having a deployable or expandable structure (e.g., a balloon, cage, basket, mesh, or coil) to position, align, and maintain stable position of the transducer in a vessel such as an external carotid artery or internal jugular vein.

Figure 3A:
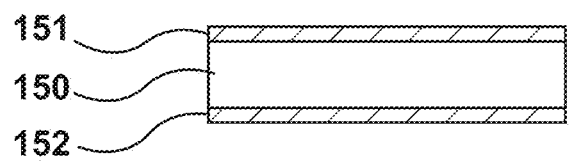
FIGS. 3A, 3B, 3C, 3D, and 3E are schematic illustrations of embodiments of an ultrasound transducer.

FIG. 3A illustrates an exemplary embodiment of an ultrasound transducer. As shown in FIG. 3A, an ultrasound transducer may be a non-focused, flat single element transducer, with two major surfaces approximately parallel to each other. The transducer aperture shape may be rectangular, or alternatively it may be round, oval or any other shape designed to fit an ablation device (e.g., catheter or probe). The width of the transducer aperture may be limited by the size (e.g., diameter) of the ablation device, for instance, to 2 F, 3 F, 4 F, 5 F, 6 F, 7 F, 8 F, 9 F, 10 F, 11 F. The length of the transducer aperture may be made larger than its width by increasing the length of the device distal assembly. The lengths of 4 to 6 mm have been proposed as a reasonable compromise between desired surface area and the ability of catheter to bend and navigate through anatomy. The surface of the rectangular essentially flat plate transducer can be made slightly convex in order to ensure convergence of the emitted ultrasonic energy beam.

It is generally desired to position the transducer with the emitter face surface pointing towards the target. The distal assembly containing the ultrasound transducer element of the ablation device may be guided in to place, for example in an external carotid artery, for instance, by using low intensity ultrasound Doppler guidance by the means of sensing blood flow in the internal carotid artery. The sample volume of the pulse wave Doppler along the ultrasound beam axis is adjustable in length and location. The location of the sample volume along the beam axis is preferably set to cover a range of about 2 to 15 mm (e.g., about 2 mm to 9 mm) from the transducer face. The ultrasound beam may be aligned with the aid of Doppler to cover a carotid body for ablation. Once the transducer is determined to be properly aligned, the carotid body and other desired target structures may be ablated using high intensity continuous wave, or high duty cycle (preferably greater than 30%) pulsed wave ultrasound. Pulsed ultrasound has advantage of cooling of the transducer and blood vessel by blood flow while the carotid septum more remote from the carotid blood flow continues to be heated. Ultrasound Doppler guidance and ultrasound ablation may be performed with the same transducer element, or alternatively with a separate transducer elements. Alternatively, the ultrasound transducer may consist of an annular array, for instance, a two-element array with a center disc for high intensity ablation and an outer ring for low intensity Doppler use.

The transducers herein may be configured to achieve thermal ablation with a maximum heating zone centered in tissue about 2 mm to 9 mm from the transducer face along the ultrasound beam axis. In some embodiments the transducer is configured to achieve thermal ablation with a maximum heating zone centered in tissue about 5 mm to about 8 mm from the transducer face. As set forth elsewhere herein, ablating in tissue this far from the transducer can allow for selective carotid body ablation while minimizing the risks associated with ablating other non-target tissue. Heating of tissue by endovascular ultrasound is affected by cooling by blood and by dissipation of mechanical energy of an ultrasonic beam in the tissue. The location of the maximum heating zone depends on the transducer design, specifically, the aperture size and frequency of operation, which defines the attenuation with distance and the shape of the ultrasound beam. In general, a higher frequency ultrasonic wave attenuates in a shorter distance as it travels though tissue and is absorbed. The maximum heating zone location may be fixed with a single element transducer. Alternatively, an ultrasound beam may be steered to a desired maximum heating zone location using phased array technology, acoustic lenses or geometrically focused transducers. The device may be designed to achieve a volume of ablated tissue of about 8 to 300 $mm^3$ (e.g., about 154+/−146 $mm^3$). The combination of delivered energy, shape, direction of the ultrasound beam, and application time sequence may determine the volume of ablated tissue. Energy delivery, e.g., power settings and mode of operation (e.g., pulsed wave vs. continuous application time sequence), may be used to enhance heating in a target location or zone and achieve repeatable target tissue temperature over time. In an example embodiment, for a transducer having a width of about 2 mm and length of about 4 mm, an ultrasound frequency of operation may be chosen to be about 10 to about 30 MHz, (e.g., 15 to 25 MHz). In some embodiments the ultrasound is delivered at a frequency of between about 10-25 MHz. In some embodiments the ultrasound is delivered at a frequency of between about 10-20 MHz. In some embodiments the ultrasound is delivered at a frequency of between about 10-15 MHz. In some embodiments the ultrasound is delivered at a frequency of between about 15-30 MHz. In some embodiments the ultrasound is delivered at a frequency of between about 15-25 MHz. In some embodiments the ultrasound is delivered at a frequency of between about 15-20 MHz. In some embodiments the ultrasound is delivered at a frequency of between about 20-30 MHz. In some embodiments the ultrasound is delivered at a frequency of between about 20-25 MHz. In some embodiments the ultrasound is delivered at a frequency of between about 25-30 MHz.

The ultrasound transducer may be operated in the thickness resonance mode, i.e., the frequency of operation is substantially determined by the half wavelength thickness of the piezoelectric transducer element. The transducer element may be made of PZT-4 (Navy I) or PZT-8 (Navy III) type piezoceramic material or equivalent that exhibits low losses under high power driving conditions and may be incorporated in a piezocomposite structure. High intensity, high duty cycle, mode of operation may result in self-heating of the transducer element and surrounding structural elements. Therefore, the temperature of transducer or adjacent elements may be monitored with a temperature sensor (e.g., a thermocouple). If temperature is deemed to be too high, the transducer may be cooled down during use by a means of reducing duty cycle, or electrical power output into the transducer, or irrigation or circulating fluid cooling. Alternatively, transducer efficiency may be enhanced to reduce transducer self-heating by a means of electrical and acoustic impedance matching. For instance, the capacitive reactance of electrical transducer impedance may be cancelled or reduced by a means of inductive tuning. If the transducers perform imaging or Doppler sensing function the acoustic impedance, defined as a product of speed of sound and density, of commonly used piezoelectric materials is much higher than acoustic impedance of soft tissue (e.g., about 20×). Therefore, coupling of acoustic energy from the transducer element to soft tissue is poor. A means of improving coupling of acoustic energy may be to use a matching layer, or multiple matching layers, of about quarter wavelength thickness at the frequency of operation, on the transducer face between the transducer element and tissue. Theoretically, the acoustic impedance of a matching layer should be close to the geometric mean of that of the source, piezoelectric transducer element (about 30 MRayl), and load, soft tissue (about 1.5 MRayl). It is understood that some methods of improving acoustic efficiency may be relevant more to high-energy delivery and some more to imaging and Doppler sensing.

In some embodiments the effectiveness of a therapeutic high energy mode transducer operating in continuous mode at or near resonance frequency can be optimized by including a matching layer made of material with acoustical impedance lower than the acoustical impedance of soft tissue or water (about 1.5 MRyal) divided by a transducer mechanical quality factor (between 0 and 100 measured in water). A common means of improving power transfer between water and acoustically hard ceramic by insertion of a quarter wavelength matching layer is not applicable in the case of a planar transducer undergoing large displacement at resonance. A thin therapeutic matching layer can be constructed, for example, by bonding a thin layer of polyester, polyurethane, or polyimide polymer directly to an emitting surface of the ceramic transducer. Alternatively, a therapeutic matching layer can be constructed of polyvinylidene fluoride (PVDF), which may be used as an imaging element or multi-element imaging array directly attached to the surface of a therapeutic transducer. PVDF is a piezoelectric polymer with low acoustic impedance well suitable for ultrasound imaging. Deposition of PVDF on the emitting surface of a high impedance, hard, therapeutic ceramic may help to miniaturize the design and optimize power transmission in therapeutic mode and obtain an ultrasound imaging function in the same stack of transducer.

FIG. 3A shows an exemplary piezoelectric transducer element 150 with a top (or front) electrode 151 and bottom (or back) electrode 152. The transducer element 150 may be made of PZT-4 (Navy I) or PZT-8 (Navy III) type piezoceramic material. PZT-4 and PZT-8 type materials are known as "hard PZT", which have a relative high mechanical quality factor (e.g., about 500 to about 1000) and high Curie temperature (e.g., greater than 300° C.), and are therefore well suited for high intensity and high duty cycle use. The top 151 and bottom 152 electrode of the transducer element may be solderable to provide reliable electrical connections to transducer surfaces. The electrode with negative polarity is preferably on the outer radiation surface of the transducer, facing the tissue target. In this embodiment that is the top electrode 151.

Figure 3B:
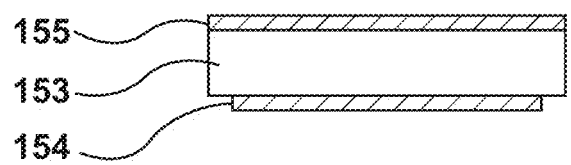

FIG. 3B shows an exemplary piezoelectric transducer element 153 with an undersized electrode 154 on the backside of the element. The purpose of the undersized electrode is to avoid the possibility of unwanted electrical connections (i.e., short circuit) to the transducer housing assembly. The top (or front) electrode 155 may cover approximately the full face of the transducer element 153.

Figure 3C:
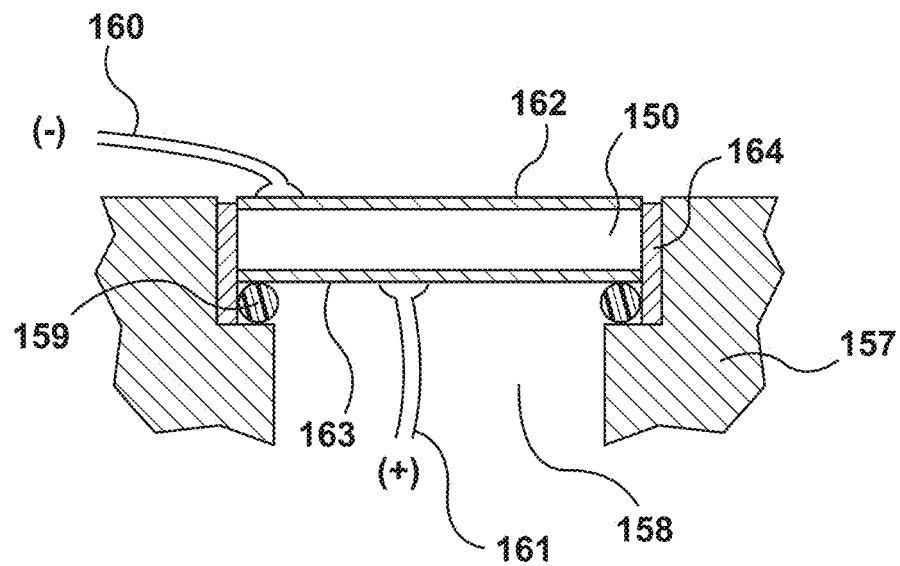

FIG. 3C shows an example of mounting of a transducer element 150 into a housing assembly 157 of which only a partial view is shown for illustration purposes. The transducer element 150 may be located approximately at or close to the axis of a shaft of an ablation device (e.g., catheter or probe) to allow a maximum transducer width. The transducer element 150 rests over a backing cavity 158 on an acoustic insulator 159, for instance an O-ring or frame made of soft compliant material. The purpose of the insulator is to isolate the acoustic vibration of the transducer element from the housing assembly. The sides of the transducer element 150 may be sealed with filler 164 that provides hermetic sealing. At the backside of the transducer element a backing cavity 158 may be filled with gaseous or foamy material of low acoustic impedance. Low acoustic impedance may be defined as a product speed of sound and density of material. The backing cavity is hermitically sealed from the environment (not shown) to prevent any liquid from coming in contact with the backside of the transducer element 150. Electrical connections may comprise negative polarity 160 connected to the front transducer electrode 162, and positive polarity 161 connected to the back transducer electrode 163. Electrical connections may be soldered or welded for example.

Alternatively a material with high acoustic impedance can be used to prevent spreading of energy in the direction other than target. Backing can be made of dense and high sound speed materials such as metals, for example stainless steel, that reflect acoustic energy. Generally transition or interface between materials with significantly different acoustic properties (e.g., speed of sound) will reflect acoustic energy.

Figure 3D:
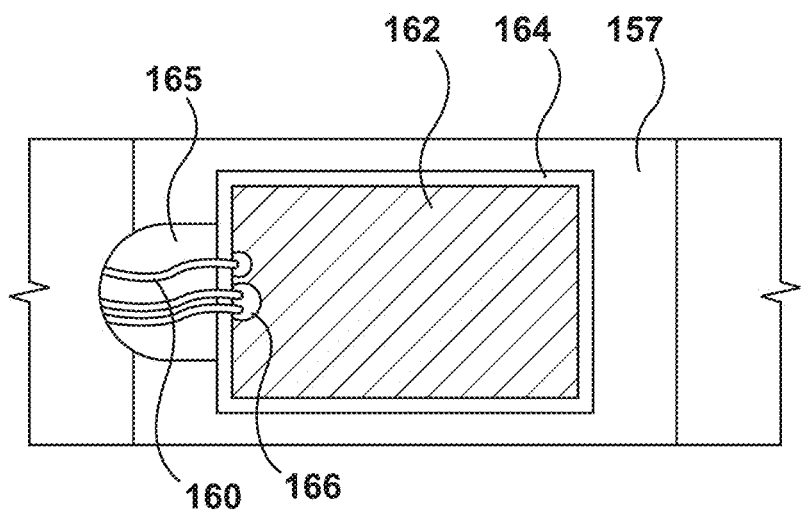

FIG. 3D shows a top view, or front face, of a transducer distal assembly. A wire lumen 165 may provide a path for electrical wiring to the transducer that at the proximal end of the device is connected to a controller that may contain a pulse wave Doppler circuitry and a RF signal source for ablation. The same wire lumen 165 may be used for thermocouple wires connected to a thermocouple 166 positioned on the transducer element or distal assembly of the device.

Figure 3E:
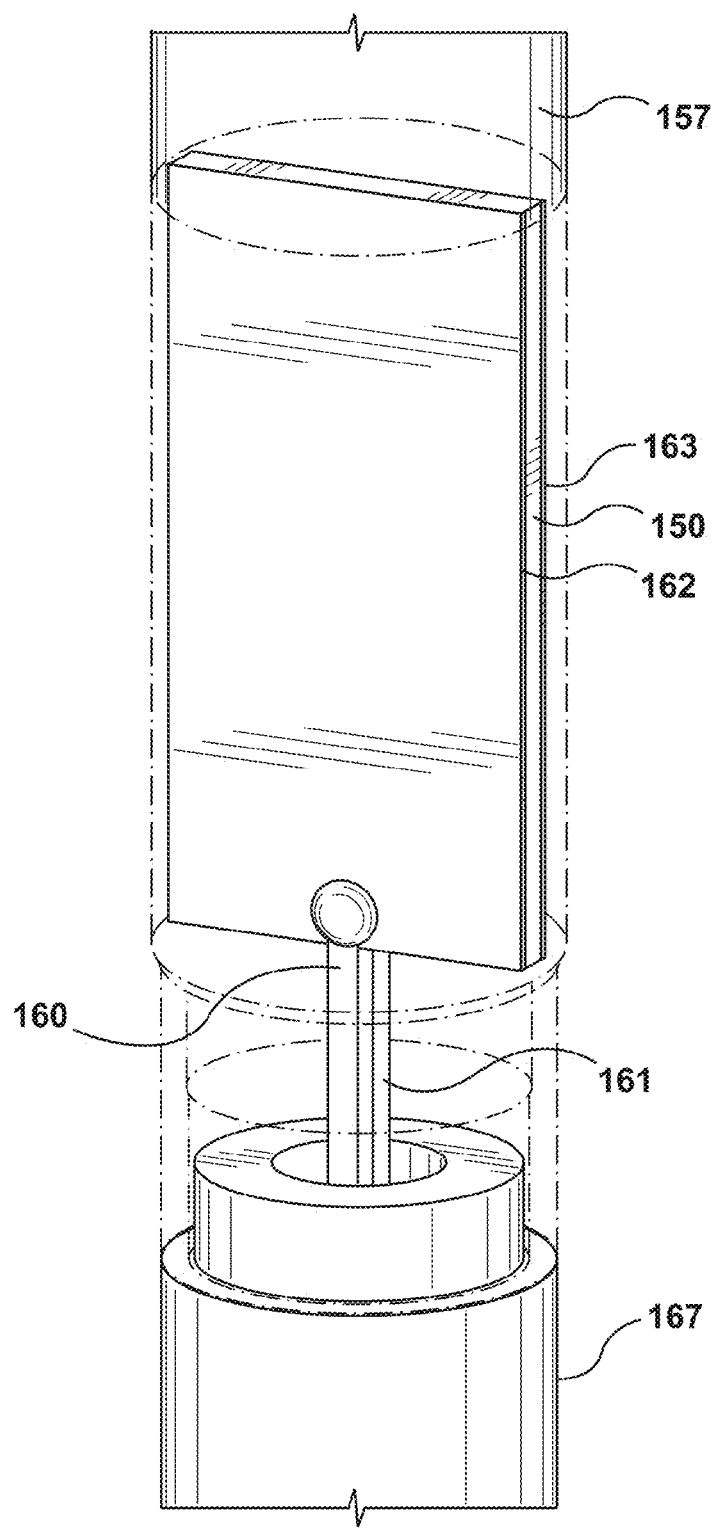

FIG. 3E shows an embodiment of a distal portion of an ultrasound ablation catheter comprising a rectangular ultrasound transducer 150 (as shown in FIGS. 3A, 3C, and 3D) positioned at or near an axis of the catheter shaft 167. The catheter may be configured to be controllably deflectable by applying tension to pull wires with an actuator in a handle. The pull wires may run through the shaft and be anchored near the distal portion of the catheter.

Ultrasound Carotid Body Ablation from an Endovascular Catheter Positioned in a Vein The disclosure herein includes embodiments in which an endovascular ultrasound ablation catheter is delivered to an internal jugular vein or one of its tributaries to direct ablative energy to a carotid septum. Trans-venous instruments can have an advantage over trans-arterial ones in that they have a lower risk of brain embolization. Additionally, a larger instrument can be used in trans-venous approaches.

One aspect of the disclosure is a method of carotid body ablation that includes introducing an elongate device such as a catheter into the venous system of the patient, advancing a distal end of the catheter into an internal jugular vein or one of its tributaries proximate to a carotid septum, wherein the distal region includes a directional emitter of high-energy ultrasound capable of delivering ablative acoustic energy, aligning the emitter with the carotid septum, and directing energy into the septum to ablate the target tissue (e.g., carotid body, tissue in the carotid septum, carotid body nerves).

Figure 4A:
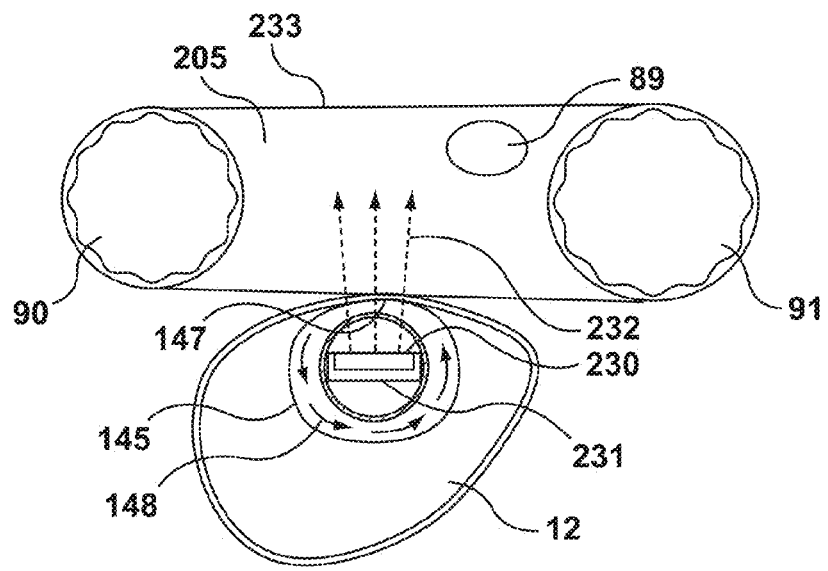
FIGS. 4A and 4B are schematic illustrations of an ultrasound CBA catheter delivered to an internal jugular vein.
Figure 4B:
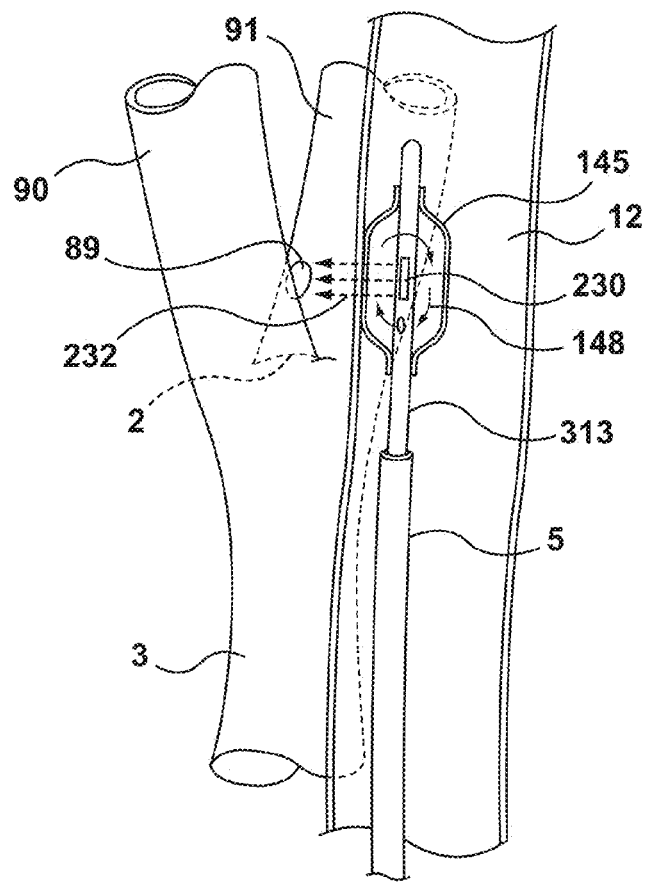

FIGS. 4A and 4B illustrate an exemplary embodiment of a trans jugular ultrasound ablation catheter. As can be seen FIG. 4A, the proximity of a jugular vein to a carotid septum and carotid body provides an opportunity to ablate the carotid body with a device positioned in a jugular vein. Catheter 313, as shown in FIGS. 4A and 4B, includes an ultrasonic emitter 230 and optional receiver. The emitter is capable of delivering high-energy ultrasound in a selected direction (e.g., directed high energy unfocused ultrasound beam). Reflective backing 231 (e.g., an acoustic insulator made from, for example, air, foam, or dense metal) reflects ultrasound waves 232 or ensures they are mostly directed in the desired direction. Frequency, power, duration and aperture are calculated or experimentally determined, considerations of which are described in detail above, to ablate tissue within a carotid septum 205 but to prevent ablative energy from penetrating through and beyond the septum, for example beyond a medial boundary 233 of the carotid septum. For example, the emitter can be configured so that ablation energy delivered may be deposited no more than about 12 mm, 11 mm, 10 mm, 9 mm, 8 mm, 7 mm, 6 mm, 5 mm, 4 mm, or 3 mm into tissue from emitter 230. In some embodiments the emitter is configured such that the high energy ablation ultrasound will lose ablation power after penetrating about 3 mm to about 12 mm into soft tissue, such as about 3 mm into soft tissue, about 4 mm into soft tissue, about 5 mm into soft tissue, about 6 mm into soft tissue, about 7 mm into soft tissue, about 8 mm into soft tissue, about 9 mm into soft tissue, about 10 mm into soft tissue, about 11 mm into soft tissue, or about 12 mm into soft tissue. There may be some patient to patient variability in the size of a septum, and thus it may be beneficial to obtain visualization of the septum prior to ablation, obtain an estimated size of the septum, and use delivery parameters based on the estimated size.

Excitation frequencies in the range of about 10 to about 30 MHz, such as between about 10 MHz to about 20 MHz, can be expected to produce the desired effect, including sufficient depth of penetration of ablative energy and at the same time containment of the desired ablation zone. Cooling from blood flow within internal 90 and external 91 carotid arteries may assist containment of the ablative thermal energy, or ablation zone, in a carotid septum. Thus a heat distribution from an ablative ultrasound beam may be shaped additionally by inhomogeneous heat conduction of the area influenced by cooling blood flow and enhancing ultrasound induced heating related bio-effects in the target space between the internal carotid artery 90 and external carotid artery 91 (i.e. carotid septum 205). Due to high blood flow and consequent effective thermal cooling of blood vessels, ultrasound energy in the selected frequency range travels through the vessel walls and blood without significant biologic effects and therefore only the septum will be selectively heated. One aspect of this disclosure is a method of delivering high intensity ablative ultrasound towards the carotid septum while utilizing the cooling effects of the blood in the internal and external carotid arteries to selectively ablate only septal tissue. Some attenuation through scattering can be expected to reduce the posterior ultrasound effects and protect non-target structures behind the arteries. This principle can be classified as forming of a lesion using thermal heating by an ultrasound beam that is shaped in the tri-vessel space. In some embodiments the emitted ultrasound energy ablates septal tissue by increasing the temperature of the septal tissue to greater than about 45 degrees C., yet tissue outside of the septum remains less than about 45 degrees C. and is thus not ablated. Ablation is a function of temperature and time, and longer exposure to lower energy and temperature can also ablate tissue. This disclosure focuses mainly on temperature and includes treatments that last about 5 to about 60 seconds. The temperatures mentioned herein however shall not be interpreted as strict limitations.

Choice of ultrasound therapeutic parameters such as power, frequency, time and regime (e.g., pulsed or continuous) may ensure that an ultrasound beam does not ablate tissues deeper than about 15 mm (e.g., no deeper than about 9 mm) from the jugular vein. For the typical attenuation of ultrasound in muscle tissue of 1 dB/cm/MHz, the characteristic depth of unfocused ultrasound penetration in tissue is the inverse of attenuation coefficient divided by frequency. For example, at 10 MHz the characteristic penetration depth is 7.7 mm and at 20 MHz the characteristic penetration depth is 3.8 mm, which roughly corresponds to a one example of a range of target distances in a trans jugular catheter configuration.

FIG. 4B illustrates catheter 313 introduced from below (e.g., via femoral vein access). An endovascular approach from below may comprise puncture of a femoral vein in the groin of the patient and threading the catheter through vena cava into a desired jugular vein, such as is shown in FIG. 1. Other alternative approaches such as from a jugular veins and branches of jugular vein and other veins of the body such as a subclavian vein are also possible and may have advantages in some clinical situations.

Directing the beam from a jugular vein 12 into the septum between two carotid branches benefits the shaping of the lesion by cooling effects from carotid arteries. As illustrated by FIG. 4A the energy beam 232 is constrained between two carotid artery branches that are protected from thermal damage by high flow of blood. The anatomy in this region therefore provides an intrinsic advantage in that if the beam is slightly misaligned and points at a slightly wrong angle, it will encounter the internal or external carotid artery, which will resist heating of immediately surrounding tissue by its cooling effect. The beam, or portion of the beam directed between the brunches, will be subject to less cooling and will result in ablation of tissue where the target organs, such as carotid body 89 and associated nerves, are expected to reside (i.e., in a carotid septum). As a result, the carotid septum is selectively heated and thermally ablated, which is one of the aspects of this disclosure. As set forth above, this disclosure also includes methods of selectively ablating target tissue by delivering high intensity ultrasound energy into a region of the anatomy so that blood flow will provide a cooling effect and therefore facilitate the containment of the ablated tissue to a desired region. In the case in this embodiment, the ablated tissue is contained in the carotid septum.

Directing and targeting an ultrasound ablation beam 232 at a target site such as a carotid septum 205 from within a jugular vein may be facilitated by detecting vasculature such as the common carotid artery 3, internal carotid artery 90 and external carotid artery 91, and carotid bifurcation 2 using diagnostic ultrasound such as Doppler ultrasound. Such diagnostic ultrasound may provide an indication (e.g., visual images, acoustic, or electrical signals) of the vasculature by detecting blood velocity, direction of flow, pulsations of flow and turbulence while manipulating a catheter (e.g., rotational and translational manipulation) that comprises at least one ultrasound transducer.

In some embodiments translational aiming (in some instances being aligned with) may be achieved by detecting a carotid bifurcation saddle 2 and aiming an ultrasound treatment transducer (also referred to herein as an ultrasound ablation transducer or ultrasound ablation emitter) with a target site relative to the carotid bifurcation saddle. In some embodiments the ultrasound treatment transducer is aimed about 5 to about 15 mm cranial to the bifurcation, saddle in some embodiments about 10 to about 15 mm cranial to the bifurcation saddle, in some embodiments about 10 mm to about 12 mm cranial to the bifurcation saddle, and in some embodiments about 5 to about 10 mm cranial to the bifurcation saddle. A carotid bifurcation saddle can be detected from a position along the length of a jugular vein 12 as a location where one strong blood velocity signal representing a common carotid artery 3 separates abruptly into two arteries, the internal 90 and external 91 carotid arteries. An ultrasound ablation beam may be aimed at a location about 5 to about 15 mm above the level of the bifurcation saddle by advancing or retracting the catheter. Aiming the beam at a location about 5 to about 15 mm caudal to the bifurcation saddle aims the beam into the carotid septum to facilitate ablating the carotid body.

In some embodiments a method of ablation includes detecting one or both of the internal and external carotid arteries. They can be detected by rotating a diagnostic transducer, which can occur with a catheter or balloon, or within the catheter or balloon. The treatment transducer can then be aimed at a target site relative to the internal and external carotid arteries. In some embodiments the external and internal carotid arteries are detected, and the treatment transducer is rotationally aimed approximately between the internal and external carotid arteries. In this orientation relative the two arteries, the ultrasound treatment transducer is aimed to ablate the septal tissue and thus the carotid body. In other embodiments aiming the beam is aided by other visualization techniques, such as MRI, CTA, or Fluroscopy. An ultrasound transducer may optionally also be capable of delivering and receiving low power ultrasound that can be used for imaging of carotid arteries, Doppler imaging, or pulse Doppler imaging. Examples of transducers configured in this regard are described herein. Doppler signal feedback to an operator or computer controlling energy delivery need not be necessarily an image. It can be an indicator such as a curve, a number, an acoustic signal, an LED bar, or an indicator light color or intensity.

Alternatively or additionally, ultrasound imaging may be applied from an external transducer placed on skin of a patient's neck and used to guide therapy. Externally applied ultrasound imaging may incorporate biplane imaging and Doppler flow enhanced imaging. Alternatively, additional ultrasound emitters and receivers can be incorporated in the catheter design.

Alternatively or additionally, single or multiple ultrasound transducers may be positioned on the distal section of a trans jugular catheter such that ultrasound reverberation between the exterior of the neck surface and ultrasound transducers is sensed in electrical impedance or by means of ultrasonic imaging thus allowing alignment of the catheter with respect to the lateral landmarks of the neck effectively pointing the therapeutic transducer in a medial direction toward the intercarotid septum. The lateral reflections provide acoustic guidance to the catheter ultrasound transducers with the effect maximized when catheter ultrasound imaging transducer becomes substantially coplanar with the exterior neck surface, which may coincide with a desired rotational position relative to the bifurcation of the carotid arteries. Alternatively, similar lateral guidance may be achieved by placing a substantially flat echogenic reflector or active low power ultrasound transducer on the surface of the neck.

In some embodiments herein the ablation catheter may be advanced into an internal jugular vein from the groin, from a subclavian, from a brachial vein, or by direct puncture using methods somewhat similar to ones used for biopsy or central access catheter placement. In some cases a facial vein, or other vein branching from an internal jugular vein, may provide a closer proximity to a carotid septum for placement of an energy delivery element of the catheter. The jugular vein as a venous position for the catheter is therefore merely illustrative.

As described in methods herein, a catheter may be advanced up and down the jugular vein until a bifurcation of a common carotid artery and carotid septum just above it are clearly detected. If external ultrasound is used, the catheter may be made visible with ultrasound by addition of an echogenic coating. This can be confirmed by a Doppler pulsatile velocity signal or ultrasonic imaging. A space, indicating a carotid septum, between two large vessels with high pulsatile blood flow should be easily detectable. Pulsed Doppler at the preselected depth of 3 to 10 mm (e.g., 3 to 5 mm) can be chosen to avoid interference from venous blood flow.

In some embodiments a catheter positioned in a jugular vein may be rotated around its axis until the ablation, or treatment, transducer aperture is facing the carotid septum pointing into the gap between internal and external arteries. Alternatively a transducer with a directional emitter can be rotated inside the catheter. If the Doppler emitter and receiver are located in the distal portion of the catheter placed in a jugular vein, certain advantages may be realized. A low energy Doppler beam can be facing the same direction as the high energy ablation beam. A Doppler signal can then be used for targeting and directing the ablation beam into the septum. The septum can be located as a valley of low velocity area between two peaks or high velocity areas. Alternatively, several Doppler transducers can be incorporated in the distal tip aiming beams silently at an angle to the direction of the face of the aperture of the high energy beam in order to detect both carotid arteries by their high velocity flow. A vein may be distended and a catheter tip maneuvered into position so that a high-energy emitter is aiming into the middle of the gap between two strong Doppler signals representing an internal and external carotid artery. A computer algorithm may assist or automate such aiming.

During ablation the ultrasonic energy emitter may get hot and may require cooling. The catheter may be configured to position the transducer in an internal jugular vein so it does not touch the wall of the jugular vein while delivering high energy for the purpose of ablation. For example, the catheter may comprise a protective membrane such as balloon 145, as shown in FIGS. 4A and 4B. The balloon 145 separates the transducer 146 from the vessel wall 147 while providing a conduit for an energy beam and cooling of the transducer, the blood in the vein 12, and the tissue of the wall of the jugular vein. The balloon 145 may be made of a thin polymer film that can be compliant or not complaint but is capable of sustaining some pressure, providing firm contact with the wall of the vessel and conducting ultrasound in the selected frequency range without significant attenuation, reflection or heating. The balloon may be filled with a circulating fluid 148, such as sterile water or saline, which is biocompatible and conducts ultrasound well without absorbing significant energy. The fluid may be externally chilled, recirculated by an external pump (not shown) through the catheter shaft, or can be just infused and released into the bloodstream in relatively small quantities sufficient to keep the fluid and the emitter submerged in fluid at a desired low temperature.

Figure 9A:
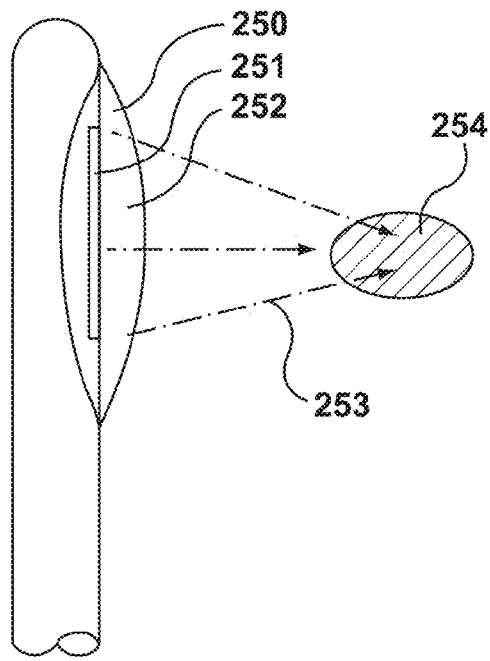
FIGS. 9A and 9B are schematic illustrations of an ultrasound CBA catheter with an adjustable focus distance.
Figure 9B:
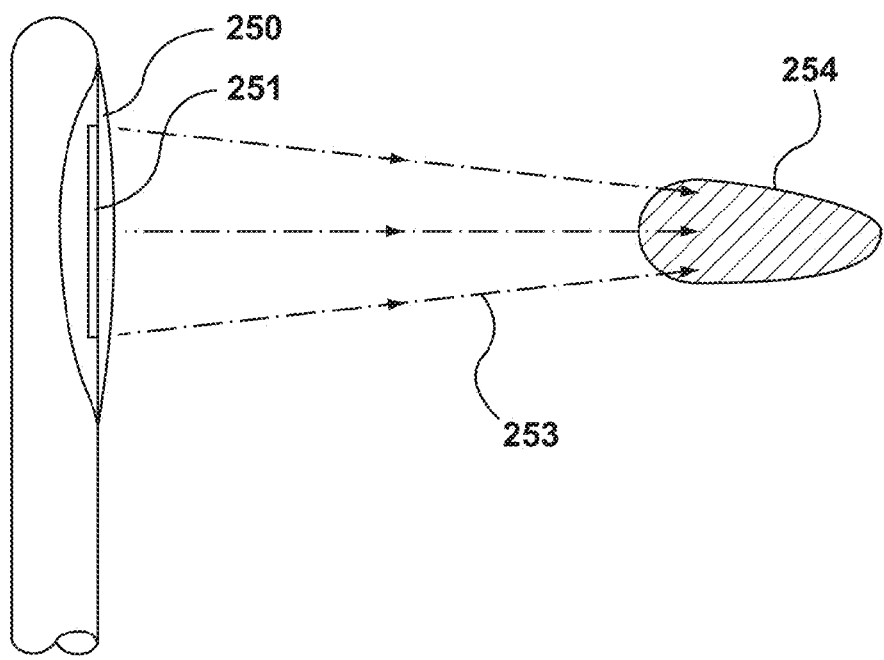

A protective membrane may fully encompass the distal end of the catheter forming a balloon around ultrasound transducers or, as shown in FIGS. 9A and 9B, a protective membrane 250 may partially encompass a selected ultrasound transducer 251. The protective membrane can be formed around a therapeutic transducer in a shape of a convex, concave, or Fresnel acoustic lens and filled with liquid coolant fluid 252 such as Fluorinert with acoustic properties substantially different from that of blood. An ultrasonic beam may be shaped by a protective membrane lens to a predefined focused or defocused pattern in order to obtain selected regional sensitivity in Doppler imaging or a delivered therapeutic dose in the ablation area. Alternatively a transducer with a predefined thin-wall expandable protective membrane may form a directional emitter that can be manipulated to form a directional beam that can be targeted to different depths. The target depth of Doppler emitters and receivers may be configured to enable ultrasound beam shaping and focusing advantages realized when facing substantially different anatomy in the jugular vein and carotid complex.

The ablation depth control may be achieved by placing a catheter in a jugular vein and manipulating the lens internal fluid pressure to expand the protective membrane in a predefined repeatable shape that produces an acoustic convergent or divergent lens effect to the ultrasound beam and preferentially targets the ultrasound beam into a specific target depth in the bifurcation of a carotid artery and a carotid septum. For example, as shown in FIG. 9A a membrane 250 is inflated with coolant 252 creating a lens shape that focuses an ultrasound beam 253 on a target region 254. Comparatively as shown in FIG. 9B the membrane 250 may be inflated with coolant 252 at a different pressure to alter the lens shape to focus the ultrasound beam 253 on a target region at a different distance. The expandable membrane can be formed from a variety of compliant polymer materials such as Kraton (styrene blend), polyethylene, polypropylene, Pebax, or Latex. Alternatively, an expandable membrane may be used to control the positioning of the catheter inside the jugular vein with respect to the distance to the carotid complex.

Figure 10:
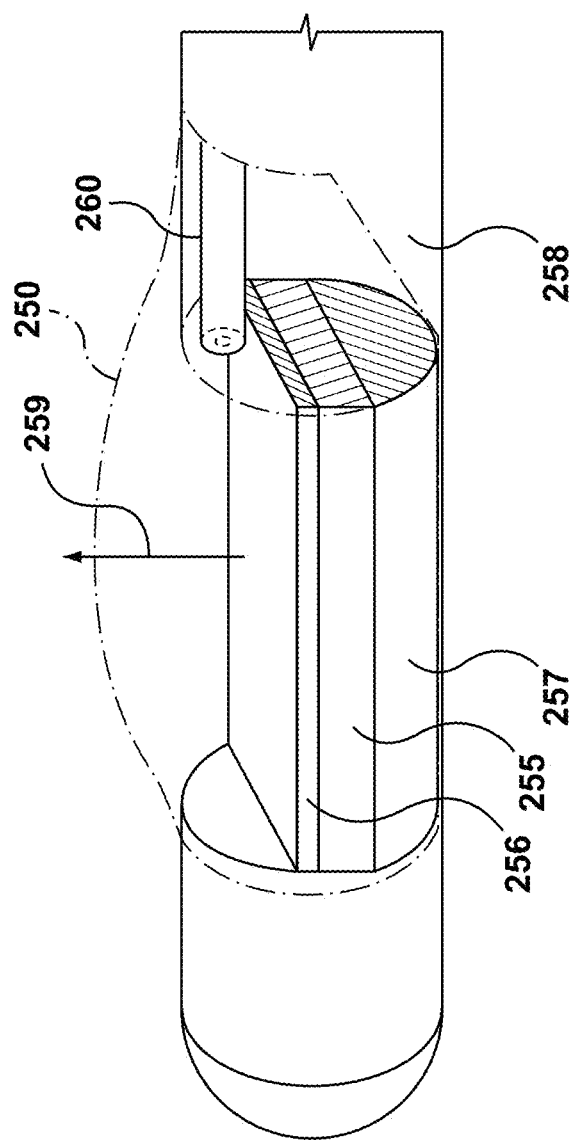
FIG. 10 is a schematic illustration of an ultrasound CBA catheter with an adjustable focus distance.

A distal end of an embodiment of a carotid body ablation catheter, shown in FIG. 10, comprises an ultrasound transducer 255 and a PVDF imaging array 256 positioned near a distal end of a catheter shaft 258. An acoustic insulator 257 such as stainless steel may be positioned on a backside of the transducer 255 to ensure an imaging or ablation beam is directed in a direction 259 orthogonal to the front surface of the transducer 255. An expandable membrane 250 encompasses a cavity in front of the transducer. Liquid, such as a coolant, may be injected into the membrane cavity through an inflation lumen or tube 260 to inflate the membrane 250 to a desired shape, which may focus or direct the ultrasound beam.

In alternative embodiments, any of the catheters comprising an ultrasound ablation transducer and an expandable membrane, such as those in FIG. 9A, 9B, or 10, can also include any of the diagnostic transducers described herein, such as those shown in FIGS. 5A-B, 6A-B, 7A-C mounted to the catheter, which may be used to assist in positioning the ablation transducer and aligning it with respect to one or more vascular landmarks, such as a carotid bifurcation, internal carotid artery, external carotid artery, or combination thereof, to direct an ablation ultrasound beam toward a target tissue volume, such as a carotid septum or position within a carotid septum.

An ablation catheter may comprise an ultrasound ablation transducer and an expandable membrane, such as membrane 250 shown in FIG. 9A, 9B, or 10, wherein the ultrasound ablation transducer may also be used for diagnostic ultrasound such as Doppler. These catheters may be positioned in an external carotid artery and rotated while assessing a diagnostic signal, which may be used to find vessels such as an internal carotid artery or internal jugular vein. The transducer may be placed at a desired distance cranial from a carotid bifurcation in an external carotid artery, for example about 5 to about 15 mm, or about 5 to about 10 mm, with the help of fluoroscopic imaging. For example, the catheter may have a radiopaque marker positioned the desired distance (e.g., about 5 mm to about 15 mm, or about 5 mm to about 10 mm) proximal to the transducer; contrast may be delivered to a common carotid artery (e.g., from a delivery sheath), a radiographic image may be taken of the carotid arteries and the distal portion of the catheter, and the radiopaque marker may be aligned with the carotid bifurcation. When the diagnostic transducer is aimed at an internal carotid artery or approximately the center of an internal carotid artery and the transducer is positioned a desired distance cranial from the carotid bifurcation it may be expected that the transducer is aimed through a carotid septum. An ablation ultrasound beam may be directed into the target tissue in the carotid septum. Optionally, the catheter may further comprise a deflectable section proximal to the transducer (e.g., between about 5 mm and about 30 mm proximal to the transducer) that may be used to direct the angle of the ultrasound beam with respect to the external carotid artery, which may be useful to adjust for a variety of carotid vasculature geometries such as narrow or wide bifurcation angles. Optionally, the catheter may further comprise a deployable structure such as a balloon, cage, mesh or helix positioned on the catheter distal to the transducer, which may be used to engage and stabilize the distal portion of the catheter in an external carotid artery. The deployable structure may deploy to a size suitable to engage in an external carotid artery, for example having a diameter of about 4 to about 6 mm. The deployable structure may retract so it can fit in a delivery sheath, for example having a diameter of less than about 3 mm (e.g., between about 2 mm and about 2.4 mm).

The disclosure herein also includes methods, devices, and systems for ablating a target site by positioning an ablation needle within a lumen of a vein adjacent to the target site, inserting the needle through the vein and into perivascular space containing the target site, delivering an ablation agent into the perivascular space by using the needle, and withdrawing the needle from the perivascular space back into the vein. There may be potential benefits for positioning a device via a trans-venous approach for a carotid body ablation procedure compared to a trans-arterial approach. For example, jugular veins have thinner walls compared to carotid arteries which may be easier to pass an ablation needle through; jugular veins are distensible and flexible and a change in conformation may be achieved by applying force from inside or outside the vessel which may be advantageous for facilitating position of a catheter or accessing a target ablation site; jugular veins have no atherosclerotic or arteriosclerotic disease and blood flows away from the brain eliminating a risk of causing a brain embolism, which may be a concern with a procedure in carotid arteries; a trans jugular approach may access an intercarotid septum from a lateral side; perforation with a needle or catheter through a wall of a vein (e.g., jugular, facial veins) has less risk of complications such as hematoma due to compressibility of the venous vessel compared to carotid arteries; possible reduction of blood flow in a jugular vein has less risk of flow limitation to the brain compared to reduction of flow in an internal carotid artery.

Figure 2:
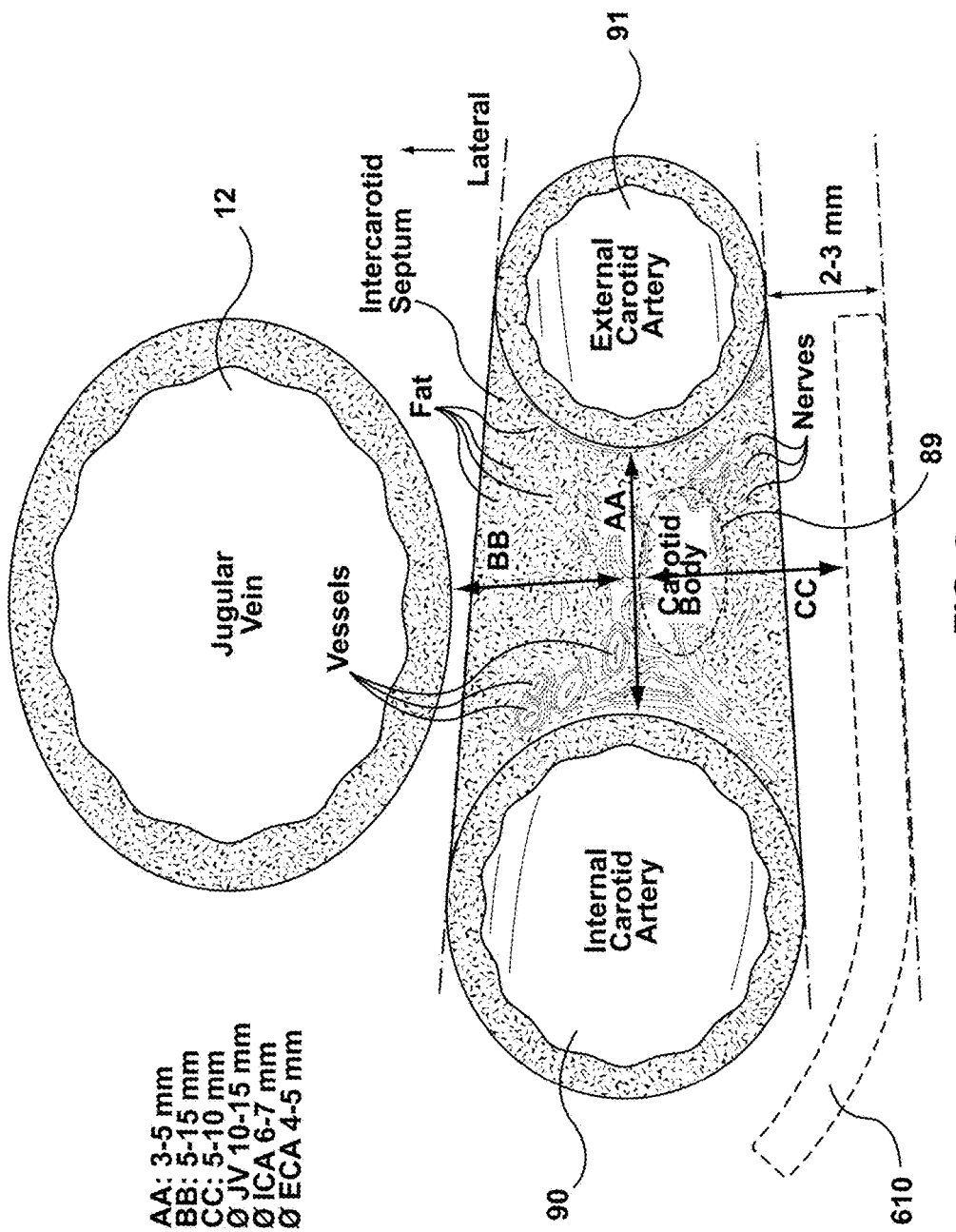
FIG. 2 is a schematic illustration of a cross section through an intercarotid septum and surrounding tissues showing some characteristic dimensions.

A representative exemplary anatomy with exemplary characteristic dimensions is shown in the FIG. 2 including AA—distance between the carotid arteries (e.g., in a range of about 3 to 5 mm), BB—distance between the jugular vein and center of a carotid septum (e.g., in a range of about 5 to 15 mm), CC—distance between a center of a carotid septum and important non-target structures on a medial side of the carotid septum (e.g., in a range of about 5 to 10 mm). Embodiments described herein may be configured to safely and effectively deliver ablative energy to a target tissue such as the carotid body or carotid septum from a proximate vein such as a jugular vein or facial vein.

Ultrasound Ablation Catheters with Imaging Transducers

Figure 6B:
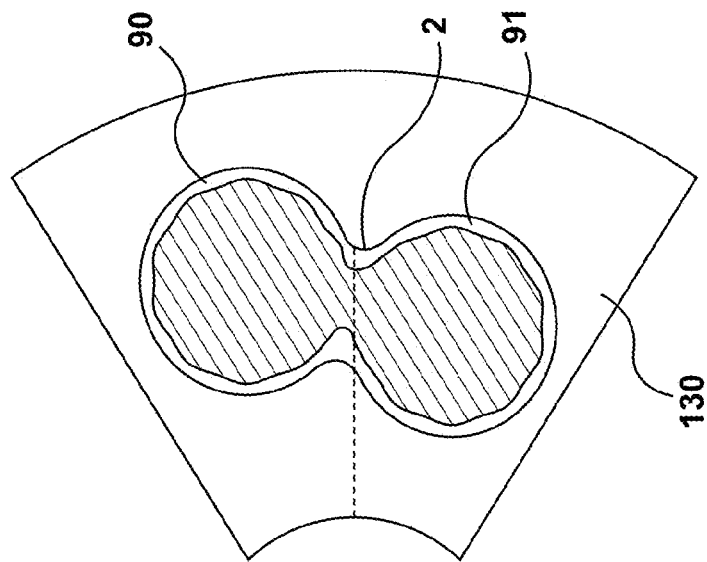
Figure 6A:
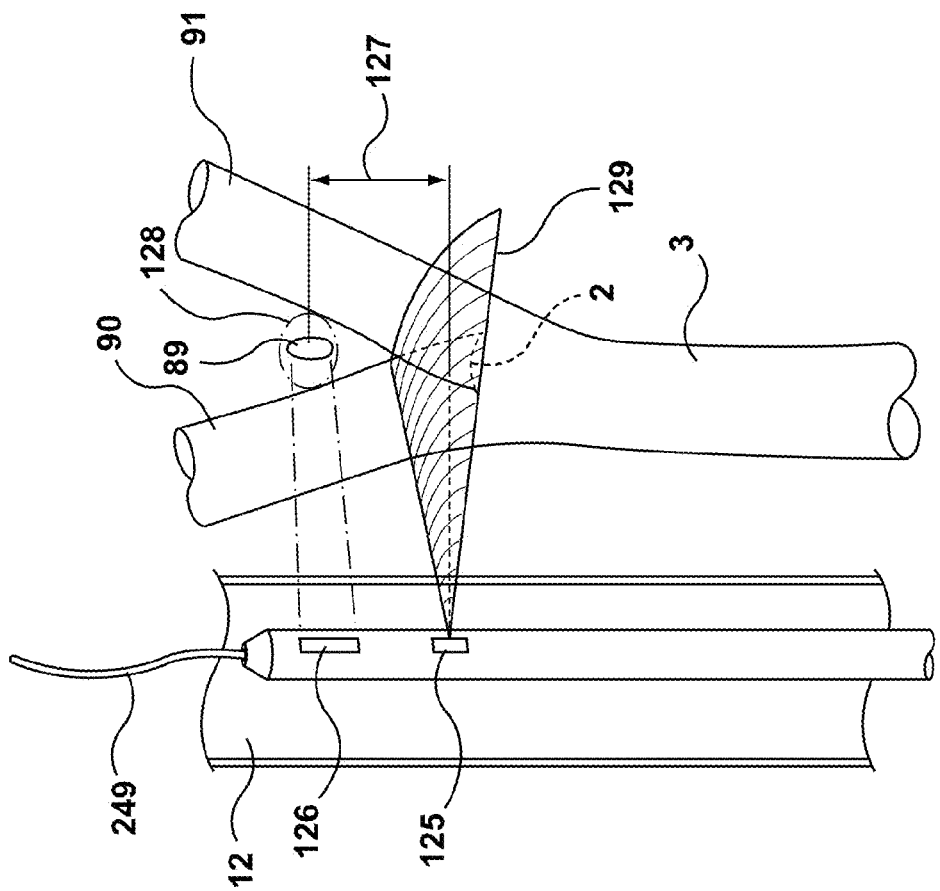

In some embodiments an ultrasound carotid body ablation catheter comprises at least one diagnostic ultrasound transducer and an ultrasound treatment transducer, wherein the transducers are positioned on the catheter relative to one another such that when the diagnostic ultrasound transducers are aligned with vasculature landmarks, the treatment transducer is aligned with a target ablation site (e.g., carotid septum). Carotid vascular landmark as used herein includes an internal carotid artery, an external carotid artery, a carotid bifurcation, and a common carotid artery. This configuration allows an alignment of a diagnostic transducer and a landmark to indicate an alignment of a treatment transducer and target tissue. In some embodiments when the diagnostic transducer is aligned with the landmark, the treatment transducer will be in a proper position to be activated without additional movement to successfully ablate the target tissue. In FIGS. 5A, 5B, 6A, and 6B diagnostic ultrasound transducer 125 may be positioned a predetermined distance, such as about 5 to about 15 mm, proximal to a treatment ultrasound transducer on a catheter such that when the diagnostic transducer 125 is aligned with a landmark 2, in this case a carotid bifurcation, the treatment transducer 126 is a predetermined distance 127 (e.g., about 5 to about 15 mm) distal to the bifurcation and aligned with an ablation target 128 in a carotid septum. The diagnostic transducer 125 may provide a signal as feedback to material (e.g., tissue, blood flow) reflecting ultrasound waves in the transducer's zone of capture 129. A sweeping motion may be created to search for the landmark, such as a common carotid artery, or carotid bifurcation by rotationally or translationally moving the catheter or by electrically or mechanically manipulating the transducer. Feedback from the diagnostic transducer 125 may be processed as images 130 as shown in FIG. 6B, acoustic sounds, waveforms, or electrical signals.

Figure 7B:
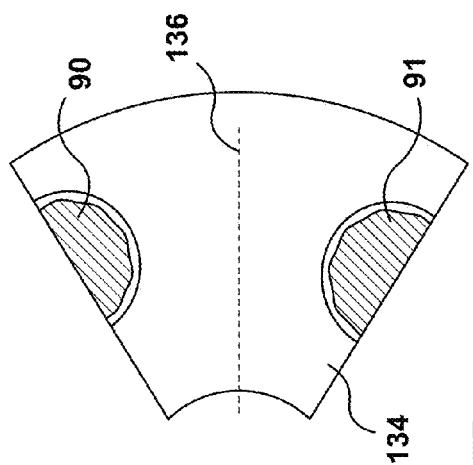
Figure 7C:
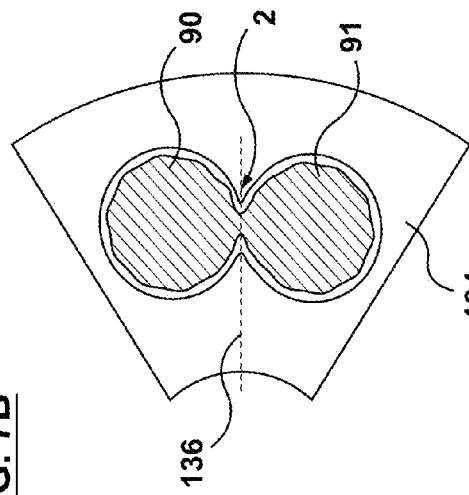
Figure 7A:
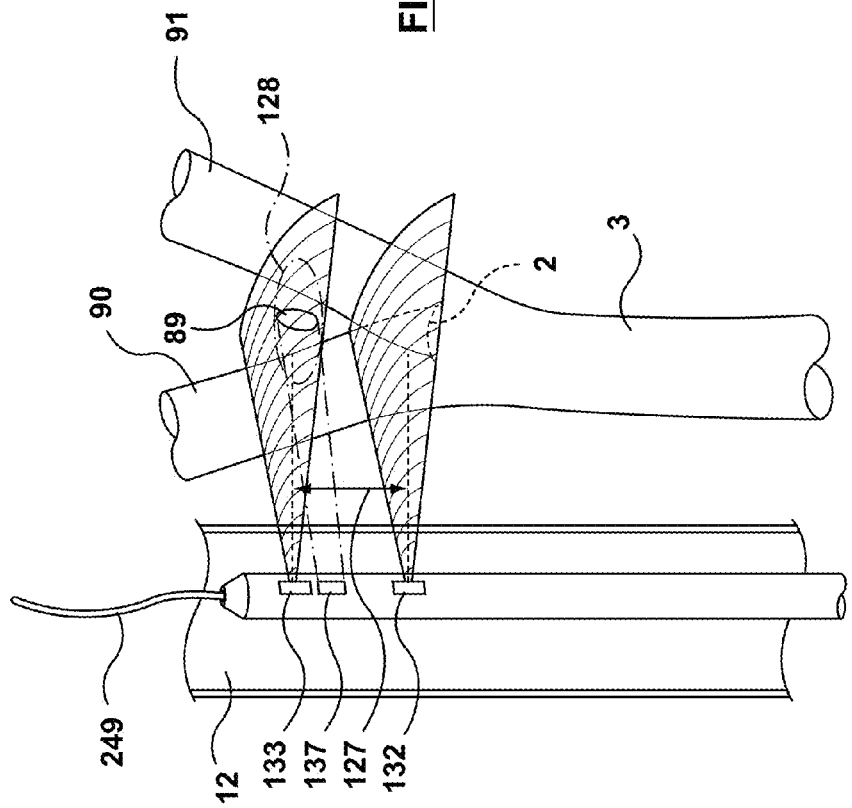

FIGS. 7A-C illustrate an exemplary ablation catheter that includes first and second diagnostic ultrasound transducers. As shown in FIG. 7A, the catheter may further comprise a first diagnostic ultrasound transducer 132 and a second diagnostic ultrasound transducer 133 configured to detect an internal 90 and external 91 carotid artery. The transducers can be configured to capture an image 134, as shown in FIGS. 7B and 7C, an acoustic signal, or an electrical signal. FIGS. 7B and 7C illustrate a trans-section of the two arteries. The second diagnostic ultrasound transducer 133 is positioned on the catheter so it is aiming the same direction as the treatment transducer 137. When the catheter is rotated to a position in which the second diagnostic transducer is centered 136 between the internal and external carotid arteries, as shown in FIG. 7B, and the first diagnostic transducer 132 is aimed at the carotid bifurcation 2, as shown in FIG. 7C, the ultrasound treatment transducer 137 is aligned with a target site 128 in a septum approximately centered between the internal and external carotid arteries and above the bifurcation a predetermined distance, such as between about 5 to about 15 mm, about 5 to about 10 mm, about 8 to about 10 mm, or about 10 mm to about 15 mm.

FIGS. 8A-D illustrate an exemplary ablation catheter with three diagnostic ultrasound transducers and one treatment ultrasound transducer. As shown in FIGS. 8A-D, the catheter includes a first diagnostic transducer 140 disposed on the catheter to align with a carotid bifurcation 2, a second diagnostic transducer 141 disposed on the catheter to align with an internal carotid artery 90, and a third diagnostic transducer 142 to align with an external carotid artery 91. The catheter also includes an ultrasound treatment transducer 143 positioned on the catheter relative to the three diagnostic transducers to aim an ablation beam at a target site between the internal and external carotid arteries and a predetermined distance, such as about 5 to about 15 mm, about 5 to about 10 mm, about 8 to about 10 mm, or about 10 to about 15 mm, cranial of a carotid bifurcation when the diagnostic transducers are aligned. Alternatively, one or more of the diagnostic transducers may be movable in relation to the catheter shaft. For example, diagnostic transducers 141 and 142 shown in FIG. 8A may mechanically move (e.g., with a gearing mechanism) to adjust the angle between the two transducers while maintaining the treatment transducer 143 centered between the two moving diagnostic transducers. This may allow the alignment to adjust to varying septum widths. In use, all of the catheters and methods shown in FIGS. 4A-8D create a lesion that is contained substantially in the carotid septum, and thus avoiding non-target tissue. In addition, a combination of blood flow cooling in the vein and a choice of ultrasound therapeutic regime can help cool the vein and the emitter that may get hot during operation while enhancing the ultrasound heating of the carotid septum.

Ultrasound Ablation Catheters Configured to Accept an Intravascular Ultrasound Imaging Catheter An endovascular catheter for carotid body ablation may be configured to both ablate target tissue using therapeutic ultrasound and image tissue for targeting purposes. A catheter may comprise an ultrasound ablation transducer (also referred to as a treatment transducer, or therapeutic transducer), be configured and adapted to accept an intravascular ultrasound imaging catheter, be adapted to identify a direction of aim of the treatment transducer with respect to the image produced by the imaging catheter, and be adapted to direct energy from the treatment transducer to a target identified by the imaging transducer.

There are a number of intravascular ultrasound (IVUS) catheters on the market that are used for imaging from within a patient's body. For example, Vision® PV .035 by Volcano is used for imaging diseased vessels from inside a vessel; Ultra ICE™ by Boston Scientific is used for imaging during endovascular cardiology procedures. Such IVUS imaging catheters may be configured to create an ultrasound-based video representing a cross sectional slice of tissue having a radius of about 50-60 mm around the imaging transducer on a distal region of the catheter. Ultrasound signals transmitted and received from the IVUS catheter are controlled and processed by a console external to a patient and an image may be produced and displayed to help a user identify tissues or other objects in the field of view. Additional processing may help to identify features such as blood flow, presence of plaque, or tissue differentiation. Existing IVUS imaging catheters may have a diameter of about 8 to 10 F (e.g., 8.2 F, 9 F) for example. In some embodiments of ablation catheters an existing IVUS imaging catheter, or a custom made IVUS imaging catheter similar to those known in the art, may be inserted into a carotid body ultrasound ablation catheter to help identify a target ablation site (e.g., carotid body, carotid septum, carotid body nerves), and identify the position of the target ablation site relative to the treatment transducer or its direction of aim.

Ablation Transducer in Front of Imaging Transducer

Figure 11:
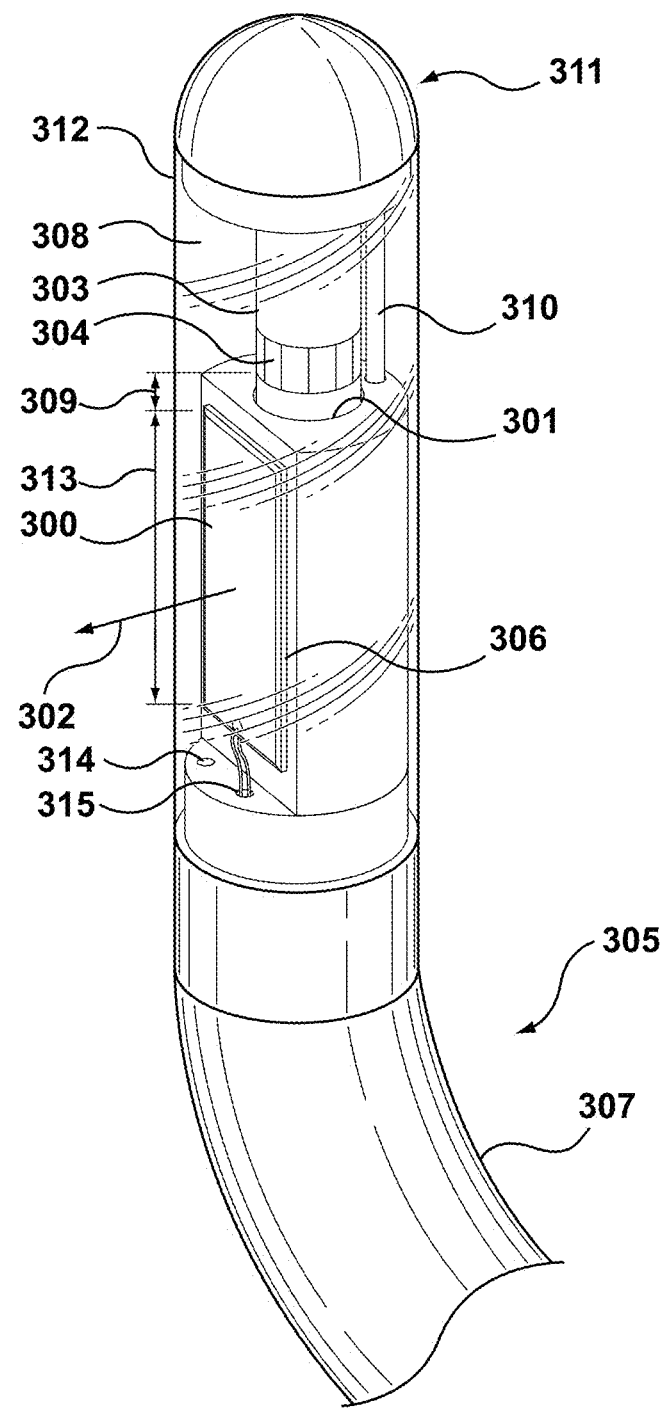
FIG. 11 is a schematic illustration of an ultrasound CBA catheter configured to accept a separate ultrasound imaging catheter.

An embodiment of an ultrasound ablation catheter 305 that is adapted and configured for ultrasound imaging, as shown in FIG. 11, is configured with an ablation transducer 300 positioned in front of an imaging catheter lumen 301. In this case, the positional reference, in front, may be defined as toward the direction of delivery of ultrasound ablation energy 302 from the ablation transducer or the side of the catheter that is aimed at a target. An existing ultrasound imaging catheter (e.g., IVUS catheter) 303 may be inserted through the imaging catheter lumen to position an imaging transducer 304 or transducers distal to the ablation transducer, wherein the imaging catheter lumen is behind the ablation transducer. The ablation catheter 305 may have a diameter in a range of about 11 FR to 13 FR (e.g., about 12 F) and be delivered through a deflectable sheath. For example, a compatible sheath may be 12 F compatible, have an outer diameter of about 16 F, be deflectable in at least one direction and be used with a dilator. The ablation catheter may comprise an ultrasound ablation transducer 300 such as the ablation transducers described herein, for example the ablation transducer may be substantially flat with a width of about 2 mm and a length of about 6 mm. The transducer may be configured to resonate at a frequency in a range of about 15 MHz to about 25 MHz (e.g., about 20 MHz). The ablation transducer may be mounted to a backing material 306 that reflects or shields ultrasound waves so ablation energy is only directed in a desired direction of delivery. The backing material may be made as described herein for similar embodiments for example made of a dense material such as stainless steel or an absorbent material such as air or an epoxy filled with microspheres of air. As shown, the imaging catheter lumen may pass through the backing material, or alternatively if a backing material is thin and mounted to a manifold component the imaging catheter lumen may pass through the manifold component. The imaging catheter lumen 301 may pass through the shaft 307 of the ablation catheter, which may be an extruded polymer such as Pebax, to a proximal region of the catheter. An ultrasound imaging catheter such as an IVUS imaging catheter may be delivered through the imaging catheter lumen to position the imaging transducer(s) 304 in an echolucent chamber 308 distal to the ablation transducer. For example, the imaging transducer(s) may be placed with an imaging-to-ablation-transducer-distance 309 of about 0 mm to 5 mm (e.g. about 2 mm, about 1 mm, about 0.5 mm). This configuration aligns an imaging plane approximately parallel to a direction of delivery of ablation energy and may be used to deliver ablation energy while imaging simultaneously or consecutively without needing to move either the imaging transducer(s) or ablation transducers. The echolucent chamber 308 may be a space within an echolucent shell 312 that allows imaging or ablation ultrasound waves to pass through without creating a significant echo. The echolucent shell may be made of a thin polymer such as nylon and may also be visibly transparent or translucent to allow a user to see into the echolucent chamber for example to position an imaging transducer or ensure coolant is flowing properly or that air bubbles are removed. The echolucent chamber may be hermetically sealed to contain flowing coolant. In this embodiment coolant may be delivered through a coolant delivery lumen 314, circulate in the chamber to cool the ablation transducer 300 and exit the chamber along the IVUS lumen 301. The ablation catheter may further comprise an aiming artifact 310, as shown, which may be positioned behind the imaging catheter lumen 301 or in a position that indicates a relative direction of delivery of ablation energy. For example, an aiming artifact may be a hypotube containing air and sealed at both ends, or an alternative design that is sonographically distinguishable such as embodiments described herein. As shown in FIG. 11 the aiming artifact may support a distal tip member 311, which may be a hemispherical piece made for example from a polymer or metal and adhered to the aiming artifact or echolucent shell 312. A distal tip member may be atraumatic when pressed against a vessel wall and allow for insertion into and passage through a sheath. A user may position the ablation catheter containing the imaging catheter, for example in a jugular vein or facial vein near a target carotid body, by obtaining an ultrasound-based video and positioning the catheter with the understanding that ablation energy will be delivered a predefined distance proximal to the imaging plane. For example, the ablation energy may be delivered in a range approximately starting at the imaging-to-ablation-transducer-distance 309 proximal to the imaging plane and with a height approximately the height 313 of the ablation transducer. For example, if the imaging-to-ablation-transducer-distance is 0.5 mm and the ablation transducer height is 6 mm then it may be understood that ablation energy will be delivered between 0.5 and 6.5 mm proximal to the imaging artifact and in a direction relative to the aiming artifact (e.g. opposite direction). The catheter may comprise electrical conductors 315 to deliver current to the ablation transducer or communicate a signal from a sensor such as a temperature or pressure sensor.

Alternatively, a similar configuration may comprise an imaging transducer or set of transducers that is manufactured as part of the ablation catheter instead of inserted as a separate device into an imaging catheter lumen of the ablation catheter.

In an alternative embodiment a catheter may be configured to position imaging transducers of an IVUS catheter proximal to the ablation transducer.

An Embodiment of an Ablation Catheter for Use with an Imaging Catheter

An ablation catheter configured to accept an ultrasound imaging catheter (e.g., IVUS catheter) may have a distal assembly 510 as shown in FIGS. 12A to 12F. The distal assembly may be connected to an elongate tube 511 such as an extruded Pebax tube that makes a catheter shaft. The distal assembly comprises a manifold component 512 connected to the shaft, an ablation transducer 513 mounted to the manifold component, an echolucent shell 514 defining a chamber 515 and connected to the manifold, a fiducial marker 516 positioned to provide an indication of a direction of aim 517 of the ablation transducer, and a radio-opaque tip 518.

Figure 12A:
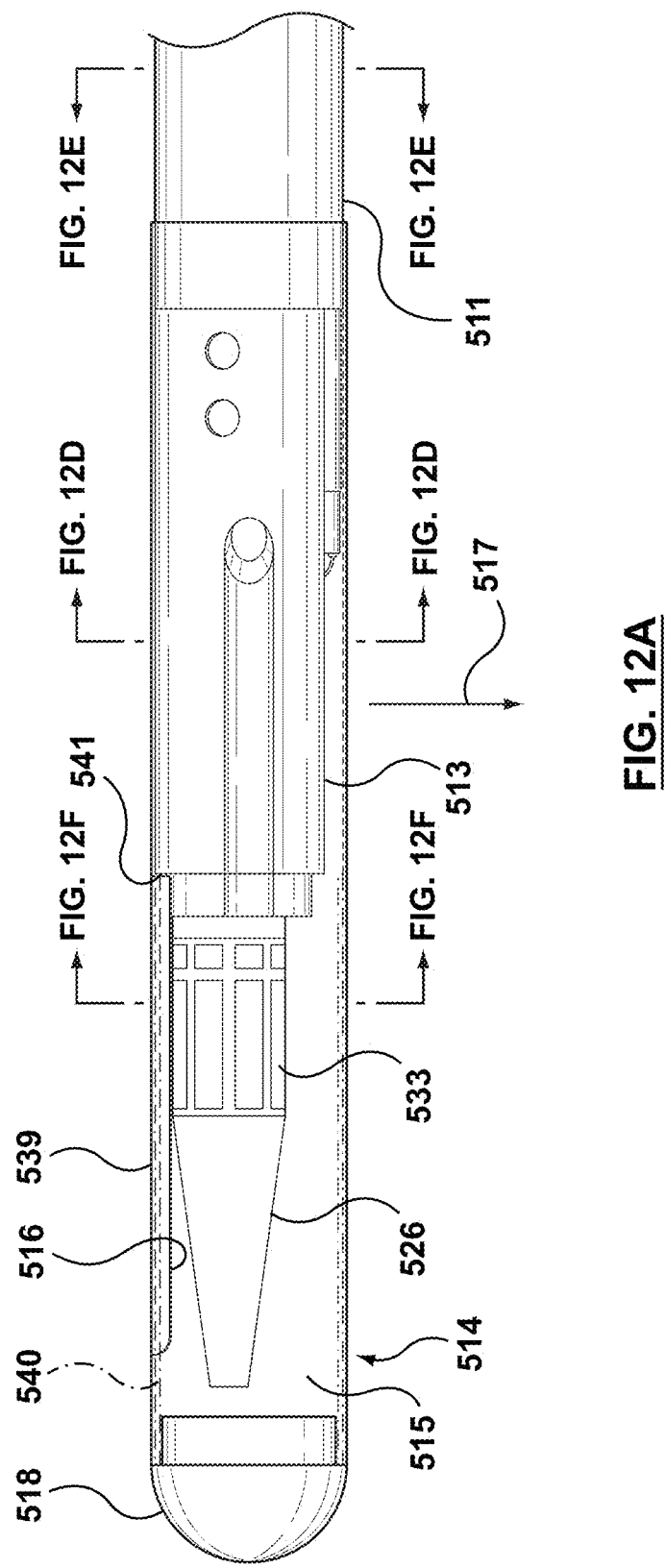
FIGS. 12A to 12I are schematic illustrations of an ultrasound CBA catheter configured to accept a separate ultrasound imaging catheter.
Figure 12B:
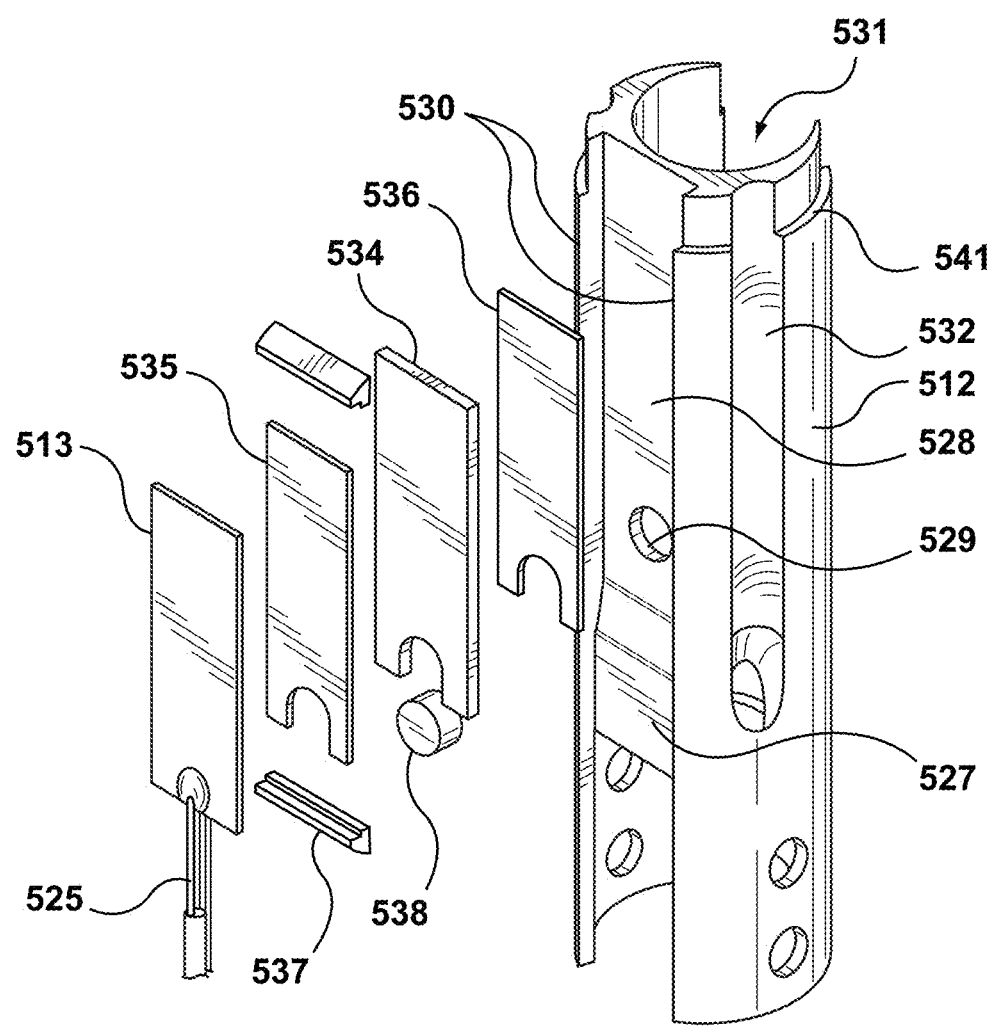
Figure 12C:
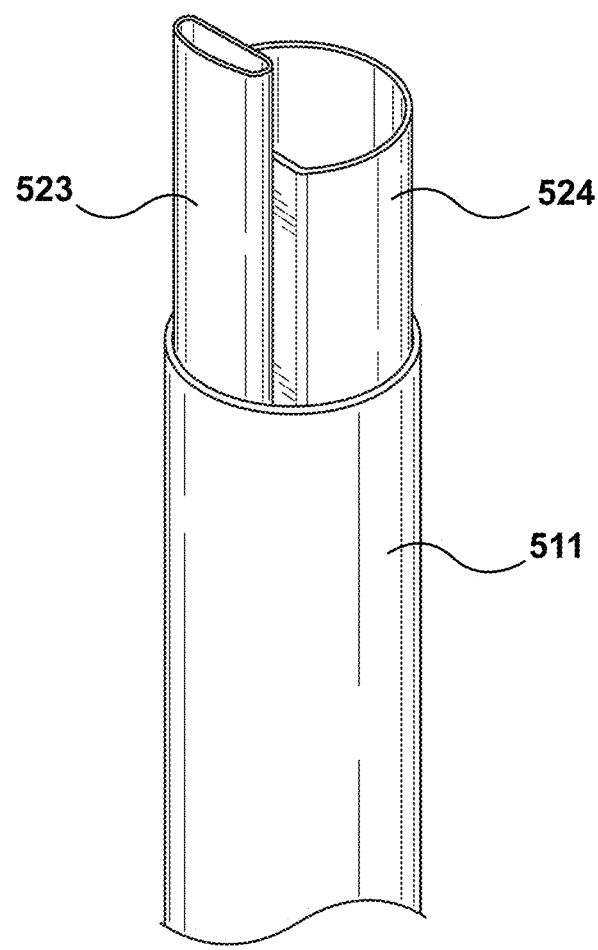
Figure 12D:
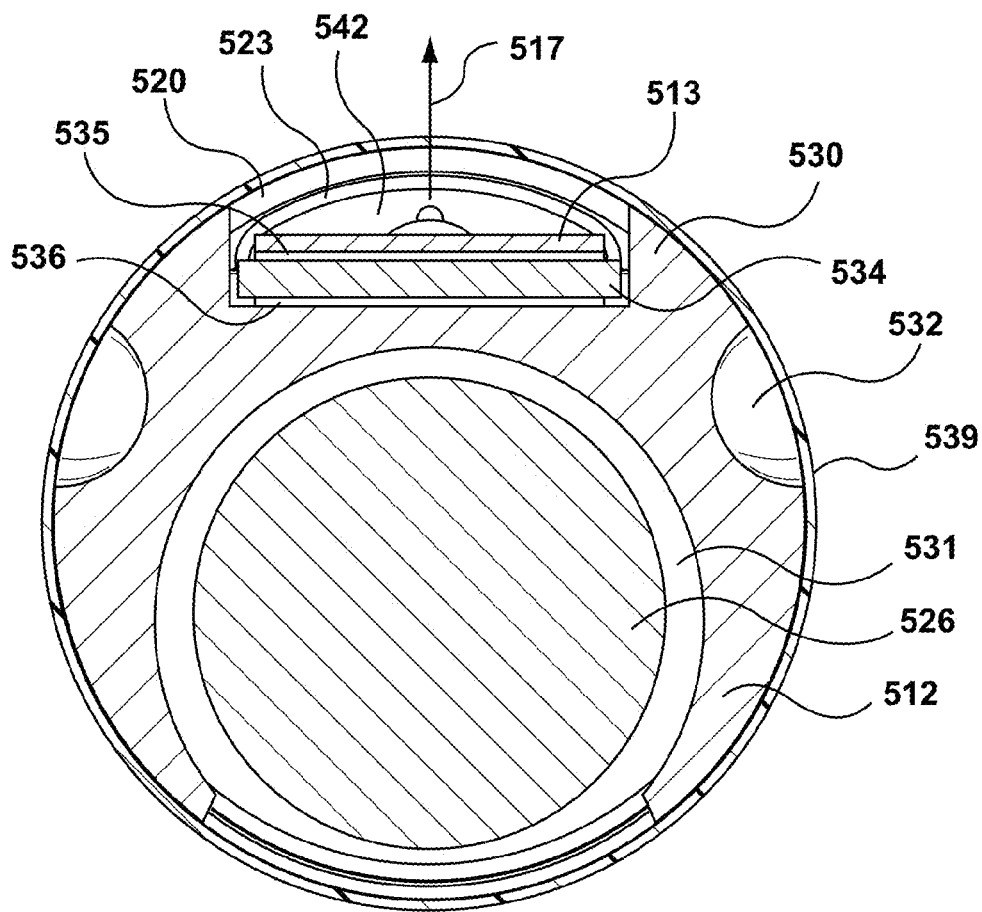
Figure 12E:
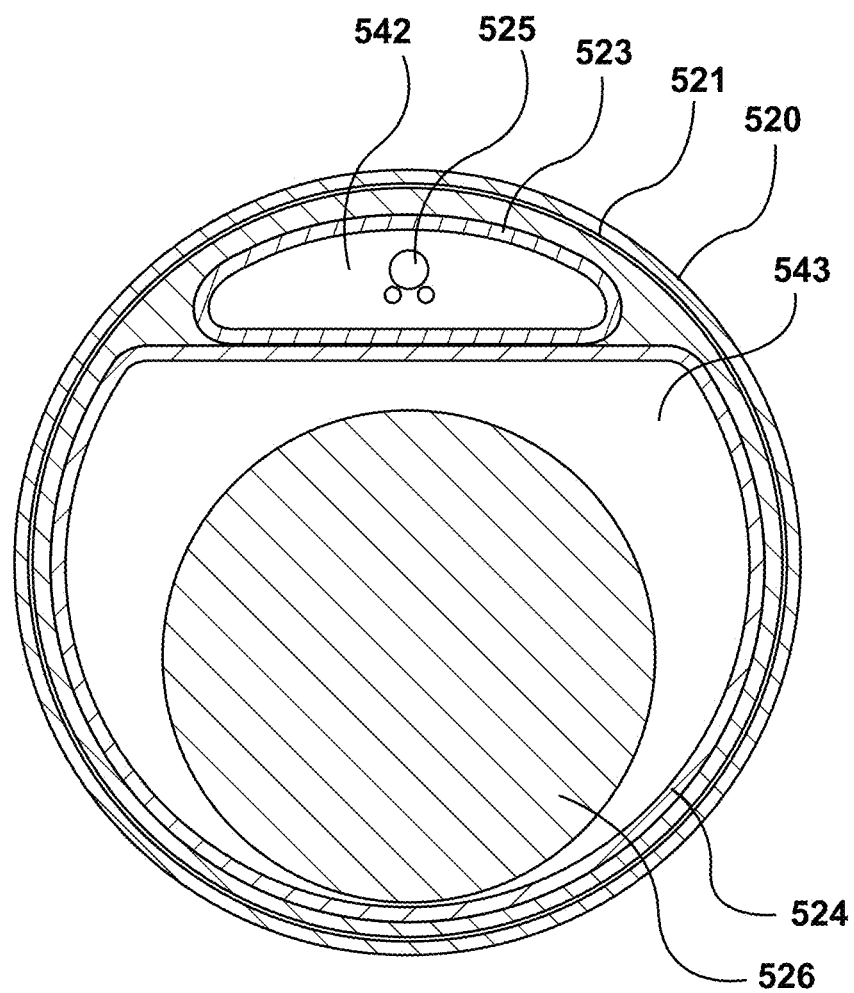

FIG. 12E shows a cross section of the catheter shaft of this embodiment. An extruded tube (e.g., a Pebax extrusion) 520 contains a wire braid 521 to increase strength and improve torqueability and a lumen. The wire braid may be coextruded or laminated to the extruded tube for example. Two PTFE liners are inserted into a lumen of the extrusion 520 to create two separate lumens. Alternatively, a Pebax extrusion may be extruded with two or more lumens. A first PTFE liner 523 defines a lumen 542 dedicated to contain wires 525 and delivery of coolant. Delivery of coolant, which is used to cool the ablation transducer, through a lumen containing the wires may have an added benefit of cooling the wires. The wires may be, for example, conductors to deliver high frequency current from a console to the ablation transducer and to connect a temperature sensor (e.g. thermocouple) in thermal communication with the ablation transducer to the console. In this figure three wires include a constantan wire and a copper wire to create a T-Type thermocouple soldered to the ablation transducer and a copper wire to deliver current to the transducer. One of the copper wires may be a common conductor to complete the thermocouple circuit and ablation energy circuit. Coolant fluid such as sterile water or saline may be provided in a vessel (e.g. bag, bottle) and pumped through tubing by a peristaltic pump to a coolant inlet port on a proximal region of the ablation catheter that is in fluid communication with the first liner or fluid delivery lumen 542. A pressure relief valve (not shown) may be positioned in line with the coolant inlet tubing to release coolant in the event that an occlusion somewhere along the coolant pathway inadvertently blocks coolant flow. The pressure relief valve may be open when the pressure in the tubing is about 30 psi for example. Optionally, a pressure sensor may be incorporated into the catheter or tubing set to monitor coolant pressure and signal a control console to adjust or stop flow of coolant or provide a warning. A second PTFE liner 524 defines a second lumen 543 dedicated for delivery of an ultrasound imaging catheter 526 and coolant outlet. The second lumen may have a shape and diameter (e.g., as shown) sufficient to allow passage of an imaging catheter 526 that may be for example about 8 FR to 10 FR (e.g., about 8.5 FR to 9 FR) and coolant while minimizing resistance to coolant flow. Alternatively, an IVUS lumen may be oval with a minor diameter sufficient to slidably fit an IVUS catheter. Alternatively a catheter shaft may comprise a separate coolant return lumen. At the proximal end of the catheter shaft the imaging catheter may enter the second lumen through a hemostasis valve to stop coolant from leaking from the lumen and a coolant outlet port may be in communication with the second lumen to release coolant from the catheter to a drainage vessel or return it to a coolant supply vessel. The shaft may have a diameter in a range of about 11 FR to 14 FR (e.g. about 12.5 FR) and length sufficient to reach a target tissue from a vasculature introduction area. For example a catheter configured to be introduced in a patient's femoral vein and delivered to either a right or left internal jugular vein proximate a carotid septum may have a length in a range of about 90 cm to 130 cm (e.g., about 110 cm).

As shown in FIGS. 12C and 12D the first and second lumen liners 523 and 524 extend from the extruded tube to interface with the manifold component 512. The first liner delivers the wires 525 and coolant delivery lumen 542 to a section of the manifold component dedicated for housing 528 an ablation transducer 513, which comprises a wire management shelf 527, an indented housing 528 for mounting the ablation transducer assembly, a solder relief hole 529, and protective ridges 530. The second liner 524 is in communication with an IVUS lumen 531 of the manifold component and coolant return slots 532 of the manifold component. An IVUS catheter delivered through the lumen 543 of the second liner 524 may pass through the IVUS lumen 531 of the manifold component and into the chamber 515. Coolant in the chamber may exit through the lumen 531 or coolant return slots 532 and pass through the lumen 543 of the second liner 524 to be removed from the catheter at its proximal region.

The manifold component 512 is connected to the catheter shaft 511 and is configured to hold an ultrasound ablation transducer 513 in a position relative to an imaging transducer 533 and direct flow of coolant fluid that stops the ablation transducer from overheating. As the ablation transducer vibrates heat is produced. The coolant passes over the ablation transducer to remove heat and maintain a temperature below a predefined maximum (e.g., about 90 degrees C.). An ablation transducer temperature that gets too hot may result in damage to the transducer or other components of the catheter or uncontrolled conduction of heat to the blood, vessel or other tissues. The temperature sensor may monitor transducer temperature to ensure coolant is flowing properly. If the temperature rises above a predefined maximum the console may respond by giving an error message, stopping delivery of ablative energy or adjusting delivery of ablative energy.

As shown in FIG. 12B, an exploded illustration of the manifold component 512 and ablation transducer assembly, the wires 525 may be soldered to the transducer 513. For example, the two wires of the high frequency current circuit may be soldered to opposing sides of the transducer and a constantan wire may be soldered to the inward facing side of the transducer to create a thermocouple with one of the copper wires. The ablation transducer may be adhered to a transducer backing 534, for example with cyanoacrylate 535 and the backing may be adhered to the ablation transducer housing of the manifold component, for example with cyanoacrylate 536. UV adhesive 537 may be applied to the edges of the transducer assembly to further strengthen its bond to the manifold component. The solder relief hole 529 accepts the protruding solder joint and may be filled, for example with UV adhesive 538 once the transducer assembly is adhered to the manifold component to pot the solder joint creating an electrical insulation and mechanically strengthening the solder joint. The protective ridges 530 define a channel for coolant to flow over the ablation transducer to the echolucent imaging chamber 515 and maintain a space between the ablation transducer and an echolucent shell layer 539. If the catheter is pressed into an internal wall of a vessel, for example by deflecting a steerable delivery sheath, the protective edges maintain the space by stopping the soft, thin layer of the echolucent shell from collapsing. An ablation transducer may be a flat, rectangular piezoelectric transducer (e.g., about 0.004" thick, 2 mm wide, 6 mm long). Alternative embodiments of ablation transducer are exemplified herein, such as curved transducers or transducer arrays. The ablation transducer backing may be made from stainless steel having a thickness of about 0.008". Alternative backing designs are exemplified herein, such as epoxy filled with glass microspheres filled with air. Adhesive between the ablation transducer and backing may have a thickness that is in sync with the wavelength of the ablation transducer and may be a consistent thickness to allow for repeatable transducer assembly performance, for example, decoupling of the transducer from the backing. For example, the space between the transducer and backing may be greater than about 0.0013" (e.g. about 0.002") for a transducer having a resonant frequency in a range of about 20 MHz to 21 MHz. The space may be filled with adhesive. In an alternative embodiment a thin layer of material that is less dense than the backing such as polyimide may be placed between the ablation transducer and backing to maintain a consistent spacing to ensure the ablation transducer vibration is not significantly dampened by the backing material.

In an alternative embodiment a manifold component may be configured to create turbulent flow of coolant over and around an ablation transducer. For example, the manifold may have similar features to the manifold component 512 shown in FIG. 12B however it may further comprise ridges or bumps (not shown) in the coolant flow area such as on the sides of the protective edges 530, or lumens (not shown) in the sides of the protective edges to encourage coolant to flow more in the region of the sides of the ablation transducer.

The echolucent shell shown in FIG. 12A partially defines a hermetically sealed chamber and is configured to allow ultrasound waves to pass through it with minimal interference. The echolucent shell may be comprised of multiple layers for example an inner layer 540 may be a nylon extrusion having a thickness of about 0.005", which may provide sufficient strength to the distal assembly. The inner layer may be adhered to a shelf 541 of the manifold component. A second outer layer 539 may be for example a thin PET or nylon sleeve having a thickness in a range of about 0.00025" to 0.0008". In an embodiment comprising an inner and outer layer made of nylon the layers may be melted together, which may eliminate air between the layers or a need for adhesive. Other materials that may be used for the first or second layers of the echolucent shell include PET or LDPE or other biocompatible materials having a relatively low acoustic impedance. As shown in FIG. 12A the outer layer extends over the manifold component and is bonded to the shaft 511 with adhesive. In this configuration the ultrasound imaging waves pass through the inner and outer layers and the ultrasound ablation waves pass through the outer layer only. A distal tip 518 is connected to the distal end of the echolucent shell and may have a rounded tip to facilitate delivery through a sheath and vessel and a shelf of decreased diameter for connection to the shell allowing a flush transition on the outer surface. The distal tip may be made from soft radio-opaque Pebax, which may be visualized when in use with X-ray or fluoroscopy.

Figure 12F:
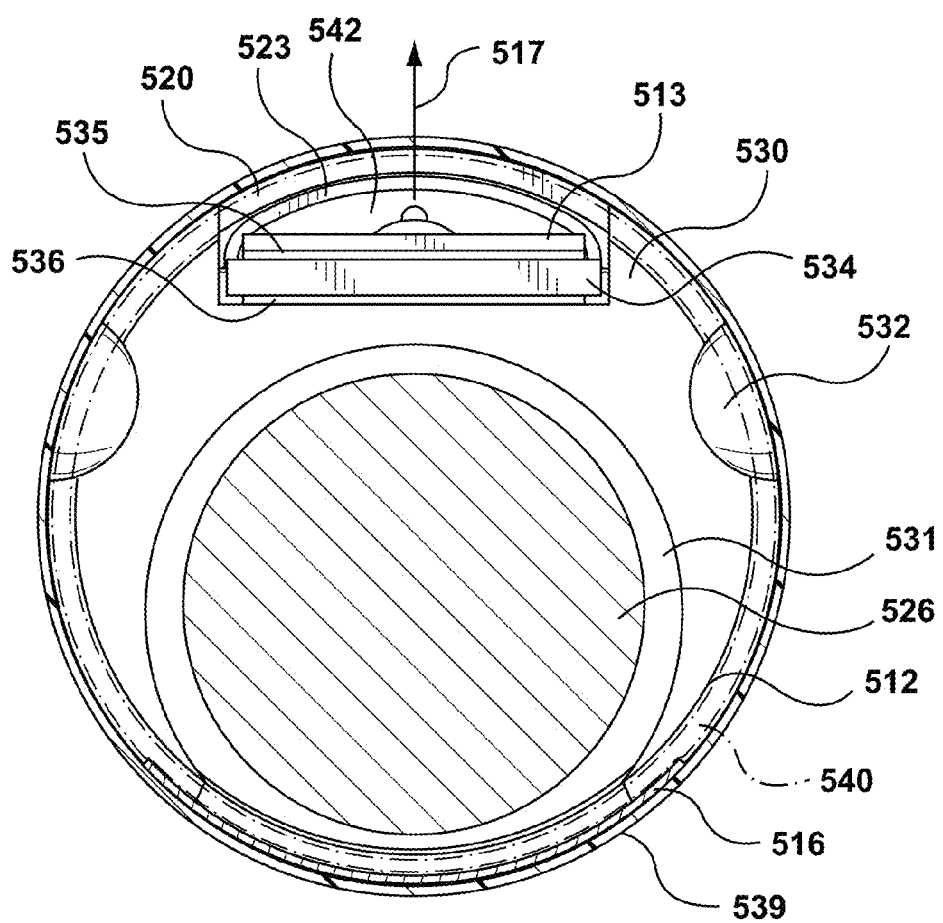
Figure 12G:
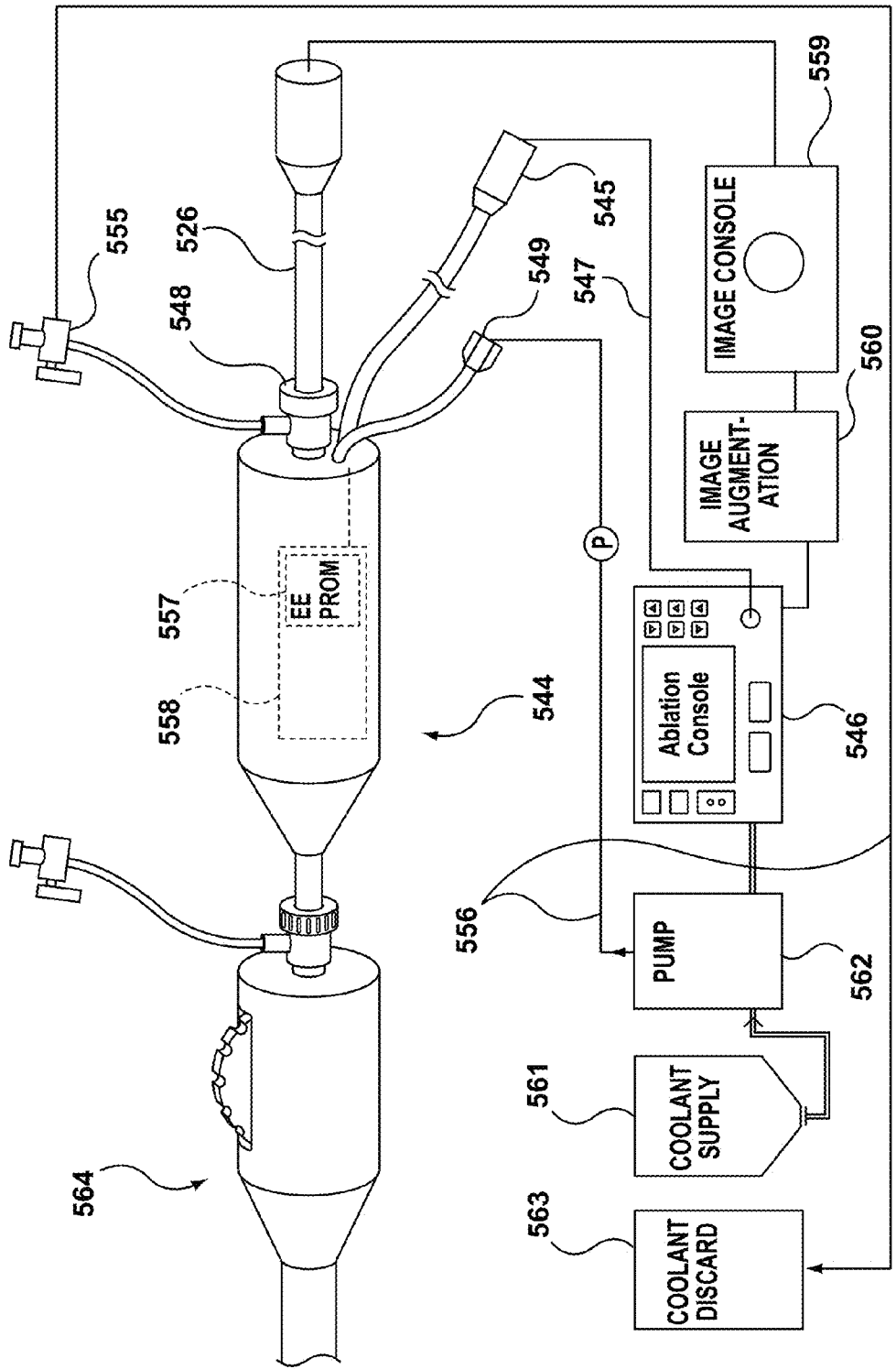
Figure 12H:
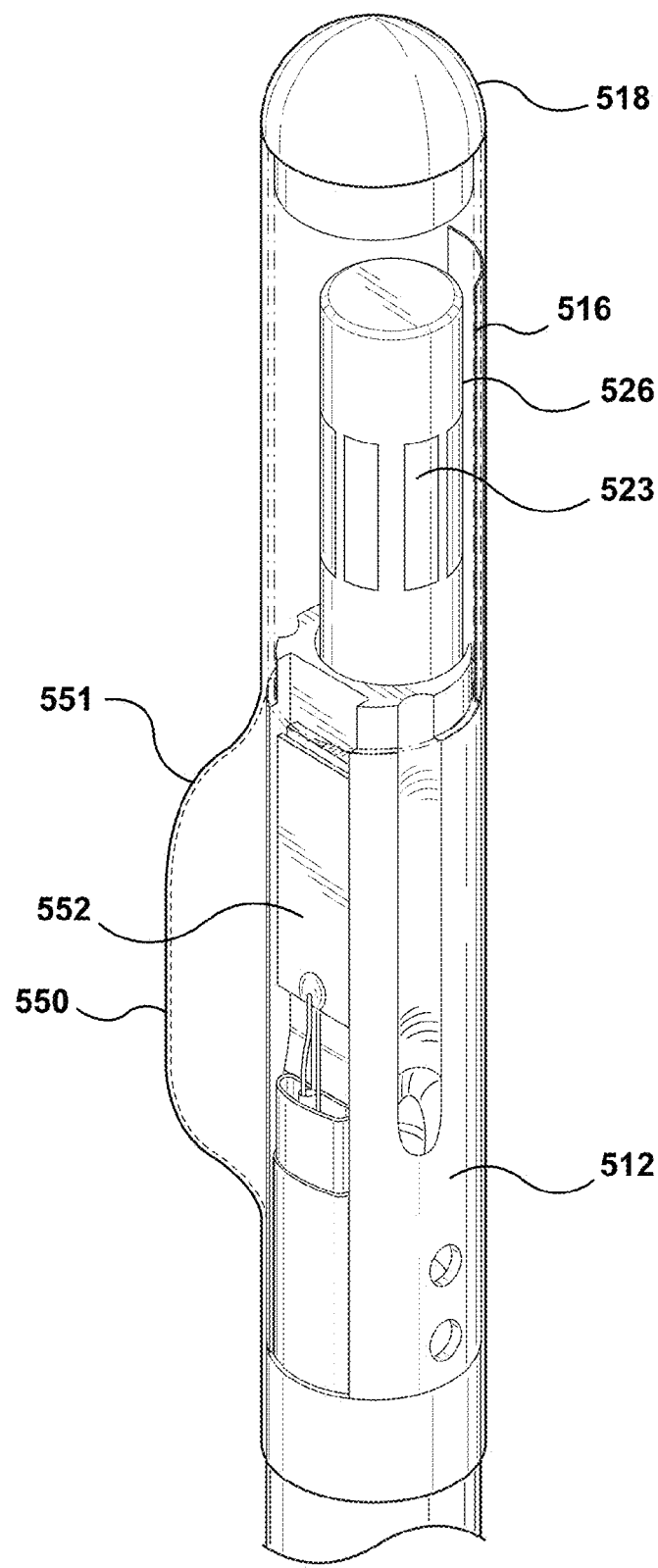

In an alternative embodiment as shown in FIG. 12H an outer layer 550 may be a balloon (e.g. nylon) having a bulge 551 positioned in front of an ablation transducer 552, which may allow a larger fixed distance between the ablation transducer and vessel wall and better cooling compared to a shell without a bulge. The bulge may be approximately 1 mm offset.

Figure 12I:
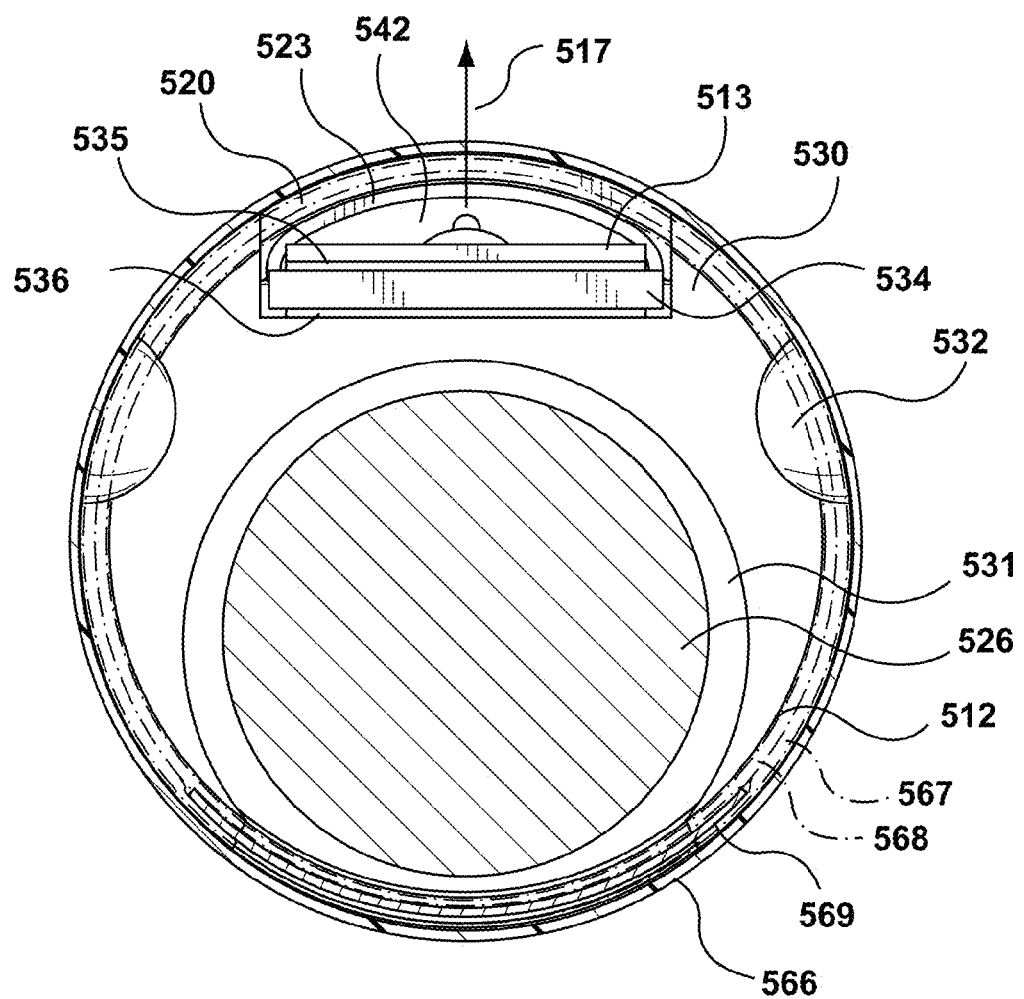

In an alternative embodiment as shown in FIG. 12I an echolucent shell may comprise an outer layer 566 which may be a thin layer of substantially echolucent material (e.g., nylon, PET, LDPE) which may be less than 0.001" (e.g., about 0.008") and an inner layer may comprise two layers 567 and 568 that sandwich a fiducial marker 569. The two layers 567 and 568 may be about 0.0025" thick and be made of material such as nylon that in combination with the outer layer 566 may be substantially echolucent to ultrasound waves emitted by imaging transducer(s) of an IVUS catheter 526.

In an alternative embodiment an echolucent chamber may contain an ultrasound ablation transducer but not an imaging transducer. An IVUS lumen may be configured to place an ultrasound imaging transducer of an IVUS catheter in proximity to the ablation transducer but in contact with the blood stream. A fiducial marker may be positioned in the field of view of the imaging transducer and may be for example a guidewire.

A fiducial marker 516 may be placed in a predefined position relative to the direction of aim 517 of the ablation energy such that an artifact is created on an ultrasound-based image or video indicating relative direction of aim of the ablation energy with respect to anatomical structures imaged. As shown in FIGS. 12A and 12F the fiducial marker 516 may be a thin band of echo-opaque material (e.g., a curved strip that is about 0.080" wide, 0.002" thick and 0.5" long and laser cut from a stainless steel tube) sandwiched between the inner 540 and outer 539 layers of the echolucent shell and positioned radially opposite the direction of aim of ablation energy. An alternative design comprises two inner layers of nylon that are about 0.0025" thick wherein a fiducial marker is positioned between the two inner layers and the two inner layers are melted together embedding the fiducial marker. This may prevent the fiducial marker from damaging a thinner outer layer. Alternative embodiments of fiducial markers are disclosed herein.

At the proximal region of the ablation catheter the shaft may be connected to a proximal manifold, which may also function as a handle 544 as shown in FIG. 12G. The handle may have an electrical connector 545 to connect wires for the ablation transducer and sensor(s) (e.g., temperature sensor) to the ablation console 546 via an interconnect cable 547, a IVUS port 548 with a hemostasis valve, a coolant input port 549 and coolant output port 555 that connects to a coolant tubing set 556. The tubing set may connect to a coolant supply 561 through a pump (e.g., peristaltic pump) 562 and a coolant discard container 563. An ultrasound imaging catheter (e.g., IVUS catheter) 526 may be inserted in to the IVUS port 548 and connected to an imaging console 559, which may optionally be connected to an imaging augmentation algorithm and display 560 or the ablation console b 546. The handle 544 may facilitate rotational manipulation of the ablation catheter. A memory storage element 557 such as an EEPROM containing a unique lesion depth table with settings for time and power may be in the handle and connected to the electrical connector to communicate with the ablation console. The handle may comprise a circuit board 558 for managing electrical connections and containing the EEPROM and other electrical capabilities such as connected device detection, use limitation (e.g., re-use prevention, limited duration of use, limited number of uses), and an electrical matching circuit that will minimize reflected energy in the system. The ablation catheter 544 may be inserted into a deflectable delivery sheath 564.

Optionally the ablation catheter may further be configured with a means for deflection or delivery over a guidewire as exemplified by embodiments disclosed herein.

Imaging Beam Aligned with Ablation Beam

An embodiment of a carotid body ultrasound ablation catheter may comprise a distal region that is delivered to a patient's vasculature and a proximal region that remains outside the body. The distal region is adapted to deliver ablative ultrasound energy from an ultrasound ablation transducer and ultrasound imaging signals from an IVUS imaging catheter. The catheter is configured to provide an image of tissue proximate the distal region that is aligned and oriented with the direction of aim of the ablation transducer. The user may image tissue around the distal region to search for and identify a target ablation zone (e.g., an intercarotid septum), orient the catheter so the ablation transducer is aimed at the target ablation zone, and deliver ablative ultrasound energy to the target ablation zone. In the FIG. 13, the distal region 320 comprises an echolucent shell 321, which may be a thin polymer or balloon for example. The cavity within the shell defines an echolucent chamber 322, which may be filled with a coolant (e.g., circulating saline or sterile water). For example, coolant may be delivered via coolant delivery lumen 332 and exit via coolant exit lumen 333. Within the echolucent chamber is an ultrasound ablation transducer 323 mounted to a backing 324, which is an ultrasound blocking material such as stainless steel or an epoxy containing microspheres of air. The ultrasound ablation transducer is aimed in a generally radial direction such that when ablative ultrasound energy is emitted it is delivered along the direction of aim 325. The ultrasound ablation transducer or backing may be mounted to the shaft 326, for example on a rod (e.g., hypotube) inserted in to a lumen in the ablation catheter shaft as shown or on a manifold component (not shown).

The carotid body ultrasound ablation catheter may comprise an elongate shaft 326, which may be made from an extruded polymer and may be a sufficient length (e.g., about 100 to 120 cm) to reach a patient's neck from a femoral vein when delivered through a vena cava to an internal jugular vein 12. Human internal jugular veins are typically about 8 to 20 mm in diameter. The shaft may be configured to fit in a jugular vein for example having a diameter of less than or equal to about 18 French (e.g., between about 9 and 11 French). The catheter may be delivered through a delivery sheath 327, a steerable delivery sheath, or over a guidewire 328. The shaft may comprise an IVUS lumen 329 that slidably accepts an IVUS imaging catheter 330. The lumen may extend from the proximal region of the catheter to the echolucent chamber at the distal region. The IVUS imaging catheter may be inserted into the IVUS lumen at the proximal region of the ablation catheter (e.g., in a handle) and advanced through the IVUS lumen to the distal region. The IVUS lumen may be oriented in the echolucent shell chamber such that the imaging transducer 331 of the IVUS catheter is positioned along the direction of aim of the ablation transducer.

Figures 14A, 14B:
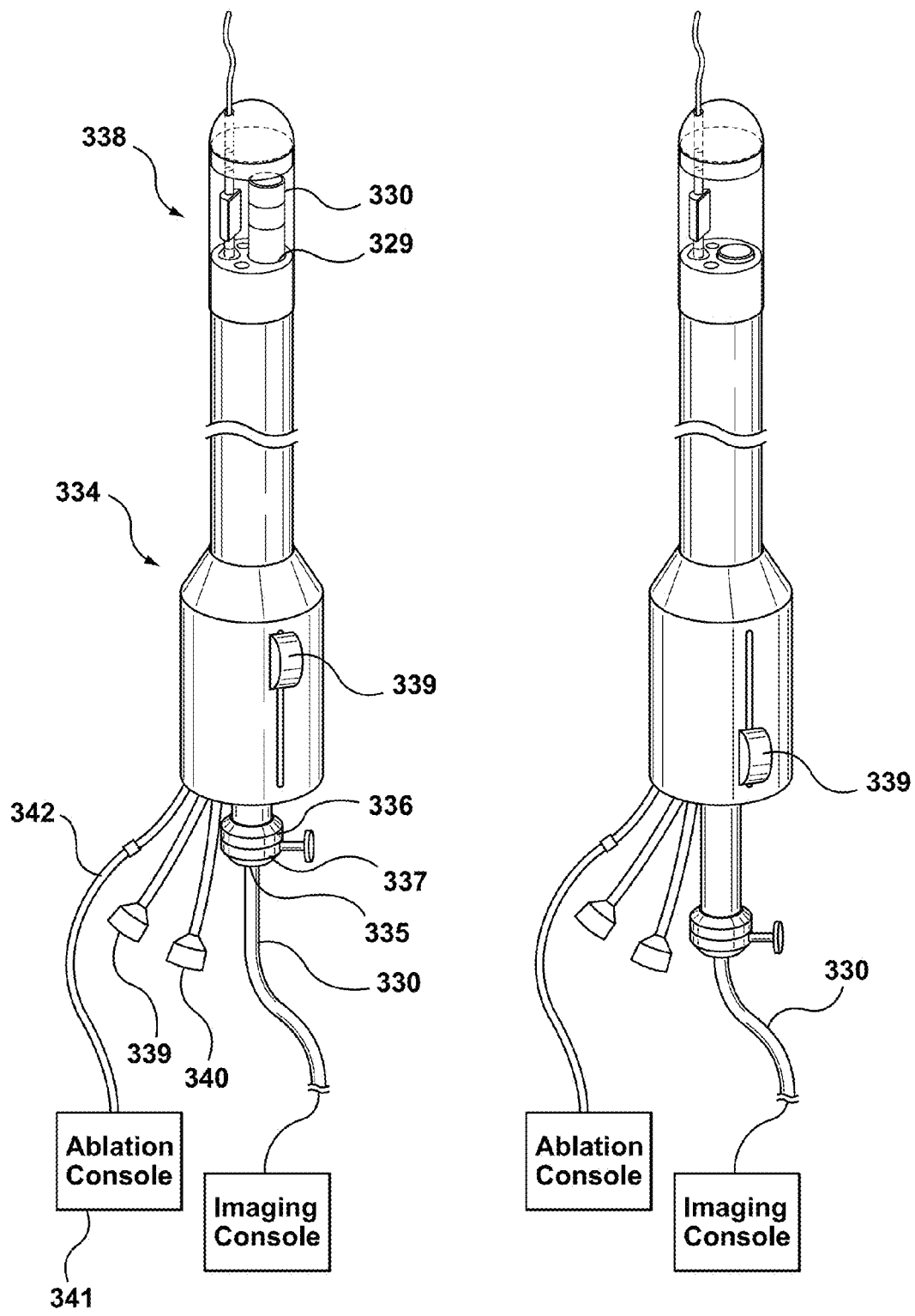
FIGS. 14A and 14B are schematic illustrations of an ultrasound CBA catheter configured to accept a separate ultrasound imaging catheter.

As shown in FIG. 14A at the proximal end of the catheter 334 the IVUS lumen 329 may be accessible to an IVUS imaging catheter 330, for example with a port 335 containing a hemostasis valve, and may comprise a mating feature 336 that mates with a mating feature 337 on a proximal end of the IVUS imaging catheter so that when the IVUS imaging catheter is fully inserted the mating features mate and the distal end of the IVUS imaging catheter is positioned appropriately in the distal region 338 of the ultrasound ablation catheter. The mating feature on the IVUS imaging catheter may be affixed to the catheter or it may be a separate adapter that is placed on the shaft of the IVUS imaging catheter and tightened on a desired position to act as a depth stopper. The mating feature of the ablation catheter may be movable between a deployed position, shown in FIG. 14A and a retracted position shown in FIG. 14B such that in the deployed position the IVUS imaging transducer is aligned with the ablation transducer and ready for imaging a target; and in the retracted position the IVUS imaging transducer is pulled toward the proximal end of the ablation catheter enough to move the distal end of the IVUS imaging catheter out of the direction of aim of the ablation catheter. An actuator 339 on a handle may be used to advance or retract the IVUS catheter. Alternatively, an IVUS imaging catheter may be manually advanced and retracted.

The ultrasound ablation catheter may further comprise a means to deliver coolant such as saline or sterile water to the echolucent chamber 322 of the distal region. For example, the shaft may comprise a coolant delivery lumen 332 and a coolant return lumen 333. The coolant delivery and return lumens may be connected to a coolant delivery 339 and coolant return 340 port at the proximal region of the ablation catheter. Coolant may be provided to the catheter by a coolant system comprising a coolant source such as a container of saline or sterile water, a conduit such as tubing, and pump such as a peristaltic pump. The coolant system may further comprise a flow pulsation damper or a flow meter. The coolant system may be controlled by the user or may be automatically controlled by a console 341 that coordinates delivery of coolant in coordination with delivery of ultrasound energy. For example, coolant may begin to circulate prior to delivery of ablation energy at a rate and time sufficient to ensure coolant is circulating in the echolucent chamber before ablation energy is delivered and continues at least until the ablation energy is stopped. Other signals may also be used in the control of coolant such as temperature of the ultrasound ablation transducer or echolucent chamber for example.

The ultrasound ablation catheter may further comprise electrical conductors connecting the ablation transducer to an electrical connector at the proximal region of the catheter (e.g., on the handle). The conductors may be held in a lumen in the shaft or a lumen in the hypotube (not shown). Other conductors may be present such as sensor conductors. A temperature sensor may be positioned in the echolucent chamber (e.g., on the echolucent shell surface, on the ablation transducer surface), which may measure temperature. Temperature measurements may be used to indicate sufficient power, excessive power, or overheating. The temperature signal may be used to control power delivery to the ablation transducer.

An alternative embodiment as shown in FIGS. 15A and 15B may comprise a machined manifold component 345, which may be made from a dense material such as stainless steel to act as an ablation transducer backing or the manifold component may be made from a plastic such as PEEK and a thin transducer backing may be added. The manifold component may be cylindrical with a cut away section that in combination with an echolucent shell 346 defines an echolucent chamber. An echolucent shell (e.g. a polymer sleeve, membrane or balloon with a thickness in a range of about 0.0002" to 0.009") is placed around the cut away section to form the echolucent chamber and contain circulating coolant. The manifold component has a means to bond to a polymer shaft such as a lip 347 that may have barbs or fenestrations that bind to the shaft 348 or holes to accept reflow of the shaft material. The manifold component comprises an IVUS lumen 349 in communication with the IVUS lumen in the shaft. An ablation transducer 350 may be mounted to the manifold component 345 as shown and the manifold component may have an indented housing 351 or outline where the ablation transducer is placed to facilitate fabrication. The manifold component may also comprise a coolant delivery 352 and return lumen 353 that are in communication with coolant lumens in the shaft when the manifold component is connected. The manifold component may also have a lumen to carry electrical conductors (e.g., to connect to the ablation transducer or sensor conductors such as temperature sensor). The distal end 354 of the manifold component may be rounded. The IVUS lumen may be positioned on the machined piece such that the center of the lumen lies on a direction of aim of the ablation transducer, which may be considered to be a perpendicular line to the ablation transducer face emanating from the center of the ablation transducer face. In the deployed state, the height of the IVUS imaging transducer 355 of an IVUS catheter 358 may align with the direction of aim of the ablation transducer as shown in FIGS. 15A and 15B.

Figure 13:
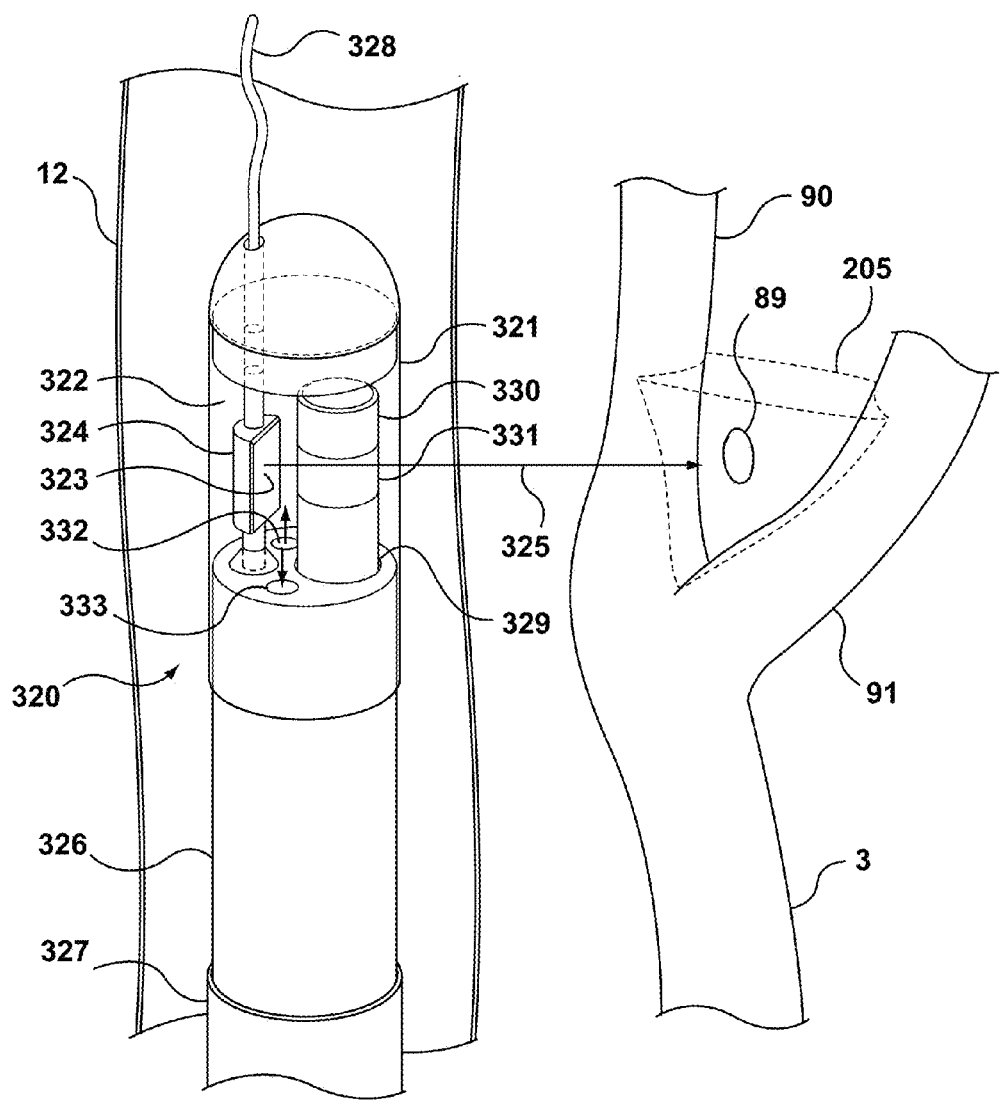
FIG. 13 is a schematic illustration of an ultrasound CBA catheter configured to accept a separate ultrasound imaging catheter.

Optionally, the ultrasound ablation catheter may comprise a means to be delivered over a guidewire 356. As shown in FIG. 13 or FIGS. 15A and 15B, a catheter may comprise a guidewire lumen 357 which may be on the side of the shaft or alternatively within the shaft.

Figure 16:
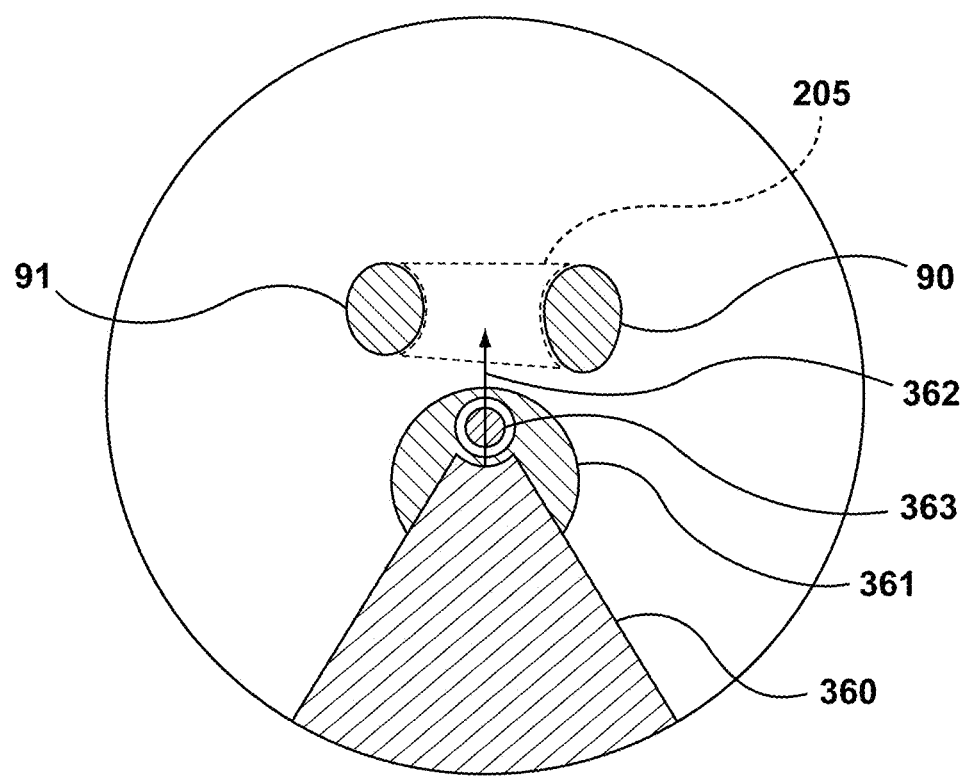
FIG. 16 is a schematic illustration of an ultrasound image generated during a transvenous carotid body ablation procedure.

An example of an image provided by an IVUS imaging catheter deployed in an ultrasound ablation catheter is shown in FIG. 16. Cross-hatched areas represent dark areas of the ultrasound image including a wedge-shaped shadow 360 cast by the ablation transducer or backing material, the vessel 361 containing the catheter (e.g., internal jugular vein, facial vein), an internal carotid artery 90 and an eternal carotid artery 91. The direction of aim 362 of the ablation transducer is opposite to the shadow cast by the ablation transducer and through the center of the artifact of the IVUS imaging catheter 363. The orientation of the ablation catheter, as shown, places the direction of aim 362 of the ablation transducer toward the carotid septum 205, which is between the internal and external carotid arteries and may be within about 7 or 10 mm superior from the carotid bifurcation. The carotid bifurcation may be identified as the catheter is advanced through the vessel (e.g., internal jugular vein, facial vein) and the internal and external carotid arteries converge. The distance from the carotid bifurcation may be determined, for example by advancing the catheter within about 7 mm which may be measured by depth markers on the shaft of the carotid body ultrasound ablation catheter in relation to a delivery sheath (not shown). Once the orientation and position of the ablation catheter is placed as desired with the direction of aim of the ablation transducer directed at the target area, the IVUS imaging catheter may be retracted so the distal end of the IVUS imaging catheter is removed from the echolucent chamber, or at least out of the way of the ablation signal, and ultrasound ablation energy may be delivered from the ablation transducer to the target area.

The ultrasound ablation catheter may further be adapted to articulate the distal region. Articulation may facilitate positioning of the ablation transducer in alignment with a target or expanding an ablation zone by creating multiple ablations associated with multiple positions of articulation.

Figure 17:
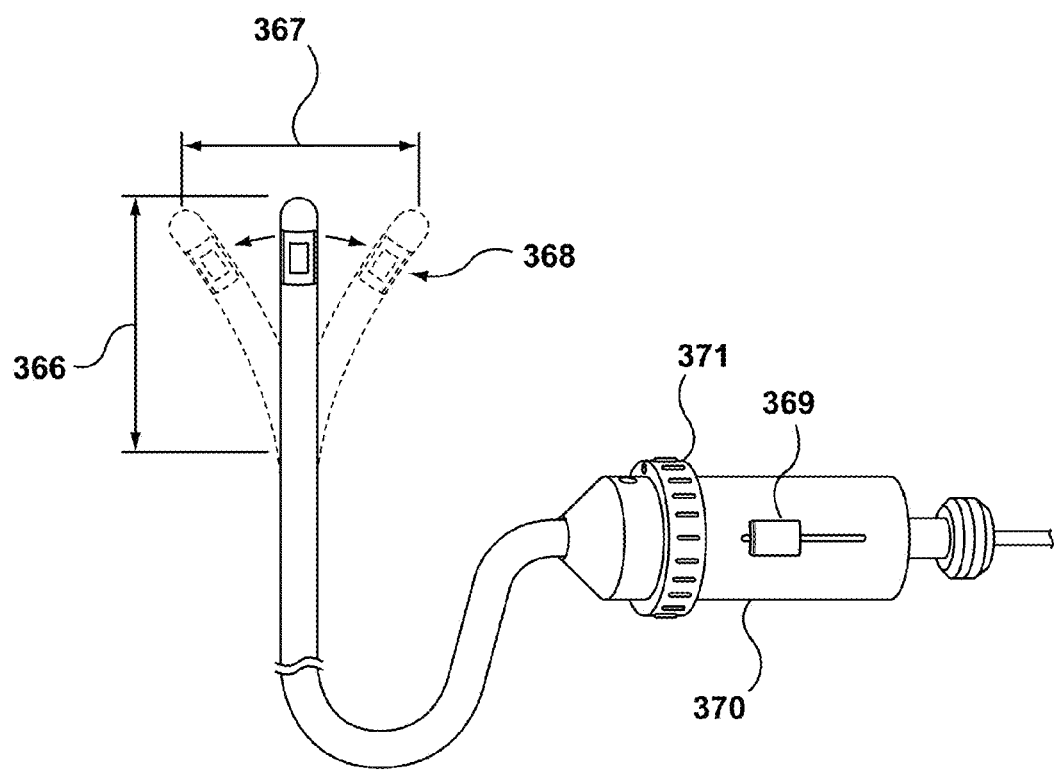
FIG. 17 is a schematic illustration of a deflectable ultrasound catheter

For example, the ablation catheter may comprise controllable deflection wherein a deflectable length 366 (e.g., about 1 to 3 cm) is bent from side to side up to a deflectable distance 367 (e.g., about 0.5 to 3 cm). Deflection may be in a plane that is coplanar with the ablation transducer as shown in FIG. 17. Controllable deflection may be achieved with pull wires connected to the distal region 368 (e.g., to a manifold component), the pull wires passing through lumens in the shaft to the proximal region where they may be connected to a deflection actuator 369 on a handle 370 that applies tension to a pull wire to deflect the distal region. The deflectable catheter may comprise a means to rotate the catheter shaft such as a rotation actuator 371.

Deflection may be configured in a plane that is substantially orthogonal to the plane of the ablation transducer or in any other direction which may facilitate placement of the treatment transducer, creation of multiple ablations, creating a larger ablation, or maneuvering or deforming a vessel (e.g., vein, jugular vein, facial vein) that contains the catheter to place the ultrasound ablation transducer in a suitable position to deliver energy to a target or to place the ultrasound imaging transducer in a suitable position to identify the target or tissues in the area of the target.

Angled Ablation Transducer

Figure 18:
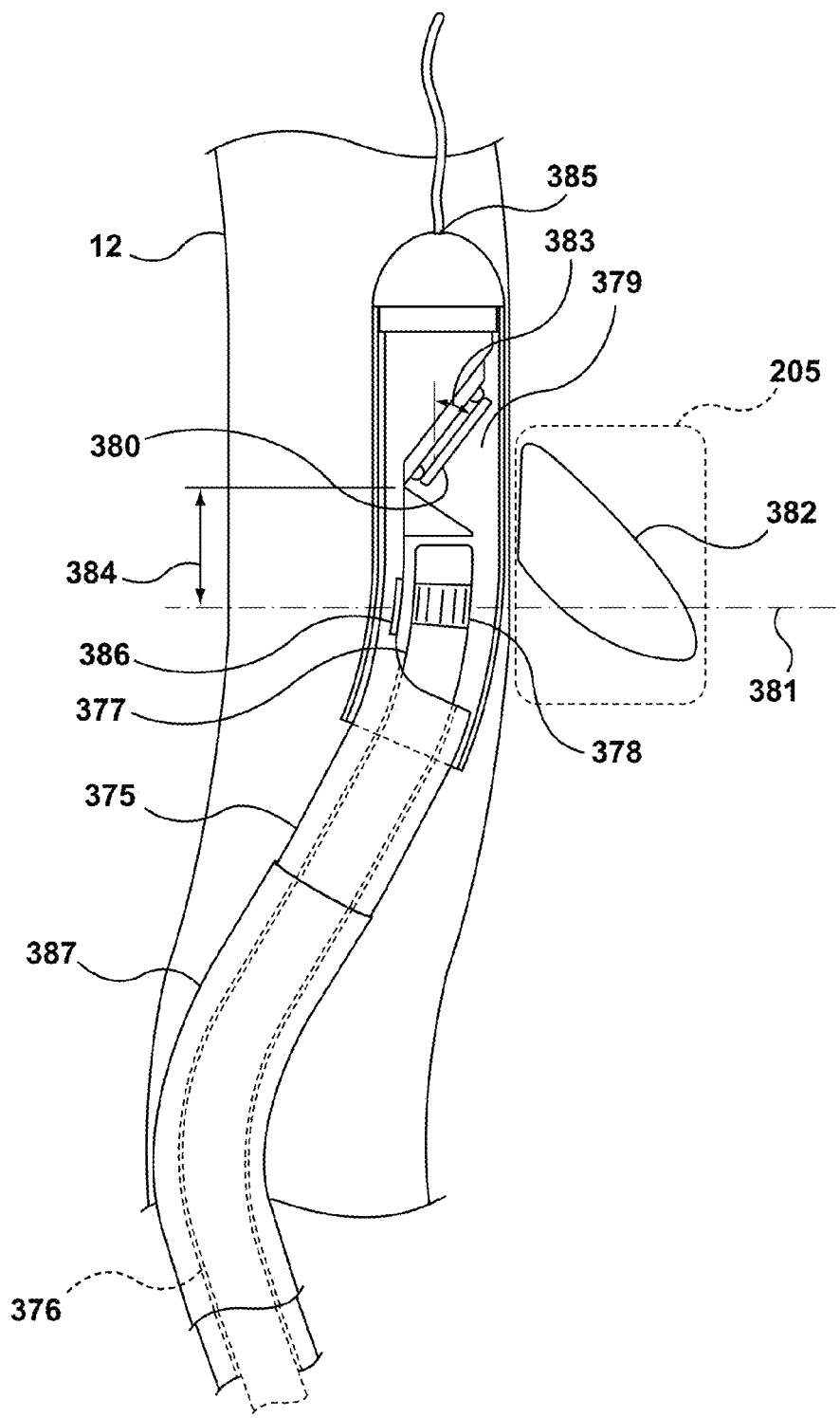
FIG. 18 is a schematic illustration of an ultrasound CBA catheter configured to accept a separate ultrasound imaging catheter.

An alternative embodiment of an ablation catheter 375 configured for ultrasound imaging and therapy, as shown in FIG. 18, may comprise an IVUS lumen 376 configured to accept a separate ultrasound imaging catheter (e.g., IVUS catheter) 377 wherein the imaging transducer 378 is advanced into an echolucent chamber 379 in the distal region of the ablation catheter, and an ablation transducer 380 positioned in the echolucent chamber distal to the imaging transducer and angled so that the emitted ultrasound ablation energy is directed to cross the imaging plane 381. The imaging plane may be a disc approximately perpendicular to the axis of the imaging catheter. Alternatively, an IVUS catheter may be configured to angle imaging transducer(s) slightly (e.g., about 85 degrees from the IVUS catheter axis instead of perpendicular to the axis) creating a slightly conical imaging slice. In FIG. 18 the ablation transducer 380 is positioned distal to the imaging transducer(s) and angled so that an ablation 382 created is directed to intersect the imaging plane or slice. Alternatively, an ablation transducer may be positioned proximal to the imaging transducer(s) and angled so that an ablation is directed to intersect the imaging plane or slice. The ablation transducer may be rectangular, have rounded corners, or be ovoid or circular. For example, in an embodiment configured to ablate a carotid body or carotid septum, the ablation may intersect with the imaging plane approximately 3 to 8 mm (e.g. about 5 mm) away from the surface of the imaging catheter, which may be a suitable distance from the catheter positioned in a jugular vein 12 or facial vein to the target area 205. An example configuration may comprise an ablation transducer that is 4 mm long and 2 mm wide. The ablation transducer may be placed at an angle 383 of between approximately 40° to 50° (e.g., about 45°) to the axis and at a distance 384 of about 3 to 10 mm (e.g., about 5 mm) distal to the imaging plane. An ablation zone may be created that has an elongated shape extending substantially perpendicular to the face of the ablation transducer. Benefits of this embodiment may include the ability to image a target zone while delivering ablation energy, or imaging a target zone then delivering ablation energy without having to move the imaging catheter, which may improve safety and efficacy by reducing a risk of moving the ablation energy off of the target. Furthermore, an angled ablation in a target zone may encompass a larger volume of the target zone while not extending beyond the target zone. An angled ablation transducer placed distal to an imaging transducer may allow for a reduced catheter diameter. In a similar embodiment an imaging transducer may be integrated into the ablation catheter instead of being a separate catheter advanced into the ablation catheter.

In the embodiment shown the ablation catheter 375 comprises a shaft (e.g., having an outer diameter of about 11 F), made from extruded polymer with a soft durometer with a braided jacket layer for improved torque response. The shaft comprises an IVUS lumen 376 (e.g., about 9.5 F) used to receive an ultrasound imaging 377 catheter. This lumen may also be used for passage of coolant. The ablation catheter may also comprise a guide wire lumen 385 (e.g., having a lumen diameter to slidably contain a 0.018" guidewire) for Over-The-Wire catheter delivery. The guidewire lumen may be a lumen in a tube (e.g., polyimide tube) passed through a lumen in the shaft and through the echolucent chamber to the distal end of the catheter. The ablation catheter may comprise a coolant delivery lumen, which may be a lumen in a coolant delivery tube that deposits coolant such as saline or sterile water in the echolucent chamber (e.g., distal to the ablation transducer). Coolant may flow within the echolucent chamber and out of a coolant exit lumen, which may be the imaging catheter delivery lumen. A temperature sensor (e.g., thermocouple, thermistor) may be placed within the echolucent chamber (e.g., on the ablation transducer, on the wall of the chamber) to monitor temperature and ensure sufficient coolant is delivered to avoid overheating. An aiming marker 386 may be positioned in the imaging plane next to the imaging catheter delivery lumen and opposite the direction of the delivery of ablation energy. The aiming marker may be made from a material that interacts with the imaging ultrasound waves to create a distinctive image on an ultrasound-based video. For example the aiming marker may be made from a material that absorbs ultrasound waves or that is a strong reflector of ultrasound waves. A distinctive image, or artifact, representing the aiming marker shown on an ultrasound-based video may be a shadow or highlight indicating that the ablation transducer is aimed in the opposite direction. Other configurations may be envisioned that create an unambiguous identification of the direction of aim.

An example of a method of use may comprise advancing a sheath 387 to a region proximate a target; advancing an ablation catheter 375 within a lumen of the sheath; advancing an imaging catheter in the lumen of the ablation catheter until the imaging transducer(s) is positioned in the echolucent chamber; deploying the ablation catheter containing the imaging catheter from the distal end of the sheath; while imaging with the imaging catheter using a combination of advancing and retracting the sheath together with the ablation catheter containing the imaging catheter and deflecting and torqueing the sheath to obtain a suitable position relative to the ablation target; torqueing the ablation catheter while imaging to aim the ablation transducer at the target. Optionally, a guide wire may be used. For example, a guidewire may be delivered first and the sheath and catheter may be delivered over the guidewire.

Angled Imaging Transducer

Figure 19:
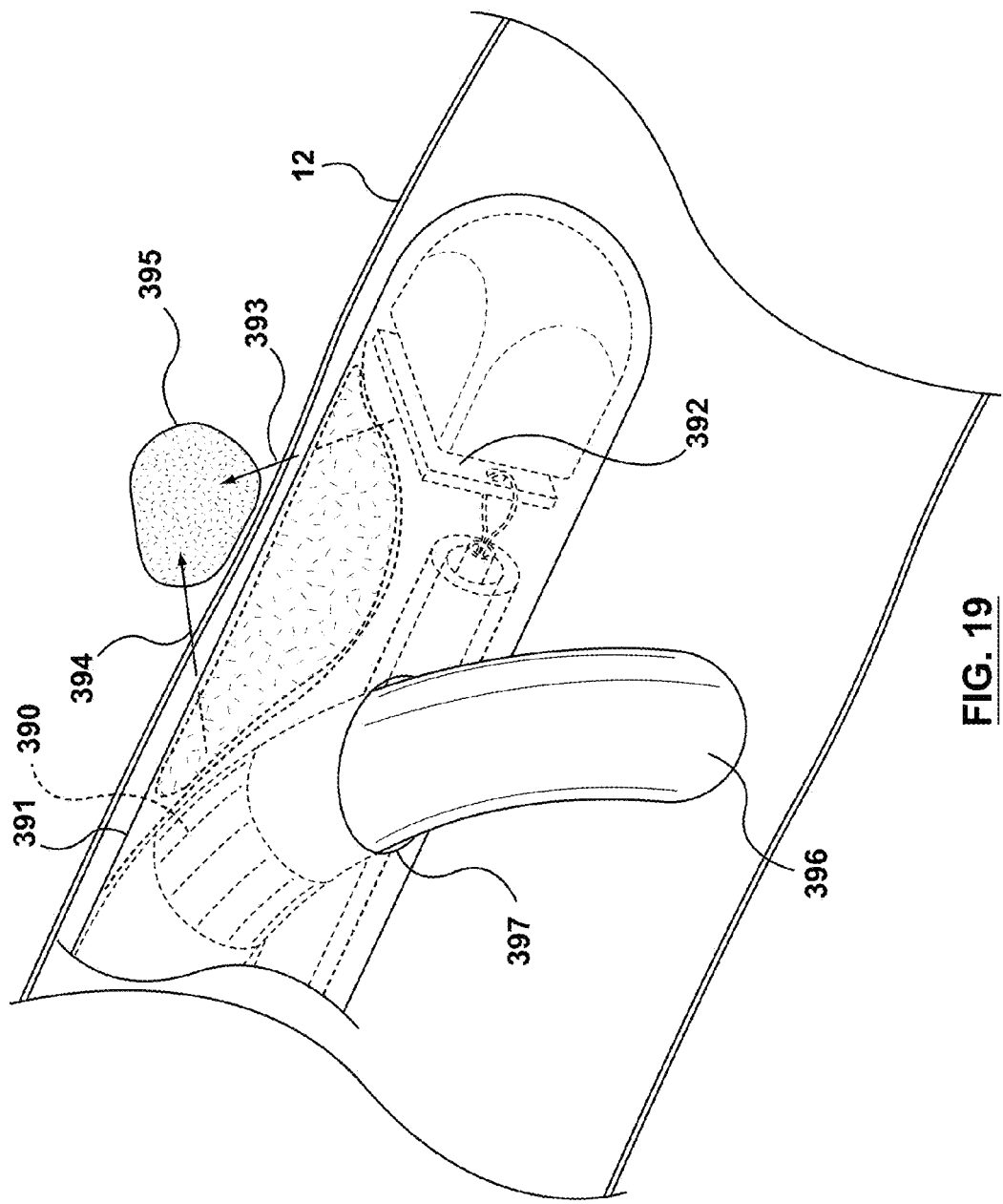
FIG. 19 is a schematic illustration of an ultrasound CBA catheter configured to accept a separate ultrasound imaging catheter.

An alternative embodiment comprises an imaging transducer(s) 390 that is positioned at an angle to the ablation catheter shaft 391. A separate ablation transducer 392 may be parallel to the ablation catheter shaft or angled as shown in FIG. 19. The ablation and imaging transducer(s) are placed at a distance along the catheter axis from one another and they are at an angle to one another so that ablation 393 and imaging 394 zones are overlapping at a distance radial to the ablation catheter that is suitable for ablation 395 of a target from a vessel 12 (e.g. ablation of a carotid body target from a vein such as a jugular or facial vein). In the embodiment shown, an imaging catheter 396 is advanced through a lumen in the ablation catheter. In the distal region of the catheter the lumen bends and exits through a port 397 on the side of the catheter. The imaging catheter passes out the port and the imaging transducer(s) 390 on the imaging catheter are positioned at an angle to the ablation catheter shaft. Overlapping imaging and ablation zones allow for simultaneous imaging and ablation of a target. The angle between the imaging and ablation transducers may be dictated by ablation catheter diameter, distance between the ablation and imaging transducers and intended ablation size. This angle may be for example between about 90° and 150°. This embodiment may allow for an ablation catheter having a smaller diameter than a design having ablation and imaging transducers positioned next to one another and on a substantially same axial position. This embodiment may also allow for using imaging catheters that have a long section distal to its imaging transducers that inhibits suitable alignment of imaging and ablation transducers. The long distal section may protrude out the lumen's exit port.

Since the distance between a vein and a target area may vary the vein may be manipulated as described herein to achieve suitable position and distance. Alternatively, an ablation catheter may be configured to angle the ablation transducer to achieve an ablation at an appropriate distance. For example, multiple catheters may be provided that are configured for creating an ablation at varying distances and angles from the ablation catheter.

Pivoting Ablation Transducer

Figure 20A:
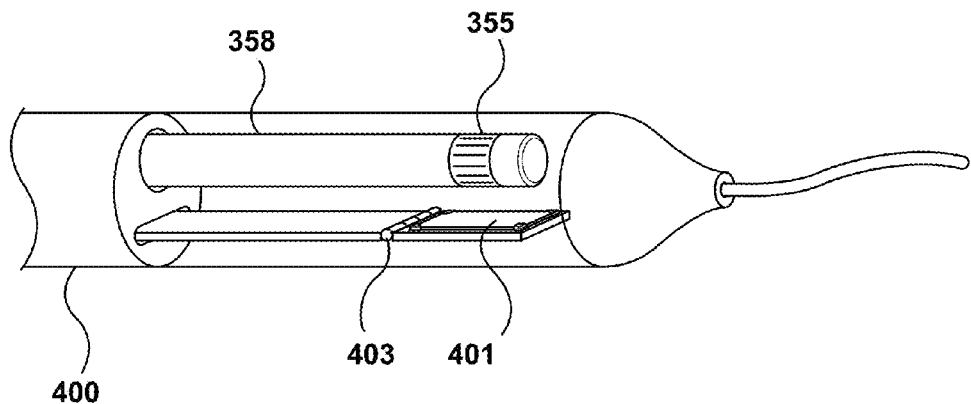
FIGS. 20A and 20B are schematic illustrations of an ultrasound CBA catheter configured to accept a separate ultrasound imaging catheter.
Figure 20B:
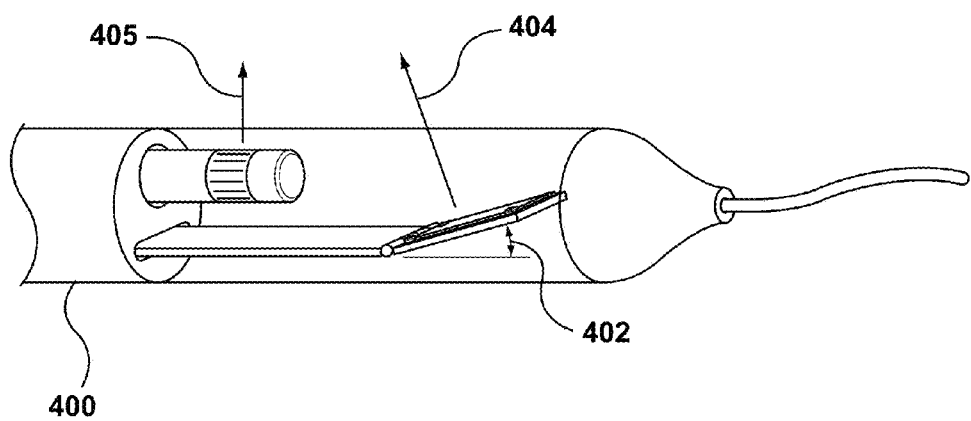

An embodiment of an ultrasound ablation catheter 400 configured to accept an imaging catheter 358 may have an ablation transducer 401 that may pivot to alter the angle 402 with the axis, as shown in FIGS. 20A and 20B. A user may control the pivot via an actuator on the proximal end of the catheter (e.g., a lever, dial, button, or knob on a handle) that for example, applies tension to a pull wire that pivots the transducer from one angle to another or to multiple positions between. As shown in FIG. 20A the ablation transducer 401 is positioned next to the deployed imaging transducer(s) 355. In this arrangement the device may be used in multiple ways depending on the anatomy and position of the catheter. Alternatively, the ablation transducer may be positioned distal to the deployed imaging transducer as shown in FIG. 20B. The pivoting mechanism may comprise a hinge or pivot hinge 403 at the proximal end of the transducer backing. A spring may urge the transducer to a first position (e.g., at an angle of about 45 degrees to the axis). A wire that is slidable held in a lumen of the catheter and connected to an actuator on the proximal end of the catheter may be pushed to engage and straighten the pivoting transducer or pulled to remove engagement with the transducer allowing it to spring to its angled configuration. The angle of the ablation transducer or relative position of the ablation transducer and imaging transducer may be adjusted to move an intersection of the ablation beam 404 and imaging plane 405.

IVUS Compatibility

A variety of IVUS catheters are available on the market. An ablation catheter configured to accept an intravascular ultrasound imaging catheter may be particularly configured to accept an IVUS catheter available on the market, such as the Visions® PV .035 IVUS catheter by Volcano, or UltraICE® IVUS catheter by Boston Scientific Corporation.

A Visions PV .035 IVUS catheter has an imaging transducer on its distal region. The imaging plane is about 13.5 mm from the very distal end. The transducer is 8.2 FR in caliber and about 6.5 mm long. The distance from the proximal end of the transducer to the very distal end of the catheter is about 18.5 mm. The catheter shaft is 7.0 FR and the working length is about 90 cm. The imaging transducer is made of a 64-element cylindrical array. The catheter has a guide wire lumen running from its distal tip to proximal end. An ablation catheter configured to accept a Visions PV .035 IVUS catheter may comprise an IVUS lumen having a minimal diameter about 8.5 FR and preferably with additional room for coolant return in the same lumen around the IVUS catheter. The space in the echolucent chamber may be long enough to contain the imaging transducer and portion of the catheter that is distal to the transducer. For example the distance from the distal edge of the manifold component to the end piece may be at least 18.5 mm (e.g. about 19 mm). The length of the ablation catheter may allow the imaging transducer to be positioned in the echolucent chamber while the Y-connector on the IVUS catheter's proximal end extends from the proximal end of the ablation catheter (e.g. from a handle on the proximal region). For example, the length of the ablation catheter from the distal end to the IVUS port on the proximal end may be no more than about 90 cm yet long enough to reach the target area (e.g., in a jugular vein near a carotid body) from an introduction site (e.g., femoral vein) while inserted through a deflectable delivery sheath. A valve such as a hemostasis valve on the IVUS port of the ablation catheter should be configured to allow passage of the 8.5 FR transducer while sealing around the 7 FR shaft to stop coolant from leaking for example up to a pressure of about 30 psi. The guidewire lumen of the IVUS catheter may be primed with coolant and sealed with a luer cap at the proximal end to stop coolant from leaking or air from entering.

An Ultra ICE IVUS catheter has a single 9 MHz imaging transducer mounted to a rotating drive shaft that passes through the IVUS catheter's shaft to the proximal region where it is connected to a motor to spin the transducer. The transducer is angled slightly toward the distal end. The imaging plane is about 5.5 mm from the very distal end. However, since the transducer is angled the image is a slightly distal looking cone rather than a transverse plane. The transducer is 9 FR in caliber and about 2 mm long. The distance from the proximal end of the transducer to the very distal end of the catheter is about 9.5 mm. The catheter shaft is 9 FR and the working length is about 110 cm. An ablation catheter configured to accept an Ultra ICE IVUS catheter may have an IVUS lumen having a minimal inner diameter of about 9 FR and preferably with additional room for coolant return in the same lumen around the IVUS catheter. The space in the echolucent chamber may be long enough to contain the imaging transducer and portion of the catheter that is distal to the transducer. For example the distance from the distal edge of the manifold component to the end piece may be at least 9.5 mm (e.g. about 10 mm). Consideration should be given to how the angle of the imaging transducer alters the position of the target relative to the image. The length of the ablation catheter may allow the imaging transducer to be positioned in the echolucent chamber while the connector on the IVUS catheter's proximal end extends from the proximal end of the ablation catheter (e.g. from a handle on the proximal region). For example, the length of the ablation catheter from the distal end to the IVUS port on the proximal end may be no more than about 110 cm (e.g., about 104.5 cm+/−2 cm) yet long enough to reach the target area (e.g., in a jugular vein near a carotid body) from an introduction site (e.g., femoral vein) while inserted through a deflectable delivery sheath (e.g., having a useable length of about 93.5 cm+/−2 cm). A valve such as a hemostasis valve on the IVUS port of the ablation catheter should be configured to allow passage of the 9 FR shaft while sealing around it to stop coolant from leaking for example up to a pressure of about 30 psi. Since the imaging transducer rotates on a drive shaft caution should be taken to avoid pinching the drive shaft or impeding its rotation. For example the ablation catheter may be configured to have minimal bend radius or tortuosity. A component may be provided that contains the motor drive and proximal region of the IVUS catheter relative to the proximal region of the ablation catheter to avoid kinking.

System

A system to support the ablation catheter may comprise an interconnect cable, a delivery sheath, a coolant tubing set, a coolant pump, and an ablation console. For embodiments configured to accept a separate imaging catheter the system may include an imaging catheter and imaging console or these may be provided separately. For embodiments configured with an integrated imaging transducer an imaging console may be integrated with the ablation console or a separate unit. Other components, such as coolant (e.g., sterile water or saline in an IV bag or bottle), introducers, site preparation supplies, and dressings, used in the procedure may be provided in a kit or procured from a procedure facility's supplies. A system may also comprise a brace to hold a patient's head and neck still relative to the torso. For embodiments configured for use with a guide wire a system may comprise a guidewire or a set of guidewires (e.g., guidewires having 0.018" diameter or 0.035" diameter, guidewires with preformed bends, deflectable guidewires).

The interconnect cable may be configured to connect the ablation catheter to the ablation console, for example with mating quick-connect connectors and suitable conductors. The interconnect cable may be a suitable length (e.g. about 8') to separate the ablation console from the sterile field and not impede catheter maneuverability during the procedure.

The delivery sheath may deflectable in at least one direction. It may have a soft (e.g. about 35 D durometer) atraumatic tip, a lumen with a diameter suitable to slidably fit the ablation catheter (e.g. about 0.174"), a corresponding outer diameter (e.g. about 0.210"), and a valve to allow passage of the ablation catheter (e.g., a Tuohy-Borst valve)

The coolant tubing set may be compatible with the coolant pump, for example having a section that feeds through and functions with a peristaltic pump. The coolant tubing set may comprise luer lock connections that are compatible with commercially available IV solution administration sets and extension sets. The tubing set may comprise a tube that delivers coolant from a pump tube section to the coolant delivery port of the ablation catheter's handle. This section of tube may further comprise a pressure relief valve to open in case of inadvertent high pressure for example caused by catheter occlusion. This section may further comprise a pulsation damper. The coolant tubing set also comprises a coolant return tube to be connected to the coolant return port of the ablation catheter handle. The coolant return tube may return coolant to the coolant storage vessel or discard it. In one embodiment the coolant storage vessel only contains enough coolant sufficient for a limited number of ablations and return coolant is discarded so in the case of a catheter leak only a limited amount of coolant is delivered to the patient's blood stream.

The ablation console may be a computerized electrical signal generator that delivers high frequency (e.g., in a range of about 10 to 25 MHz, about 20 MHz) alternating current to an ultrasound ablation transducer. Parameters of the delivered energy may be selected by a user or may automatically be determined. For example, the console may read data from memory in a catheter and deliver energy accordingly or in combination with a desired parameter such a lesion depth. The console may also coordinate coolant pumping or imaging capabilities. The console may identify conditions that indicative of a malfunctioning catheter or undesired procedure and alert a user or adjust energy delivery to mitigate the problem. A console may be configured to deliver nerve stimulation signals to a catheter. For example, an ultrasound signal that mechanically or thermally stimulates a nerve may be delivered without ablating tissue to confirm effective or safe aim of an ablation transducer prior to delivery of ablation energy and following ablation to confirm successful ablation. Alternatively, a catheter may comprise one or more stimulation electrodes and the console may deliver an electrical nerve stimulation signal to assess proximity to a nerve.

Manipulation of a Vein to Obtain a Suitable Ablation Position

Configuration of veins near a target site may vary from patient to patient or side to side within a patient. An ablation catheter 411 such as any of the embodiments of ultrasound ablation catheters disclosed herein may be delivered to a vein 12 that is near a target site 205 and in a suitable position for a carotid body ablation procedure. For example, conditions for a suitable position may comprise the distance 410 from an interior surface of a vein wall to a border of a target site such as an intercarotid septum to be within about 0 to 5 mm and alignment of the vein 12 with the target to allow delivery of ablative energy without obstruction or unsafe interference. Alternative conditions for a suitable position may depend on the configuration of the ablation catheter. In some patients there may not be a vein in a suitable position, however, an ablation catheter may be delivered to a vein that may be maneuvered to a suitable position. Maneuvering a vein, or a catheter within a vein, to a suitable position may comprise techniques such as palpating the neck, rotating the head, deflecting a deflectable ablation catheter, deploying a structure from an ablation catheter such as the deployable wire, deflecting a deflectable sheath, or a combination of these.

Figure 21A:
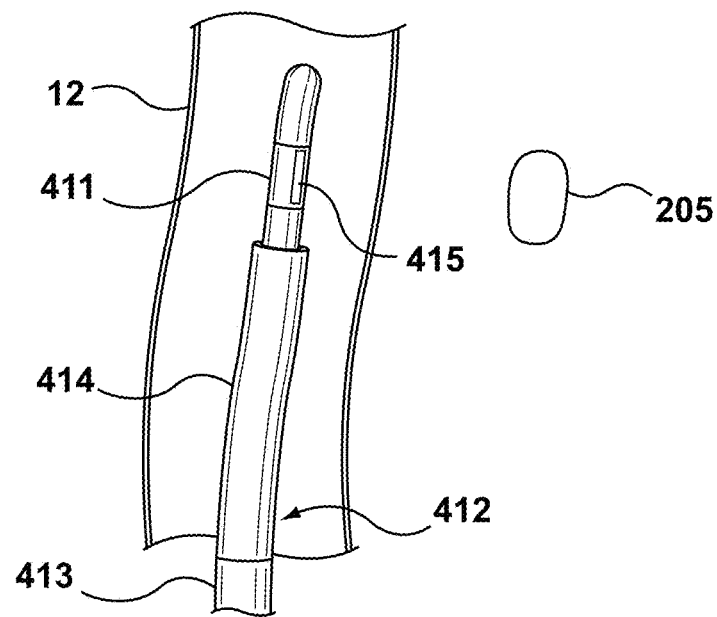
FIGS. 21A, 21B, and 21C are schematic illustrations of a CBA catheter and deflectable sheath manipulating a position of a vein.
Figure 21B:
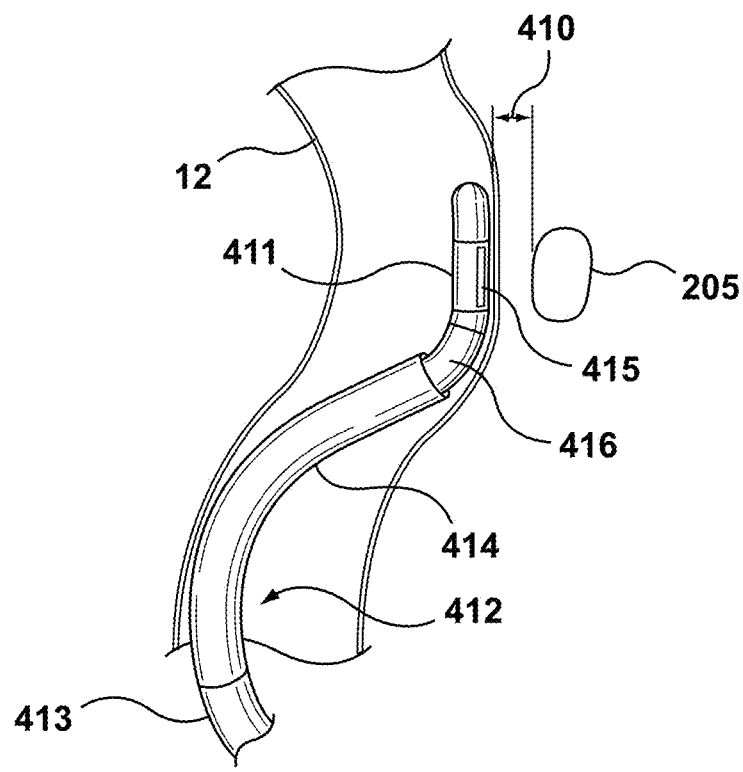

A deflectable sheath 412, as shown in FIG. 21A to 21B, may be configured for deflection in at least one direction, have an outer diameter of about 9 FR to 16 FR and have an inner lumen to slidably engage an ablation catheter 411. The sheath may have an elongate section 413 and a deflectable section 414 with a central lumen running through. A braided jacket may surround the elongate section to improve torque response. Active deflection may be accomplished by a pull wire running through a pull wire lumen in the sheath from a handle on the proximal end to an anchor at the distal end of the deflectable section. Tension may be applied to the pull wire by an actuator on the handle. The handle may also facilitate torqueing manipulation and comprise a lumen to accept the ablation catheter with a clamping adapter such as a Tuohy-Borst connector. The sheath may comprise a deflectable section 414 near or at the distal region of the sheath. The deflectable section may be for example between about 1 to 5 cm long (e.g. about 3 cm long) and be positioned at the distal end of the sheath as shown in FIGS. 21A and 21B.

FIG. 21A shows an ablation catheter 411 delivered through a deflectable sheath 412 in an undeflected state to a jugular vein 12 wherein the target tissue 205 is not sufficiently close to the ablation transducer 415. FIG. 21B shows the deflectable sheath 412 in a deflected state, which presses the ablation catheter 411 into the vein wall and manipulates the malleable vein to obtain a suitable distance 410 between the target tissue and ablation transducer. In such a configuration the ablation catheter 411 may have a bendable section 416 that bends to allow the catheter distal to the bendable section 416 to align with the vessel wall yet stiff enough to apply a force to the vein to manipulate its position. For example the bendable section 416 may have a durometer in a range of about 40 D to 55 D (e.g., about of 50 D).

Figure 21C:
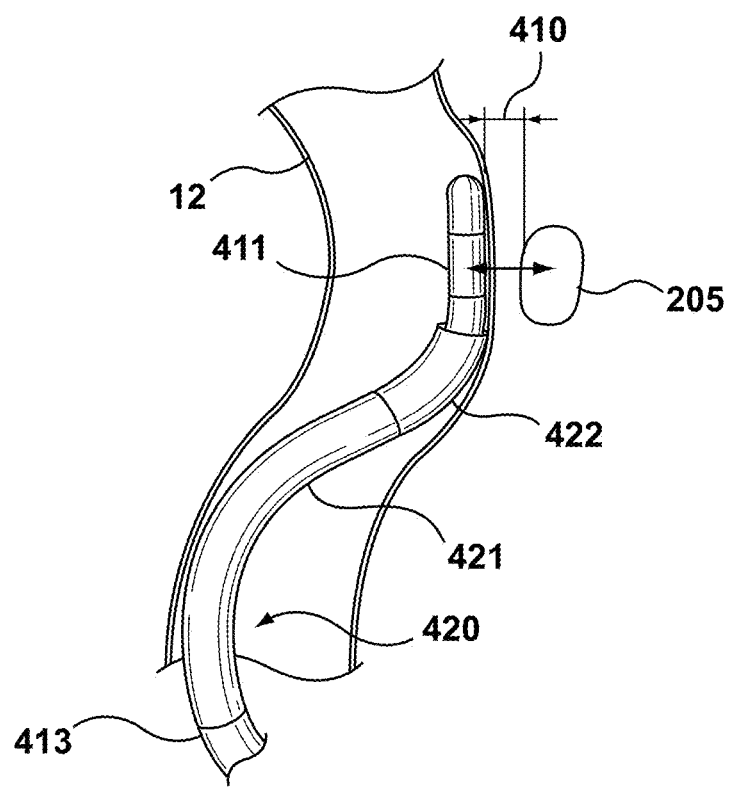

Alternatively, as shown in FIG. 21C a deflectable section 421 may be near a distal region of a deflectable sheath 420 and a soft passively deflectable section 422 may be at the distal end of the sheath. The soft, passively flexible section may provide an atraumatic contact with a vein wall while the sheath is deflected into the wall to manipulate the vein into a suitable position for carotid body ablation. The soft, passively flexible section may also allow the distal opening of the sheath to be aligned with the vein so that an ablation catheter delivered through the sheath exits the sheath sufficiently parallel to the vein wall as shown. The soft, passively flexible section may be made of a softer durometer (e.g., about 35 D durometer) polymer than the elongate section (e.g., about 63 D durometer) and the deflectable section (e.g. about 50 D durometer). The length of the passively flexible section may be in a range of about 1 to 3 cm (e.g. about 2 cm). The length of the deflectable section 421 may be in a range of about 2 to 5 cm (e.g. about 3 cm).

A method of using a deflectable sheath with an ablation catheter may comprise delivering a sheath from an entry vein such as a femoral vein to a vein proximate to a target, e.g., in an internal jugular vein, a facial vein, or other vein connected to a jugular vein that is in proximity to a carotid body. A catheter such as the embodiments described herein of ablation catheters or ablation catheters configured to be used with imaging catheters may be delivered through the deflectable sheath. An imaging modality such as an IVUS catheter positioned in an ablation catheter may be used to image tissue around the ablation catheter and identify a relative position of a target. If the vein needs to be manipulated to achieve a suitable position for ablation of the target the following steps or combination of steps may conducted: the deflectable section of the sheath may be deflected by controlling an actuator; the sheath may be torqued at the proximal end or handle to torque the distal deflectable end; the ablation catheter may be advanced or retracted in the sheath to obtain a suitable distance from the sheath's deflectable section to the ablation transducer; the ablation catheter may be torqued at its proximal end or handle to rotate the direction of aim of ablation; and if the ablation catheter is configured to be deflectable it may be deflected. Imaging may continue while manipulating the vein or imaging may be intermittently performed until a satisfactory position is obtained. Adjustments to the position and direction of aim of ablation may be made during or after the vein has been satisfactorily manipulated. For example, the ablation catheter may be rotated, advanced, retracted or deflected to aim ablation energy toward the target while imaging.

Transducer Assembly Configured for Both Imaging and Ablation

Figure 22:
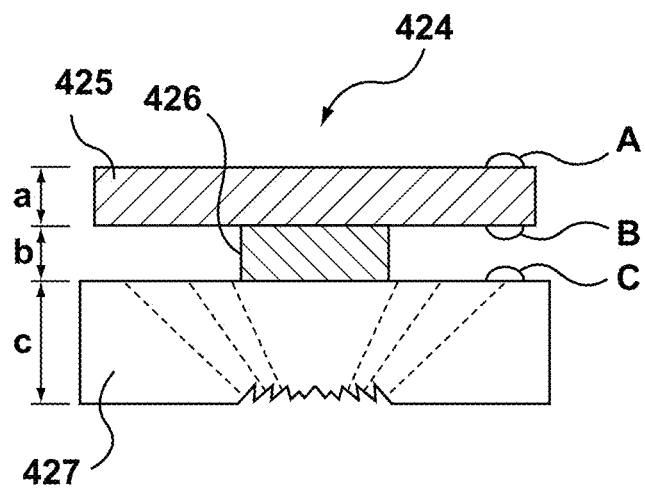
FIG. 22 is a schematic illustration of a transducer assembly configured for ablation and imaging.

An ultrasound ablation catheter may comprise a transducer assembly that is configured for both imaging and ablation. As shown in FIG. 22 a transducer assembly configured to allow imaging and ablation capabilities may comprise a first transducer 425, a second transducer 426, a backing member 427, and electrical conductors A, B, and C connected to the first and second transducers as shown. High power ablative vibration of the first transducer may be achieved by applying an RF signal to electrodes A and B in a frequency that is proportional to 1/a (e.g., about v/2a), where v is the speed of sound in the first transducer and a is the thickness of the first transducer. The second transducer, which may be one or multiple transducers, is sandwiched between the first transducer and the backing member providing a function of mounting the first transducer and imaging capabilities. The imaging at a lower frequency that is proportional to 1/(a+b) (e.g., of about v/2(a+b) or v/2b), where b is the thickness of the second transducer, is achieved by sensing the vibration of the transducer assembly through electrode pairs AC or BC respectively. The backing member of thickness c, where c is greater than a or b predominantly serves as a reflector in ablation mode and as an absorber in imaging mode. The outer surface of the backing member has surface features (e.g. texture, angled ridges) that scatters and redirects incoming signals away from the imaging transducer area thus reducing the ringing effect inside the backing member. The inner surface of the backing member may be flat and mirror polished to enhance reflectivity at an ablation operation frequency of about v/2a. The optional gap between the backing member, not otherwise contained by the second transducer, and the first transducer may be filled with air or liquid.

For example embodiments of ultrasound ablation catheters with integrated imaging transducers such as those shown in FIGS. 5 to 8 may comprise a set of imaging transducers as shown but instead of an ablation transducer the catheter may have a transducer assembly that can both image and ablate. This may allow the transducer assembly to generate an image of tissue precisely where the ablation will be directed. Likewise embodiments of ultrasound ablation catheters configured to accept a separate ultrasound imaging catheter such as those shown in FIGS. 11 to 20 may comprise a transducer assembly configured for both ablation and imaging.

Figure 23:
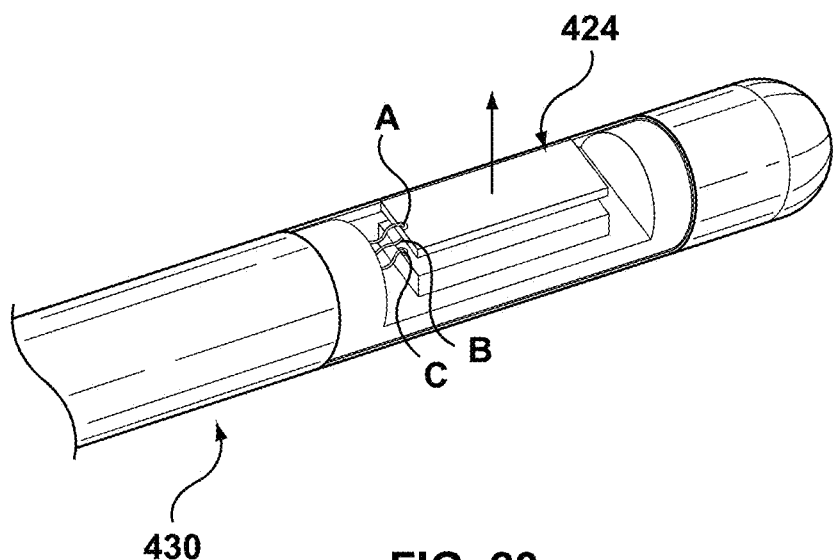
FIG. 23 is a schematic illustration of a catheter comprising a transducer assembly configured for both imaging and ablation.

Alternatively, as shown in FIG. 23 an ablation catheter 430 may be absent a set of imaging transducers or a means for accepting a separate ultrasound imaging catheter and only have a transducer assembly (FIG. 22) 424 configured for both imaging and ablation. In such a configuration it may be more difficult to see tissue surrounding the target compared to embodiments with separate imaging abilities but such a configuration may have an advantage in terms of cost and ease of use. Since the single transducer assembly has an ability to produce an amplitude mode line image compared to embodiments having circumferential imaging capabilities, a user may manipulate the catheter, for example by torqueing the catheter to sweep the transducer assembly side to side or advancing and retracting the catheter to obtain multiple line images of surrounding tissue. Alternatively a catheter may be configured to remain motionless while a transducer assembly with imaging and ablation functions is aimed in different directions from within the catheter. For example, the transducer assembly may be mounted to a rod passing through the catheter shaft that may be rotated 360 degrees or tilted within a predefined aperture, for example, within 90 degree angle. Alternatively the transducer assembly may be moved in multiple planes (e.g. pitch, yaw, swivel) from within the catheter. Such motion may be used to capture images of tissue surrounding the target, or to aim the transducer assembly at a target, or to move the transducer assembly to make multiply ablations, or sweep the transducer assembly to enlarge an ablation.

Ultrasound Ablation Dosimetry and Depth Control

Authors have conducted bench and animal studies to assess Dosimetry of ultrasound ablation energy using transducers with the size of about 2 mm in width and 4 mm to 6 mm in length. A power between 3 to 8 acoustic watts, a frequency in a range of about 10 MHz to 25 MHz and a time range of between 5 s to 20 s may allow a reasonable controllable lesion depth between 2 mm and 9 mm and lateral dimensions determined by transducer width and length suitable for targeting a carotid septum from a jugular vein (e.g. tissue residing at about 2-9 mm from the inner wall of the jugular vein).

The ability to control ablation depth is critical for the efficacy and safety of clinical procedure. In light of significant anatomical variation in relative location of the carotid arteries, carotid body and jugular vein, ablation depth control is essential for effective ablation of target tissue (e.g., carotid septum) while safely containing an ablated region to avoid iatrogenic injury of important non-target nerves or tissues. From the lesion formation theory a region of thermal coagulation induced by ultrasound heating is defined as an integral of temperature exponent over time [Sapareto S. A., Dewey W. C. Thermal dose determination in cancer therapy Int. J. Radiat. Oncol. Biol. Phys. 1984. V. 10. No. Bi P. 787-800]. A lesion produced by a flat rectangular element starts closest to transducer and propagates to deeper tissue that is more distant from the transducer along the ultrasound beam, depth over time. Using the thermal dose definition the theoretical lesion depth may be approximated by an integral over time:

$$d \sim \int_0^t e^T dt \quad (1)$$

Where d is depth of the lesion, T is tissue temperature, t is time. Based on finite element simulation the tissue temperature over time is roughly proportional to a product of applied acoustic power and ablation time:

$$T \sim Pt^\beta \quad (2)$$

Where $\beta$ is a tissue and transducer dependent dimensionless coefficient less or equal to one. Combining equations (1) and (2) in a simplest case of $\beta=1$, applicable for active ultrasound power deposition with negligible volumetric thermal conduction, the lesion depth as a function of applied acoustic power and ablation time is given:

$$d \sim \frac{e^{Pt}}{P} \quad (3)$$

The More complex forms of lesion depth growth over time can be deduced assuming $\beta$ deviates from unity, which corresponds to an ablation consisting of longer time and lower power in which thermal conduction effects cannot be neglected. Finite modeling of lesion formation provided theoretical data to evaluate different $\beta$ coefficients and deduce the trend between applied acoustic energy and lesion depth. It was found that lesion depth and applied acoustic energy are best described by hyperbolic cosine function:

$$E = Pt = \alpha \cosh(\gamma t) = \alpha \frac{e^{\gamma d} + e^{-\gamma d}}{2} \quad (4)$$

Where lesion growth parameter a is minimum acoustic energy required to initiate lesion nucleation and $\gamma$ is a characteristic lesion inversed depth parameter dependent on the transducer geometry, frequency and surrounding tissue anatomy.

The authors have determined through anatomical studies that a range of target ablation depths between about 2 mm to 9 mm may be suitable for delivering ablation energy to a carotid septum from a catheter placed in a jugular vein. Based on above theory, bench and animal studies the authors have demonstrated that a catheter delivering ablative energy from an ultrasound ablation transducer with a resonant frequency of about 21+/-2 MHz approximately 1 mm in lesion depth is gained for every 10 acoustic Joules of energy in a first approximation consistent with equation (3). Energy is a product of acoustic power and duration thus various regimes of controlling energy delivery parameters may be used to control ablation depth. For example, energy delivery parameters may be chosen to optimize multiple variables such as: minimizing duration to reduce risk of patient movement; utilizing a duration-power range in which lesion width or height are fairly consistent; utilizing a duration that is not too fast for a user or console to react to an event requiring adjustment of energy delivery for safety reasons; using a power that is not too high to have increased incidence of over heating; using a power that results in a reasonable transducer temperature increase that can be managed by coolant flow; minimizing duration to minimize conductive heating of adjacent tissues; utilizing parameters that allow control of lesion depth to about 0.5 mm precision.

A user may determine a desired ablation depth for example by assessing images from the ultrasound-based video created by the imaging transducer(s) that may have reference dimensions, and select the desired ablation depth on the ablation console. Alternatively, a computerized algorithm may assess a desired ablation depth automatically, for example based on the ultrasound-based video data, and relay the desired ablation depth to an ablation control algorithm of the ablation console. Alternatively, a computerized algorithm may assess relative positions of anatomical features such as internal and external carotid arteries and jugular vein and the ablation transducer and suggest a desired ablation depth to a user who may confirm or adjust the desired ablation depth to be entered into an ablation control algorithm. The ablation control algorithm may deliver ablative energy using energy delivery parameters suitable for creating the desired ablation depth.

Figure 24A:
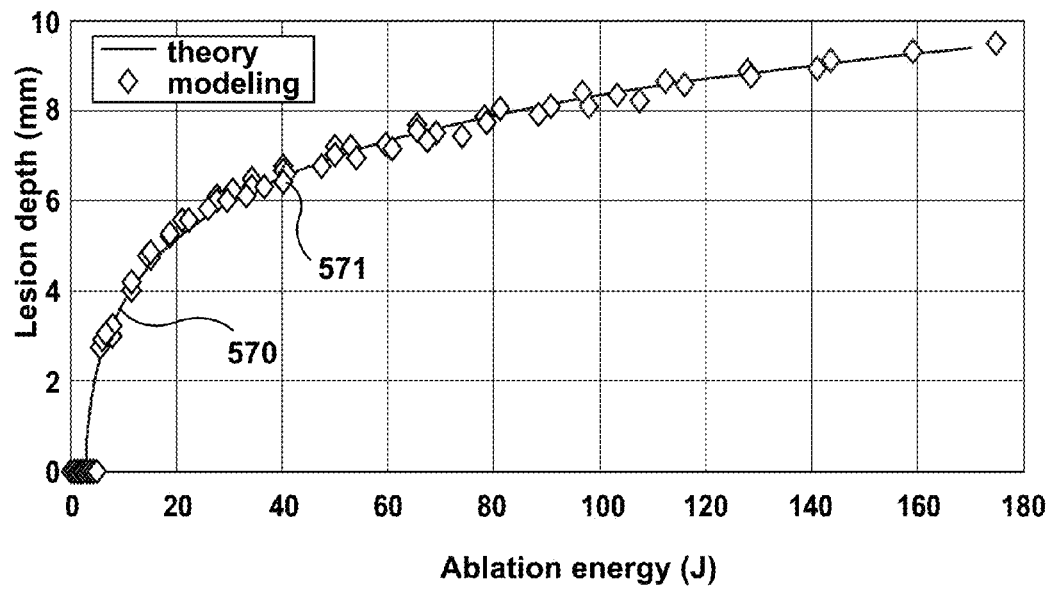
FIGS. 24A, 24B, are plots of lesion depth vs energy.

Using computer finite element modeling the authors have calculated dynamic temperature profiles for sets of ablation time (e.g., duration of energy delivery) and applied acoustic powers. Computed lesion parameters were consistent with experimental results and the theoretical trend expressed by equation (4). The results 571 of finite element modeling of lesion depth versus energy is shown in FIG. 24A. The line 570 shows the theoretical trend by equation (4) with lesion growth parameters: $\alpha=3$ Joules and $\gamma=0.5$ mm$^{-1}$.

Figure 24B:
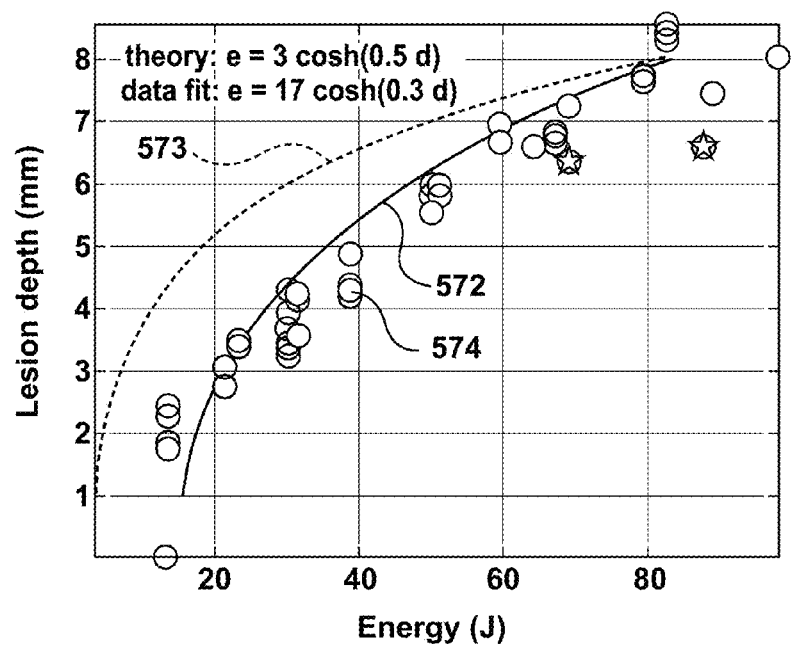

The accumulative effect of temperature is a thermal dose derived from the amount of energy deposited, which correlates with lesion formation dynamics. Determined predominantly by transducer dimensions the lesion lateral dimensions (e.g., length and width) increased relatively quickly and plateaued while lesion depth increased more slowly. Lesion width and length may be considered substantially constant within a range (e.g. a range of about 5 s to 25 s) of ablation duration considered in the sets of power and time used to control lesion depth. The 2 mm deep lesion is considered to be the minimum controllable lesion depth of desired lateral dimensions consistent with the transducer lateral dimensions (e.g., 2 mm wide and 4-6 mm long). For each set of ablation time and power, lesion depth was modeled creating a plot and equation (4) representing the relationship between lesion depth and applied acoustic energy as shown in FIG. 24B.

The generic theoretical relationship between lesion depth and acoustic energy was confirmed using bench test studies using a polyacrylamide gel phantom that produced data points of lesion depth for power-time sets, which were used to create a relationship of lesion depth as a function of energy that closely resembled the theoretical relationship. In overall, the theoretical relationship expressed by equation (4) provided an accurate fit to both simulated (dotted line 573) and experimental (circles 574 and solid line 572) data. Computer simulations predicted nucleation energy $\alpha=3$ J and characteristic inverse depth constant $\gamma=0.5$ mm$^{-1}$, while experimental data yielded larger $\alpha=17$ J and smaller $\gamma=0.3$ mm$^{-1}$. The difference in deduced lesion growth parameters reflects difference in thermal dose assumed in simulation versus visually detectable lesion formation in polyacrylamide gel. Gel turns opaque at slightly higher 70° C. temperature and has zero perfusion compared to typical 42° C. onset of protein denaturation temperature in biological tissue with nonzero perfusion assumed in simulations. Each catheter may have a slightly different ablation transducer response to electrical power delivery and may be calibrated using acoustic measurements to identify its specific relationship of electrical power to total acoustic power. Based on the relationship of ablation depth to sets of acoustic power and time and the calibration of electrical power to acoustic power of each catheter, a dosimetry table unique to each catheter may be created that matches desired depth to a set of ablation time and electrical power.

Figure 24C:
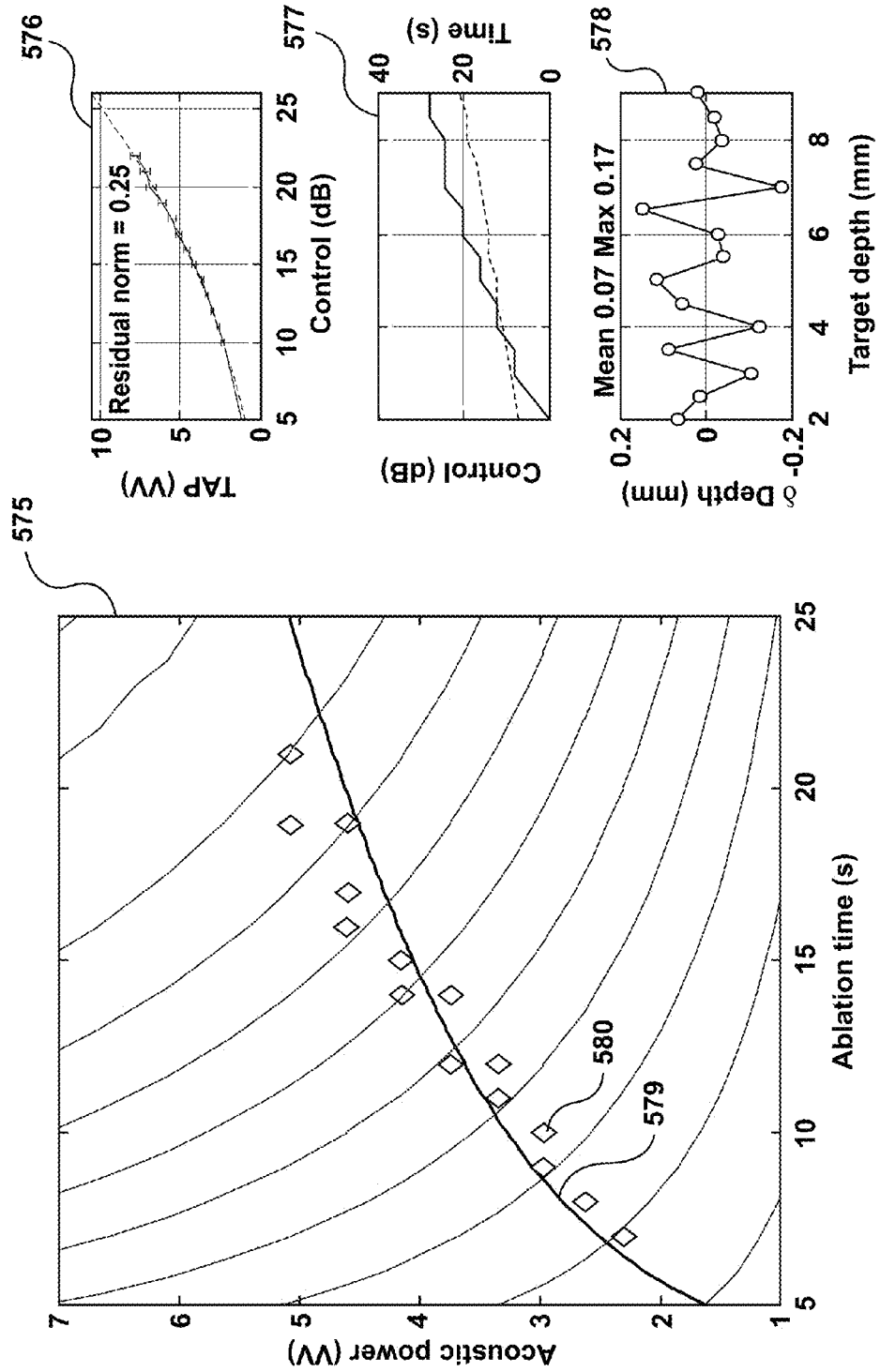
FIG. 24C is an example of an algorithm to determine dosimetry for a unique catheter.
Figure 26:
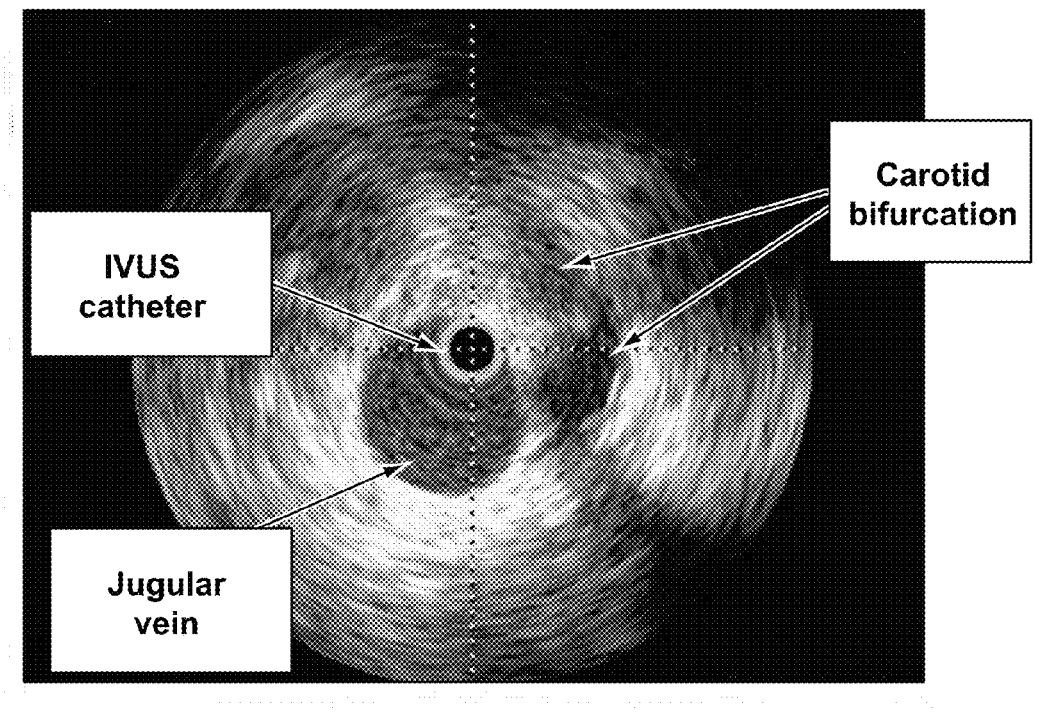
FIG. 26 is a frame of an ultrasound-based video taken by a catheter placed in a jugular vein proximate a carotid bifurcation.

An example of a dosimetry table-processing algorithm is shown in FIG. 24C. The algorithm assumes polynomial dependence of lesion depth from applied acoustic energy. The reference contours derived from equation (4) of different lesion depths in acoustic power-ablation time space are shown on the left panel 575 of the FIG. 24C. The panels on the right include the total acoustic power measurements of a catheter 576, deduced control power index and ablation times 577, and depth residual for target depth 578 are shown. An empirically derived ablation trajectory in acoustic power—time space is shown by line 579. A set of discrete, catheter-specific, power and time values are shown by white diamonds 580. The discrete set of acoustic powers and times arises from a limited ability of a generator system to control electric power and ablation time. While resolution in ablation time is limited by one-second interval, the discretization of the acoustic power depends on catheter specific acoustic power performance and ability of the generator to control electrical energy to 1 dB before amplification. The algorithm is concerned with finding a closest match to desired depth amongst catheter specific, generator discretized power and time values that fit an optimal acoustic power—time trajectory. The optimal trajectory is defined as parabola with an origin at point A and tangent at point B, where point A corresponds to the lowest acoustic power above 2 watts at 5 seconds, and point B corresponds to the highest acoustic power below 6 watts at 25 seconds. The algorithm utilizes two inputs: first, experimentally and theoretically deduced generic lesion depth dependence on acoustic energy, second, catheter specific, acoustic power dependence on generator system control index. The algorithm finds an optimal generator power index and time pairs for each desired depth that fit a chosen ablation trajectory by minimizing the function F:

$$F=\sqrt{\alpha\delta P^2+\beta\delta t^2+\gamma\delta d^2} \qquad (5)$$

Where $\delta P$ and $\delta t$ are acoustic power and time deviation from optimal trajectory, and $\delta d$ is deviation from optimal depth, $\alpha=4$, $\beta=1$, $\gamma=1$ are constants.

An example of a dosimetry table for a specific catheter is shown in FIG. 25. The first column of the dosimetry table constitutes a target lesion depth, the second column lists a respective electric power control index translated by generator system software in electrical power delivered to a transducer, the third column is a set of respective ablation times (duration). Additional columns list auxiliary information for verification and quality control purposes. The unique ablation dosimetry table may be programmed in a memory storage component such as an EEPROM in the specific catheter. In use when a specific catheter is electrically connected to an ablation console a computerized algorithm in the console reads the ablation depth table unique to that catheter from the memory storage component and when ablation depth is selected either automatically or manually, the algorithm selects the corresponding power—ablation time settings and deliver energy to the catheter using said settings to create the desired ablation depth.

Increasing Ablation Size

Ablation width is typically tied to ablation depth. Controllably creating a wider ablation may result in creating a deeper ablation. Ablation energy delivered from a catheter positioned in a vein (e.g., jugular vein) and aimed at a carotid septum may have a depth dimension that is oriented from a lateral to medial boundary of a carotid septum. The depth of an ablation may be optimized to cover the distance between these boundaries and it may be desired to avoid ablating beyond the medial boundary to reduce a risk of ablating an important non-target structure. With an optimized ablation depth the width may only cover a fraction of a carotid septum width depending on the anatomy of the patient. It may be desired to ablate a larger percentage of a carotid septum to increase efficacy. Ablation size (e.g., width or height) may be increased without increasing ablation depth by moving the ablation transducer and optionally the imaging transducer along with the ablation transducer. For example, motion of an ablation transducer may be accomplished by side-to-side deflection of the distal region of an ablation catheter, rotating the catheter or transducer within a catheter, or translational motion of a catheter or transducer along a length of a vessel. Motion may be performed to create multiple independent ablations or during energy delivery to spread a resulting ablation over a greater volume. Motion may be preformed while imaging wherein a user may identify boundaries of a desired target zone or an ablation may be computer controlled by detecting target zone boundaries and applying ablation energy only within the boundaries. Boundaries may include for example anatomical structures such as boundaries of a carotid septum. Motion of a transducer in a catheter may be accomplished manually by a user or automatically by a servomotor connected to a rotatable transducer mount that is computer controlled with a desired speed and distance and may comprise a feedback signal such as edge detection to identify a target zone. An alternative way to increase ablation size may be to direct ablation energy through a lens to diffuse or diffract energy. A lens may be inflatable with a liquid such as water or saline to adjust a desired diffusion or diffraction. Another alternative for creating wider ablations may include delivering ultrasound ablation energy from a transducer having a convex curved surface. A user may choose a catheter having a suitable curved transducer for a desired ablation width depending on a patient's anatomy. Alternatively, a catheter may have a convex curved transducer and a shield with an aperture that is adjustable to customize ablation width.

Air Bubble Elimination

The embodiments described herein that contain an echolucent chamber with flowing coolant may be adapted to reduce or eliminate air bubbles in the coolant. Air bubbles can inadvertently become included in the supply of liquid coolant (e.g. saline or water). Through surface tension, air bubbles may stay trapped in an echolucent chamber or form during energy delivery near or on an ultrasound transducer. This may negatively affect ablation or imaging performance. In the manufacture of a catheter a solution (e.g. isopropyl alcohol) carrying a surfactant may be circulated through the coolant delivery pathway and echolucent chamber, the solution may be drained and the catheter left to dry. The surfactant may be retained on the fluid-contact surfaces making all surfaces wettable, i.e. having a reduced surface tension that facilitates the removal of air bubbles.

Contrast Enhanced Ultrasound Imaging to View a Carotid Body

Any of the methods of use herein may comprise ultrasound contrast enhanced imaging, which may improve the ability to image a carotid body. An ultrasound contrast, such as commercially available SonoVue, may contain microbubbles. Differential image analysis may be performed by taking an image of the target area using an ultrasound imaging transducer (e.g., on an imaging catheter or an external ultrasound transducer) before and after injecting ultrasound contrast and comparing the images to highlight contrast from the non-contrasted tissue. The contrast may be injected into the patient's vascular system by injecting through the sheath, which may have a gasket seal on the proximal end to seal around the ablation catheter, an injection port such as a luer lock with a stopcock valve through which contrast or other injectant may be injected into the sheath's lumen in the space around the ablation catheter to be deposited out the distal end of the sheath. Areas containing the contrast typically would be areas with blood flow, including a carotid body. If a precise location of a carotid body can be identified with imaging technology such as contrast enhanced ultrasound imaging, CT or MRI, then a target ablation area may be narrowed to the carotid body. If a precise location of a carotid body is not identified a target ablation area may include a larger zone such as an intercarotid septum.

Ablation Transducer Backing

An ablation catheter may comprise an ablation transducer acoustic insulator or backing component. An ablation transducer may transmit ultrasound waves in multiple directions. For example, a plate shaped transducer whether it is substantially flat or curved may transmit ultrasound energy from both faces of the transducer. The backing component may be used to shield transmission of ablation energy so ablation energy is only directed from one face of the ablation transducer and may further serve to reduce acoustic losses.

A backing may be acoustically absorptive or reflective. A backing element may be a component containing a thin layer of gas such as air or carbon dioxide having a thickness of at least about 1 mm. The acoustic insulator may be a dense material such as stainless steel, for example having a thickness of at least about 0.006" (e.g., about 0.008").

An embodiment of an acoustic insulator containing gas comprises microspheres of air that are embedded in a substrate such as epoxy. An acoustic insulator made from air-filled microspheres embedded in epoxy may have less of a mechanical coupling effect when a transducer is placed in contact with the acoustic insulator compared to an acoustic insulator made from brass or stainless steel. In other words the vibration of the transducer may be dampened significantly less when a transducer is placed in contact with a microsphere insulator than when it is placed in contact with a dense, rigid insulator such as stainless steel or brass. Thus an air-filled microsphere acoustic insulator may be more suitable in an embodiment where a transducer is positioned in contact with the acoustic insulator. Such a design may have benefits such as ease of manufacturing, less fragile transducer, smaller catheter diameter, or more space for coolant flow in front of the transducer. A combination of microspheres having a variety of diameters may increase volume of air in an insulator. For example smaller microspheres may occupy space between larger microspheres. An acoustic insulator may have a thickness in a range of about 200 to 300 microns (e.g., about 250 microns) and may contain a combination of microspheres having diameters in a range of about 15 to 25 microns (e.g., about 20 microns) and microspheres having diameters in a range of about 180 to 210 microns (e.g., about 200 microns), for example.

Fiducial Marker to Create an Aiming Artifact

For embodiments described herein comprising one or more imaging transducers an fiducial marker may be positioned in the ablation catheter to interact with the imaging ultrasound waves to provide a distinguishable aiming artifact on the ultrasound-based video that identifies a relative position to the direction of delivery of ablation energy. A fiducial marker may have acoustic properties that are significantly different that the surrounding tissue for example so echoes are greater (hyperechoic) or less (hypoechoic) than the surrounding tissue. The material or surface of the fiducial marker may be highly reflective or highly absorptive of sound waves relative to surrounding tissue being imaged. A fiducial marker may have a more consistent echo compared to surrounding tissue being imaged. A fiducial marker may be positioned to indicate on an ultrasound-based video the opposite direction of delivery of ablation energy. In this configuration the image of the aiming artifact (e.g., a shadow) will not interfere with the image of the target region and surrounding tissues. The image of the aiming artifact on an ultrasound-based video may be a distinguishable shape such as a wedge or line that is black or white radiating from the center of the ultrasound-based video in one direction and a user may understand that the ablation energy is aimed in an opposite direction.

Other relative directions or arrangements of fiducial markers may be envisioned. For example, two fiducial markers may be positioned on either side of an ablation transducer to indicate that ablation energy is delivered between two resulting aiming artifacts. Alternatively, two thin fiducial markers may be positioned close to one another to create an image resembling two bright stripes bordering a narrow stripe, which may be a more precise and detectable aiming artifact. Alternatively a fiducial marker may be placed at other positions around a circumference of a catheter as long as its relative position to a direction of aim of ablative energy is understood.

A fiducial marker may comprise a material that interacts with imaging ultrasound waves to absorb or reflect ultrasound waves in a distinguishable manner compared to typical tissue in a target region. For example, the material may be a dense material such as stainless steel or an air-filled component that inhibits transmission of ultrasound. In some embodiments, an fiducial marker may be a component that also acts as a backing material for an ablation transducer that also inhibits transmission of ablation energy. In other embodiments a fiducial marker may be a separate component or may provide other functions such as structural support for a distal end component, a guide wire lumen, or an echolucent shell support.

An embodiment of a fiducial marker comprises a stainless steel hypotube with a lumen containing air or air-filled microspheres held in epoxy. The hypotube may be sealed at both ends with an adhesive to contain the air or microspheres. The hypotube may have an outer diameter of about 0.028" to 0.038" for example.

Another embodiment of fiducial marker comprises a wire such as a round wire (e.g., having a diameter of about 0.028" to 0.038"), or a flat ribbon wire (e.g., having a profile of about 0.005" by 0.030"). The wire may be stainless steel. Optionally, the wire may be surrounded by a component that further interacts with ultrasound imaging waves, for example a metal coil may be wrapped around the wire or the wire may be coated in an epoxy containing microspheres of air.

A fiducial marker may have increased echogenicity to increase its distinctive characteristics compared to surrounding tissue. For example, a fiducial marker may comprise a rough surface or a linear pattern of grooves or surface with a texture that enhances reflectivity of ultrasound waves. This may be particularly helpful when an imaging transducer is not parallel to the fiducial marker. Some IVUS catheters comprise transducers that are positioned at a slight angle to axis of the catheter. Although the angle may be small it may cause waves to reflect off of the fiducial marker at an angle of incidence that reduces the ability of the transducer to capture echoes.

A fiducial marker may comprise a piezoelectric element that vibrates when high frequency current is applied emitting an acoustic signal that may be detected by the imaging transducer to provide a robust image of the fiducial marker.

Image Augmentation

Figure 30:
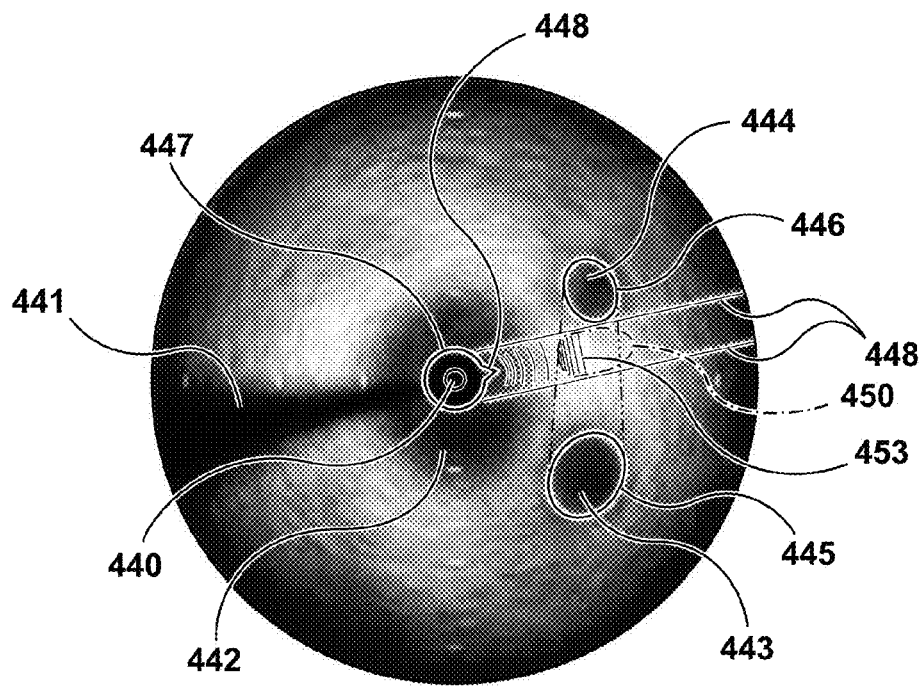
Figure 31:
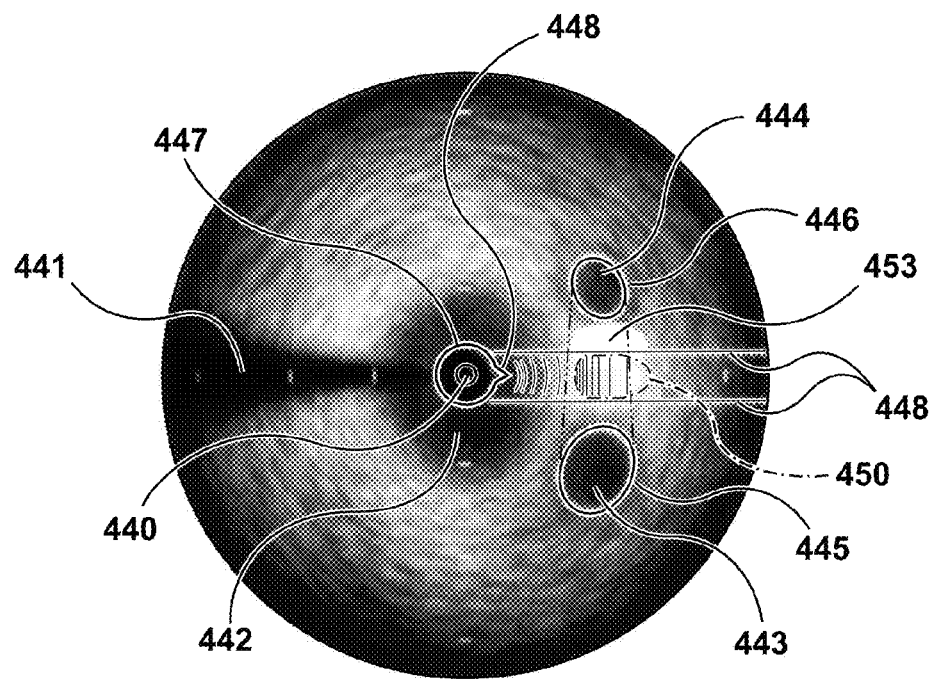

A system for imaging a target region and ablating tissue in the target region may provide a digital video, or ultrasound-based video, created from ultrasound signals transmitted from an ultrasound imaging transducer, reflected off of tissues, and received by the imaging transducer. An example of a frame of an ultrasound-based video created with an IVUS catheter placed in a jugular vein in proximity to a carotid bifurcation is shown in FIG. 30.

An ultrasound-based video may be further augmented with visual aids, animations, or messages to provide information to a user that may assist understanding of the ultrasound-based video, planning or conducting a carotid body ablation procedure.

Figure 27:
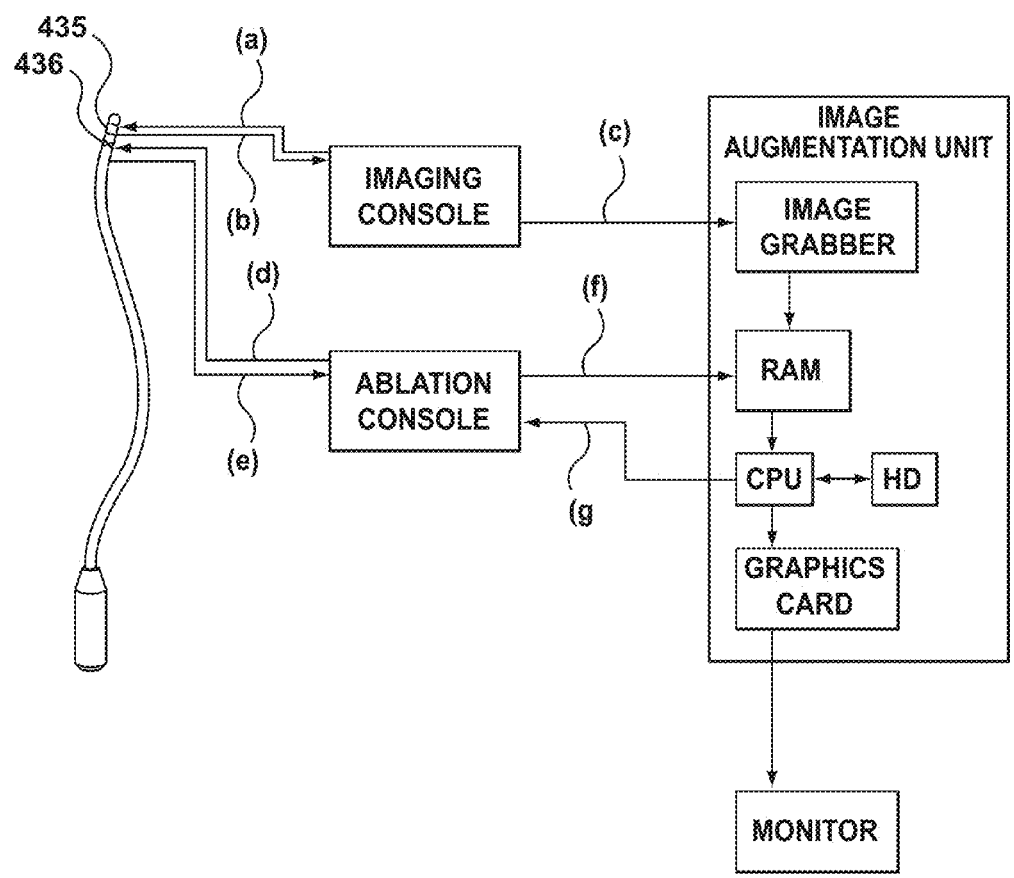
FIG. 27 is a block diagram of a system for imaging and ablation.
Figure 28:
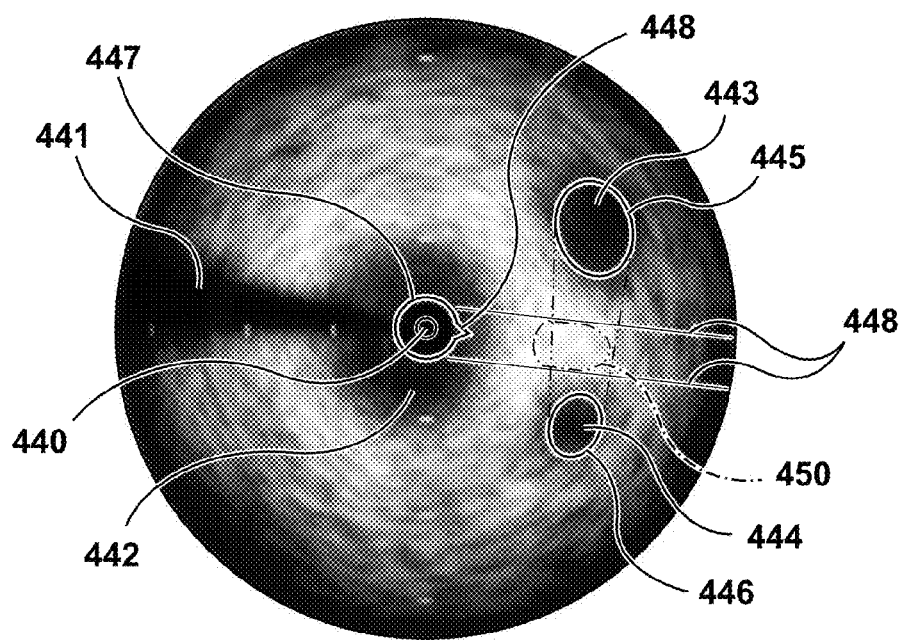
FIGS. 28 to 31 are schematic illustrations of augmented ultrasound-based videos.
Figure 29:
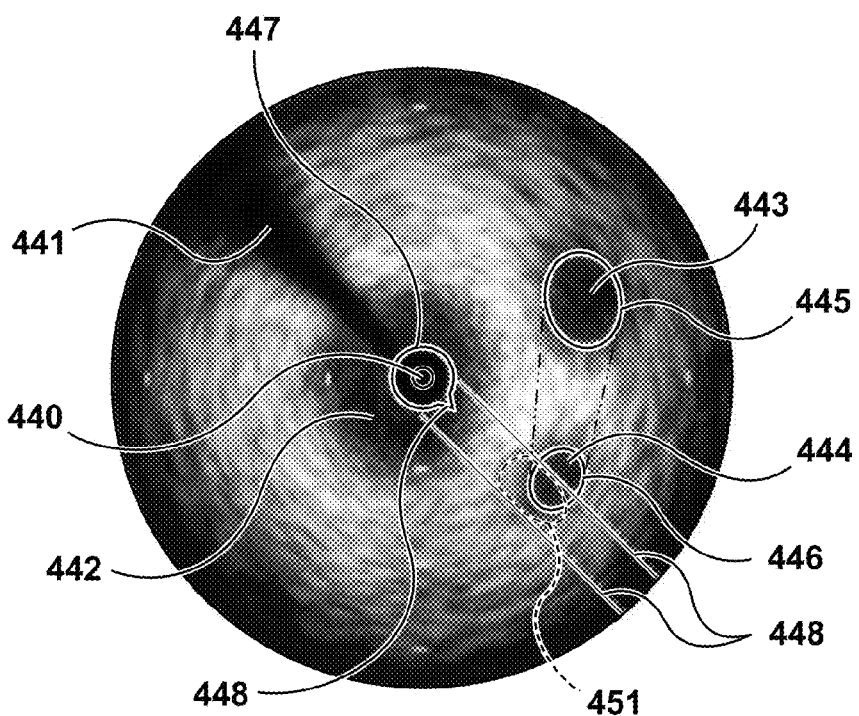

An embodiment of a system for imaging and ablation of a carotid body having image augmentation may comprise a catheter with an ultrasound imaging transducer and an ablation means, an ablation console, an ultrasound imaging console with a means for transmitting and receiving signals to and from the imaging transducer and a computer executed algorithm that creates an ultrasound-based video from signals received from the imaging transducer, an image augmentation unit that processes the ultrasound-based video with a computer algorithm that creates an augmented image, and a monitor to display the augmented image. A schematic diagram of a system is shown in FIG. 27. The image augmentation unit hardware may comprise an image or frame grabber, RAM, a CPU, storage such as a hard drive, and a graphics card. The imaging console may (a) send an ultrasound imaging signal to the imaging transducer 435, (b) receive an echo signal from the transducer, and (c) send an ultrasound-based video signal to the image augmentation unit. The ablation console may (d) send ablation energy to the ablation element 436 (e.g., ultrasound ablation transducer), (e) receive feedback from a sensor in the catheter such as a temperature sensor, (f) send information (e.g., ablation status, energy delivery parameters, user interface controls, information to be displayed on the monitor) to the image augmentation unit, and (g) receive information (e.g., to control ablation status, to control energy delivery parameters) from the image augmentation unit. The image augmentation unit may also (h) send a video to a monitor.

The catheter may be an embodiment described herein of an ablation catheter configured to accommodate an ultrasound imaging catheter or with an integrated imaging transducer(s) and may further comprise an aiming artifact to identify a direction of delivery of ablation energy on an ultrasound-based video. An ablation means may comprise an ultrasound ablation transducer or other ablation energy delivery device such as a needle that penetrates a vessel wall to deliver RF energy or a chemical agent to an ablation target tissue. The system may further comprise an ablation energy console suitable to the ablation means such as an ultrasound generator or RF generator.

The imaging transducer, or transducer, may be for example a piezoelectric or capacitive transducer positioned in or on a distal region of the ablation catheter near an ablation element (e.g. ultrasound ablation transducer, RF needle, needle for injecting a chemical agent, RF electrode, laser emitter). The imaging transducer may transmit acoustic waves to the space around the distal region of the catheter and receive acoustic waved echoed off of tissue in the space.

An ultrasound imaging console may generate an electrical signal and control delivery of the signal to the imaging transducer to be converted to ultrasound waves. Echoes received by the imaging transducer may be converted to an electrical signal, which is transmitted back to the imaging console. Some embodiments may use separate transmitter and receiver components or consoles. In some embodiments an imaging transducer may be positioned on an IVUS catheter (e.g. Visions® 0.035 catheter by Volcano Corporation, or Ultra ICE® catheter by Boston Scientific) and an ultrasound imaging console maybe a system compatible with the IVUS catheter. An IVUS catheter and compatible imaging console may be provided separately from the system, which may be configured to accommodate the IVUS catheter and imaging console. In another embodiment an imaging transducer may be integrated in an ablation catheter, an imaging console may be separate from an ablation energy console or may be integrated into a single unit, and both the imaging transducer and imaging console may be provided as part of the system.

The electrical signals generated by the echoes impacting the transducer and transmitted back to an imaging console may be used to create an image or video (i.e. ultrasound-based video) that may be displayed on a monitor. For example the signals may be processed by a computer-executed algorithm and output to a monitor or a video output port on the ultrasound imaging console.

Image grabber hardware, used to capture images or video, is known in the art and may consist of a hardware interface that captures single frames of video, converts the analogue values to digital and feeds the result into a computer. The image grabber may be connected to the video output port on the ultrasound imaging console, for example, and may send a digital interpretation of the video to an image augmentation computer, which may be incorporated into the ultrasound ablation console or be a separate unit.

The image augmentation computer may run an algorithm to augment the video. The algorithm may process each video frame in real time tracking the orientation of the ablation catheter using a fiducial marker or aiming artifact in the images. The algorithm may identify an aiming artifact by looking for any distinct marker that does not change shape when the orientation changes. Inputs to the algorithm may be provided by the ultrasound-based video, the ablation console (e.g., console status, energy delivery status, depth parameters), or a user interface (e.g., identification of anatomical features, settings, zoom, pan, contrast, features to display). Outputs may be to a monitor (e.g., an augmented image, an original ultrasound-based video, an augmented image overlaid on an ultrasound-based video), or to an ablation console (e.g., signal to control energy delivery, signal to control energy delivery parameters such as power and time).

In addition to the captured video, a user may control inputs to the algorithm. For example, a user may select a desired ablation depth or identify a part of the anatomy such as an internal carotid artery or external carotid artery. User inputs may be controlled by a user interface (e.g. knobs, dials, touchscreen, mouse, voice control) that may be on the unit containing the image augmentation computer (e.g. the ablation console). Before delivering ablation energy, a user may adjust ablation depth on the ablation console, for example if the overlaid image of an estimated ablation appears to be too long and extend beyond the borders of a carotid septum, or too short and not fill a carotid septum adequately, and the overlaid image of an estimated ablation may reflect the adjusted depth. In an embodiment wherein the ablation element is an ultrasound ablation transducer ablation depth may be controlled by automatically adjusting parameters such as power and time for a given frequency.

The image augmentation algorithm may output a signal to a monitor. For example, if the algorithm is on a computer physically contained in an ablation console the output may be to an output port (e.g., a VGA, SVIDEO, DVI, HDMI port) or cable connected to an external monitor or to a monitor on the ablation console. An external monitor may be supplied with the system or separately as part of a catheter lab's equipment. The monitor may display other information in addition to the ultrasound-based video with augmented image overlay such as fluoroscopy or X-ray, patient information, or physiological parameters.

Black and white versions of embodiments of augmented video frames are shown in FIGS. 28 to 31. The algorithm may identify an expected image of the imaging catheter which may be generally a dark circle 440 in the center of the image, and an aiming artifact which may be generally a distinctive (e.g., dark or white) wedge 441 radiating from the center of the image. An aiming artifact, for example produced by a fiducial marker or a synchronized aiming emission, may be particularly useful in embodiments wherein a separate imaging catheter is inserted into an IVUS lumen of an ablation catheter. Alternatively, for embodiments wherein imaging transducers are integrated with an ablation catheter an aiming artifact may be produced by a fiducial marker, a synchronized aiming emission, or by omitting an imaging transducer in a direction relative to the direction of aim of ablation energy, or instead of an aiming artifact the direction of aim may be programmed into the imaging algorithm and displayed on an ultrasound-based video. A user may deliver the catheter containing the imaging transducer through vasculature to a region proximate a carotid bifurcation using fluoroscopic imaging guidance. In the example shown in FIGS. 28 to 31, a catheter is delivered through a venous approach to a region near a carotid bifurcation. The algorithm may be programmed to expect anatomy based on a catheter delivery approach. In the example shown the algorithm may expect that the dark circular shape 442 around the imaging catheter in the center of the image is an internal jugular vein 12 and two dark circles 443 and 444 in the region within a size range of about 3 to 8 mm may be carotid arteries. If an imaging system is capable of imaging other anatomical features such as a carotid body or carotid nerves or non-target nerves, they may be identified as well. As shown, the augmented image may comprise an overlay of images on the ultrasound-based video such as an outline of a carotid artery (e.g. common carotid artery, internal carotid artery 445, external carotid artery 446), an outline of the ablation catheter 447, an arrow 448 indicating a direction of delivery of ablation energy or a direction that the ablation element is facing or will deliver ablation energy. In the embodiment shown the ablation element may be an ultrasound ablation transducer and the augmented image comprises lines 449 indicating estimated lesion width projected in the direction of delivery of ablation energy. The augmented image also comprises an outline of an estimated ablation 450 in a location where it is expected to be created. The estimated ablation outline may be distinguishable 451 (e.g. red, shown in a dashed outline in FIG. 31) if it is positioned in an unsuitable region, for example if it is not within the borders of an intercarotid septum, if it is contacting or too close to a carotid artery, or if it is at a position where an ablation was previously made. The estimated ablation outline may be distinguishable (e.g. green, shown as a dash-dot outline 450 in FIG. 28) if it is in a position ideal for creating an ablation, for example between carotid arteries in an intercarotid septum.

To confirm identification of the internal and external carotid arteries the user may be asked to slowly slide the catheter out and in by a few centimeters, which may create an video of the two carotid arteries converging to a common carotid artery as the catheter is pulled out and diverging to internal and external carotid arteries as the catheter is pushed in.

As shown in FIG. 30 when ablation energy is being delivered the augmented image may display an animation to indicate energy delivery for example a pulsing, colored light (shown in FIG. 30 as lines 452). An animation may be displayed that indicates progression of time through the duration of an ablation, for example growing color bar (shown in FIG. 30 as lines 453) can fill in the estimated ablation outline wherein an empty outline indicates time=0 s and a full outline indicates a complete duration.

Figure 33:
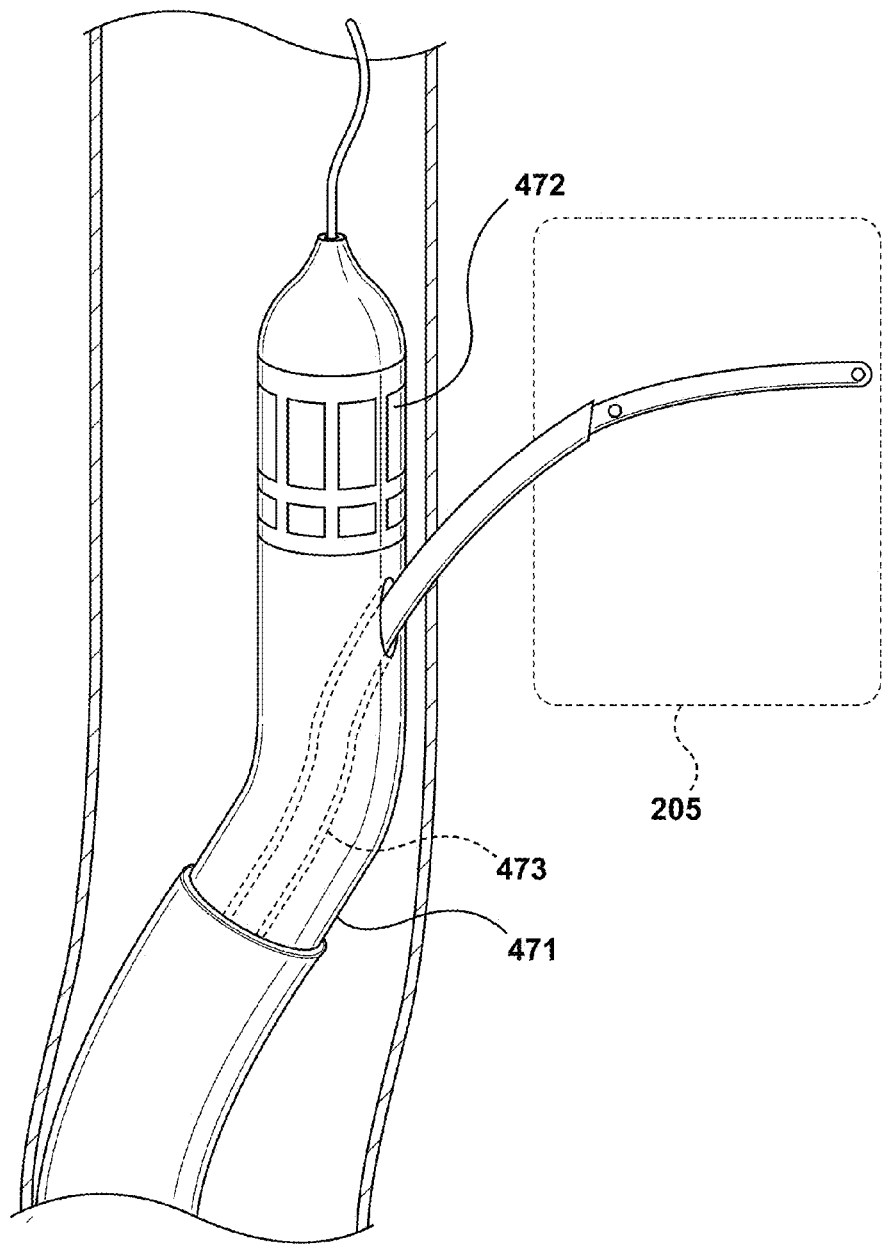
FIG. 33 is a schematic illustration of an ultrasound image guided needle ablation catheter.

After an ablation has been created an image of the ablation 453 with respect to the carotid arteries may be displayed, for example with distinct color such as white as shown in FIG. 33, which displays a completed ablation and a second ablation under way.

The information computed by the image augmentation algorithm could be fed back to the energy delivery console.

If there is inadvertent movement during delivery of ablation energy the augmented image algorithm may send a signal to the ablation console to pause or discontinue delivery of ablation energy and the augmented image may display a partially filled ablation outline in a color such as red to indicate a suitable time may not have been achieved to create a desired ablation depth and a user may chose to preform another ablation in the same location.

If the catheter is pushed forward or pulled back the image augmentation algorithm may calculate translational movement using the change in distance between the internal and external carotid arteries.

Information from other imaging sources such as fluoroscopy, MRI, CT, or a second ultrasound imaging transducer may be input into the image augmentation algorithm and may be used to create an image of location of a carotid body or nerves, to calculate bifurcation angle, to create a 3D image, or to calculate height of an ultrasound imaging plane above a carotid bifurcation.

Another fiducial may be used to identify distance from a carotid bifurcation (e.g. distance in a superior direction to a carotid bifurcation). For example a fiducial marker may be a wire that is slidable within a lumen of the catheter. The wire fiducial may have a distinguishable echogenic marking that may be aligned with a carotid bifurcation. The wire fiducial may be held in place as the catheter is advanced. The wire fiducial may have another distinguishing marking at a predetermined distance from the first marking (e.g., about 6 mm from the first marking). When the catheter is advanced until the second marking is seen it may be understood that the imaging plane is the predetermined distance (e.g., 6 mm) from the bifurcation. The wire fiducial may have multiple markings to indicate increments (e.g., every 2 mm). The wire fiducial may also have radiopaque markings that can be visualized on fluoroscopy.

The algorithm may control rotation of the image so the augmented image may be displayed for example, with the direction of aim always up.

An image augmentation algorithm may use a known dimension such as diameter of the catheter or width of an aiming artifact as a scale and calculate distances between anatomical features for example, relative positions of an internal jugular vein, a carotid septum, an internal carotid artery, an external carotid artery, carotid septum boundaries, artery diameters, change in artery diameters, change in relative position of anatomical features, size and relative position of an estimated ablation or created ablation. Calculated distances may be displayed on an augmented image overlay, for example, as a list or with labels. The algorithm may provide user instructions or suggestions based on calculated distances, for example, how much to torque or deflect the catheter to manipulate the vessel (e.g., jugular vein) containing the catheter, how much and which direction to torque the catheter to adjust aim of the ablation element, adjustments to ablation depth or parameters affecting ablation depth, how to move the catheter in or out of the vessel to achieve a suitable position.

An image augmentation algorithm may input information to the ablation console. For example, measurements and relative positions calculated by the image augmentation algorithm may be used to automatically adjust parameters (e.g., power and time) to control ablation depth so the estimated ablation size is optimally within and filling space between medial and lateral borders of a carotid septum. The image augmentation algorithm may detect significant movement during ablation that may send a signal to the ablation console to pause or terminate delivery of ablation energy.

Ablation may be performed in a sweeping mode where ablation energy is delivered while moving the aim, for example rotating an ultrasound ablation transducer to sweep across a carotid septum from one carotid artery to another. An image augmentation algorithm may indicate to a user when to move or how fast to move the aim and may signal the ablation console to pause energy delivery when a significant amount of energy is delivered to a position then continue to deliver energy when the image augmentation algorithm detects movement to a suitable position. Alternatively, motion of ablation aiming may be controlled by a mechanism such as a servomotor controlled by input from the image augmentation algorithm based on calculated measurements and relative positions.

Movement Detection

Ablative energy, particularly ultrasound ablation energy, may be delivered for a duration of less than about 30 s (e.g. less than about 25 s, less than about 20 s, between about 7 to 23 s). While ablative energy is being delivered the direction of aim of ablative energy may move inadvertently from a desired target direction. This may cause a risk of creating an ineffective ablation in the desired target tissue, or injuring a non-target tissue. A number of methods of mitigating these risks are disclosed.

Movement of the directed ablation energy from the target tissue may be caused for example by patient movement (e.g., sudden or slow movement, caused by moving the head, coughing, sneezing, flinching), or movement of the catheter or a component external to the patient connected to the catheter.

Detection of potential movement of the directed ablation energy from the target tissue may comprise the following: monitoring movement of the patient's body or head manually by a user or automatically with image tracking or sensors such as an accelerometer; an imaging algorithm or image augmentation algorithm may be programmed to identify movement that is significant to increase risk; a sensor such as an accelerometer or multiply accelerometers may be positioned in an ablation catheter such as those disclosed herein; a 3D orientation and tracking system for example using a magnetic or electric field to detect a magnetic coil or electrode positioned in an ablation catheter may be used to track the device within a patient's body.

Mitigation of a risk of movement may involve the following methods: a user may manually disengage energy delivery if movement is detected; a user may be required to hold an actuator in an on position to deliver energy and may react quickly to movement by releasing the actuator; automatic patient movement detection may input to the energy delivery console to cease or adjust energy delivery; an imaging or image augmentation algorithm detecting significant movement may send a signal to the energy delivery console causing it to cease or adjust energy delivery.

Upon stopping or adjusting energy delivery, an energy delivery console may display a message to a user that the delivery of energy was cut short due to potential movement risk. The message may further display how much of the procedure was completed.

Ultrasound Imaging Guided Interstitial Ablation Needle

Figure 32:
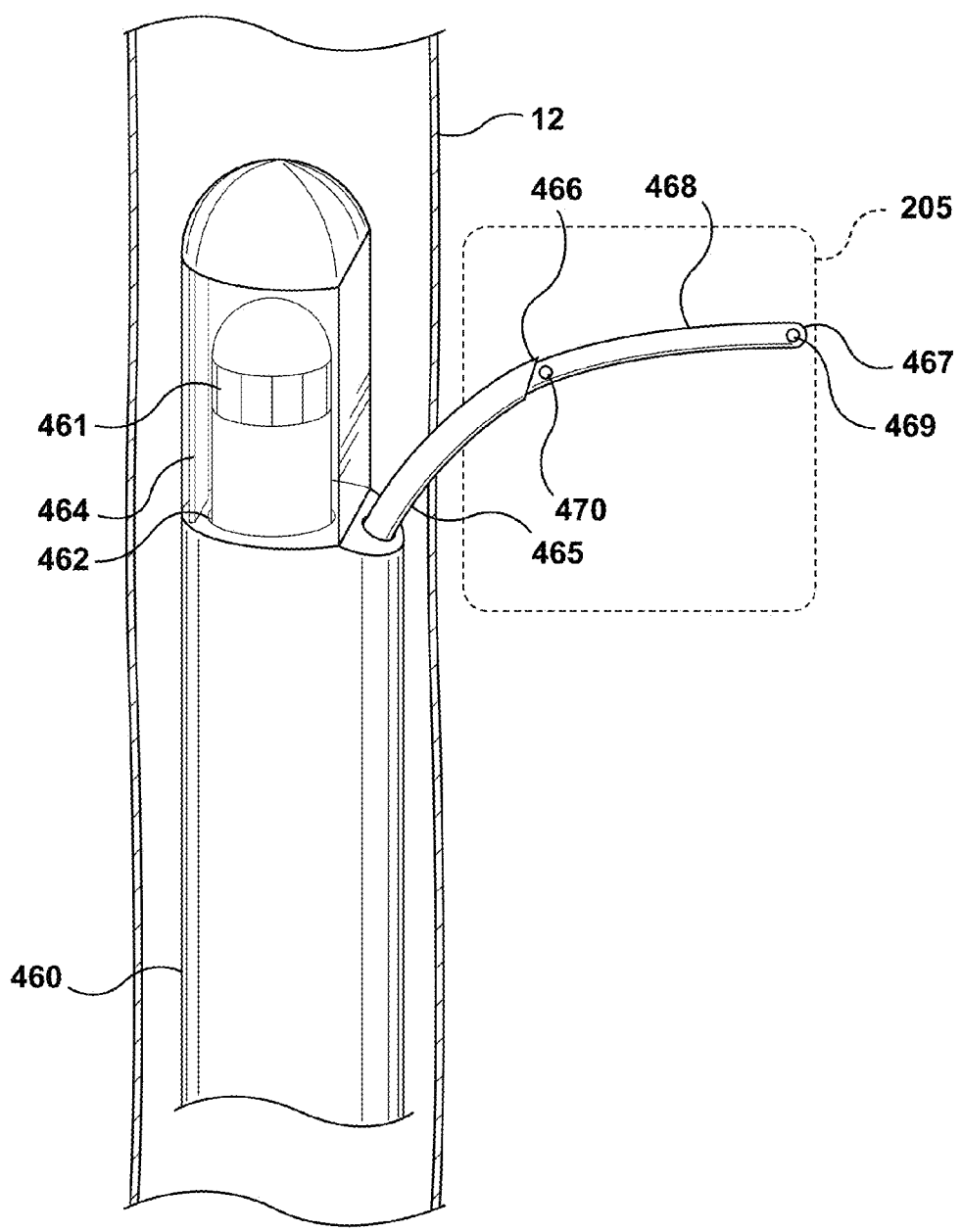
FIG. 32 is a schematic illustration of an ultrasound image guided needle ablation catheter.

Many embodiments disclosed herein comprise high-energy ultrasound as an ablative energy. Alternative embodiments of an endovascular catheter with imaging capabilities may comprise other forms of ablative energy to ablate target tissue (e.g., tissue in a carotid septum) near a vessel (e.g. jugular vein). An ultrasound imaging guided needle ablation catheter (ablation catheter) may combine an endovascular ultrasound imaging transducer for detecting a target (e.g.

carotid septum, carotid body) and directing an ablative needle toward the target. The ablative needle may deliver an ablative agent or other ablative energy such as radiofrequency or cooled radiofrequency. As shown in FIG. 32, an ultrasound imaging guided interstitial ablation needle catheter 460 may comprise an ultrasound imaging transducer and a deployable needle. The imaging transducer 461 may be on a separate catheter (e.g., IVUS catheter) that is advanced through a lumen 462 in the ablation catheter to a distal region of the ablation catheter. The imaging transducer may be positioned in an optional echolucent chamber 463 that contains an fiducial marker for aiming 464 that reflects or absorbs ultrasound waves to create a distinguishable artifact on an ultrasound-based video that represents a relative direction that the deployable needle 465 will be advanced. The deployable needle may have a sharp tip 466 to advance through a vessel wall (e.g., jugular vein 12). As shown, a blunt tipped probe 467 may be advanced out of the sharp tipped needle to pass through target tissue. A blunt tipped probe may pass through tissue such as fat in the target zone and reduce a risk of puncturing an artery (e.g., carotid artery) or injuring a non-target nerve. The probe 467 may be configured to deliver ablation energy. For example, it may comprise an RF electrode 468, a cooled RF electrode, or a lumen to deliver an ablative agent. The probe may contain a sensor 469 such as a temperature sensor (e.g. thermocouple) to monitor or control energy delivery. The deployable sharp needle or probe may have an echogenic coating to improve ultrasound imaging. The catheter may be deflectable or be delivered through a deflectable sheath to assist in positioning or manipulation of a vein to obtain a suitable ablation position. Multiple needles may be deployed for example to create a larger ablation by delivering radiofrequency in a bipolar configuration. A carotid body stimulation agent (e.g., adenosine) may be delivered through injection lumen 470 or a deployable needle or probe to a target zone before and after ablation to confirm if a carotid body has been deactivated.

As shown in FIG. 33 an alternative embodiment of an ultrasound imaging guided needle ablation catheter 471 may comprise imaging transducer(s) 472 integrated with the ablation catheter. In comparison to the embodiment shown in FIG. 32 this embodiment may have a narrower diameter (e.g. in a range of about 8 to 10 FR, about 9 FR) and absence of an IVUS lumen provides more space for a needle lumen 473. An integrated set of imaging transducers 472 may allow a relative direction of needle deployment to be programmed into the ultrasound-based video generation software so the direction of needle deployment can be indicated on an ultrasound-based video. Alternatively the integrated set of imaging transducer(s) may comprise a gap in transducer spacing or a fiducial marker to create a distinguishable image that identifies a relative direction with respect to the needle deployment direction.

Methods of Therapy:

An ablation energy source such as a high frequency current generator for therapeutic ultrasound may be located external to the patient. The generator may include computer controls to automatically or manually adjust frequency and strength of the energy applied to the catheter, timing and period during which energy is applied, and safety limits to the application of energy. It should be understood that embodiments of energy delivery electrodes described herein may be electrically connected to the generator even though the generator is not explicitly shown or described with each embodiment.

An endovascular ultrasonic ablation catheter configured to aim ultrasonic energy at a carotid septum may comprise ultrasound visualization capabilities. The ultrasound visualization may comprise Doppler to image blood flow. A catheter may be rotated within an external carotid artery using Doppler to identify when it is aimed through a carotid septum at an internal carotid artery. An ultrasound ablation may be aimed toward the direction of the internal carotid artery and be deposited in a targeted carotid septum.

An ablated tissue lesion at or near the carotid body may be created by the application of ablation energy from an ablation element in a vicinity of a distal end of the carotid body ablation device. The ablated tissue lesion may disable the carotid body or may suppress the activity of the carotid body or interrupt conduction of afferent nerve signals from a carotid body to sympathetic nervous system. The disabling or suppression of the carotid body reduces the responsiveness of the glomus cells to changes of blood gas composition and effectively reduces activity of afferent carotid body nerves or the chemoreflex gain of the patient.

A method in accordance with a particular embodiment includes ablating at least one of a patient's carotid bodies based at least in part on identifying the patient as having a sympathetically mediated disease such as cardiac, metabolic, or pulmonary disease such as hypertension, insulin resistance, diabetes, pulmonary hypertension, drug resistant hypertension (e.g., refractory hypertension), congestive heart failure (CHF), or dyspnea from heart failure or pulmonary disease causes.

A procedure may include diagnosis, selection based on diagnosis, further screening (e.g., baseline assessment of chemosensitivity), treating a patient based at least in part on diagnosis or further screening via a chemoreceptor (e.g., carotid body) ablation procedure such as one of the embodiments disclosed. Additionally, following ablation a method of therapy may involve conducting a post-ablation assessment to compare with the baseline assessment and making decisions based on the assessment (e.g., adjustment of drug therapy, re-treat in new position or with different parameters, or ablate a second chemoreceptor if only one was previously ablated).

A carotid body ablation procedure may comprise the following steps or a combination thereof: patient sedation, locating a target peripheral chemoreceptor, visualizing a target peripheral chemoreceptor (e.g., carotid body), confirming a target ablation site is or is proximate a peripheral chemoreceptor, confirming a target ablation site is safely distant from vital structures that are preferably protected (e.g., hypoglossal, sympathetic and vagus nerves), providing stimulation (e.g., electrical, mechanical, chemical) to a target site or target peripheral chemoreceptor prior to, during or following an ablation step, monitoring physiological responses to said stimulation, providing temporary nerve block to a target site prior to an ablation step, monitoring physiological responses to said temporary nerve block, anesthetizing a target site, protecting the brain from potential embolism, thermally protecting an arterial or venous wall (e.g., carotid artery, jugular vein) or a medial aspect of an intercarotid septum or vital nerve structures, ablating a target site or peripheral chemoreceptor, monitoring ablation parameters (e.g., temperature, pressure, duration, blood flow in a carotid artery), monitoring physiological responses during ablation and arresting ablation if unsafe or unwanted physiological responses occur before collateral nerve injury becomes permanent, confirming a reduction of chemoreceptor activity (e.g., chemosensitivity, HR, blood pressure, ventilation, sympathetic nerve activity) during or following an ablation step, removing a ablation device, conducting a post-ablation assessment, repeating any steps of the chemoreceptor ablation procedure on another peripheral chemoreceptor in the patient.

Patient screening, as well as post-ablation assessment may include physiological tests or gathering of information, for example, chemoreflex sensitivity, central sympathetic nerve activity, heart rate, heart rate variability, blood pressure, ventilation, production of hormones, peripheral vascular resistance, blood pH, blood $PCO_2$, degree of hyperventilation, peak $VO_2$, $VE/VCO_2$ slope. Directly measured maximum oxygen uptake (more correctly $pVO_2$ in heart failure patients) and index of respiratory efficiency $VE/VCO_2$ slope has been shown to be a reproducible marker of exercise tolerance in heart failure and provide objective and additional information regarding a patient's clinical status and prognosis.

A method of therapy may include electrical stimulation of a target region, using a stimulation electrode, to confirm proximity to a carotid body. For example, a stimulation signal having a 1-10 milliamps (mA) pulse train at about 20 to 40 Hz with a pulse duration of 50 to 500 microseconds (μs) that produces a positive carotid body stimulation effect may indicate that the stimulation electrode is within sufficient proximity to the carotid body or nerves of the carotid body to effectively ablate it. A positive carotid body stimulation effect could be increased blood pressure, heart rate, or ventilation concomitant with application of the stimulation. These variables could be monitored, recorded, or displayed to help assess confirmation of proximity to a carotid body. A catheter-based technique, for example, may have a stimulation electrode proximal to the ablation element used for ablation. Alternatively, the ablation element itself may also be used as a stimulation electrode. Alternatively, an energy delivery element that delivers a form of ablative energy that is not electrical, such as a cryogenic ablation applicator, may be configured to also deliver an electrical stimulation signal as described earlier. Yet another alternative embodiment comprises a stimulation electrode that is distinct from an ablation element. For example, during a surgical procedure a stimulation probe can be touched to a suspected carotid body that is surgically exposed. A positive carotid body stimulation effect could confirm that the suspected structure is a carotid body and ablation can commence. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlates to a given stimulation the computerized generator may provide an indication of a positive confirmation.

Alternatively or in addition a drug known to excite the chemo sensitive cells of the carotid body can be injected directly into the carotid artery or given systemically into patients vein or artery in order to elicit hemodynamic or respiratory response. Examples of drugs that may excite a chemoreceptor include nicotine, atropine, Doxapram, Almitrine, hyperkalemia, Theophylline, adenosine, sulfides, Lobeline, Acetylcholine, ammonium chloride, methylamine, potassium chloride, anabasine, coniine, cytosine, acetaldehyde, acetyl ester and the ethyl ether of i-methylcholine, Succinylcholine, Piperidine, monophenol ester of homo-isomuscarine and acetylsalicylamides, alkaloids of veratrum, sodium citrate, adenosinetriphosphate, dinitrophenol, caffeine, theobromine, ethyl alcohol, ether, chloroform, phenyldiguanide, sparteine, coramine (nikethamide), metrazol (pentylenetetrazol), iodomethylate of dimethylaminomethylenedioxypropane, ethyltrimethylammoniumpropane, trimethylammonium, hydroxytryptamine, papaverine, neostigmine, acidity.

Described methods may include ultrasound activated drug delivery to carotid complex. Drugs can be incorporated into particles capable of ultrasound activation. Intravenous or direct intratumoral injection of such drug compositions comprising microbubbles, nanoparticles, liposomes and biologically active agents encapsulated in polymers undergo a physical change when subjected to ultrasound beam. The compositions include microemulsions which may create microbubbles as cavitation nuclei in the process of injection and enhance intracellular drug delivery in the carotid complex. The administration of the ultrasound beam to a carotid complex perfused with encapsulated drugs may stimulate a release of the therapeutic agent to a selected volume affected by the application of ultrasound, In addition to a release of a therapeutic agent the microbubbles generated in situ during an ultrasound irradiatinirradiation procedure may produce additional guidance to ultrasound imaging.

A method of therapy may further comprise applying electrical or chemical stimulation to the target area or systemically following ablation to confirm a successful ablation. Heart rate, blood pressure or ventilation may be monitored for change or compared to the reaction to stimulation prior to ablation to assess if the targeted carotid body was ablated. Post-ablation stimulation may be done with the same apparatus used to conduct the pre-ablation stimulation. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlated to a given stimulation is reduced following an ablation compared to a physiological response prior to the ablation, the computerized generator may provide an indication ablation efficacy or possible procedural suggestions such as repeating an ablation, adjusting ablation parameters, changing position, ablating another carotid body or chemosensor, or concluding the procedure.

The devices described herein may also be used to temporarily stun or block nerve conduction via electrical neural blockade. A temporary nerve block may be used to confirm position of an ablation element prior to ablation. For example, a temporary nerve block may block nerves associated with a carotid body, which may result in a physiological effect to confirm the position may be effective for ablation. Furthermore, a temporary nerve block may block vital nerves such as vagal, hypoglossal or sympathetic nerves that are preferably avoided, resulting in a physiological effect (e.g., physiological effects may be noted by observing the patient's eyes, tongue, throat or facial muscles or by monitoring patient's heart rate and respiration). This may alert a user that the position is not in a safe location. Likewise absence of a physiological effect indicating a temporary nerve block of such vital nerves in combination with a physiological effect indicating a temporary nerve block of carotid body nerves may indicate that the position is in a safe and effective location for carotid body ablation.

Important nerves may be located in proximity of the target site and may be inadvertently and unintentionally injured. Neural stimulation or blockade can help identify that these nerves are in the ablation zone before the irreversible ablation occurs. These nerves may include the following:

Vagus Nerve Bundle—The vagus is a bundle of nerves that carry separate functions, for example a) branchial motor neurons (efferent special visceral) which are responsible for swallowing and phonation and are distributed to pharyngeal branches, superior and inferior laryngeal nerves; b) visceral motor (efferent general visceral) which are responsible for involuntary muscle and gland control and are distributed to cardiac, pulmonary, esophageal, gastric, celiac plexuses, and muscles, and glands of the digestive tract; c) visceral sensory (afferent general visceral) which are responsible for visceral sensibility and are distributed to cervical, thoracic, abdominal fibers, and carotid and aortic bodies; d) visceral sensory (afferent special visceral) which are responsible for taste and are distributed to epiglottis and taste buds; e) general sensory (afferent general somatic) which are responsible for cutaneous sensibility and are distributed to auricular branch to external ear, meatus, and tympanic membrane. Dysfunction of the vagus may be detected by a) vocal changes caused by nerve damage (damage to the vagus nerve can result in trouble with moving the tongue while speaking, or hoarseness of the voice if the branch leading to the larynx is damaged); b) dysphagia due to nerve damage (the vagus nerve controls many muscles in the palate and tongue which, if damaged, can cause difficulty with swallowing); c) changes in gag reflex (the gag reflex is controlled by the vagus nerve and damage may cause this reflex to be lost, which can increase the risk of choking on saliva or food); d) hearing loss due to nerve damage (hearing loss may result from damage to the branch of the vagus nerve that innervates the concha of the ear): e) cardiovascular problems due to nerve damage (damage to the vagus nerve can cause cardiovascular side effects including irregular heartbeat and arrhythmia); or f) digestive problems due to nerve damage (damage to the vagus nerve may cause problems with contractions of the stomach and intestines, which can lead to constipation).

Superior Laryngeal Nerve—the superior laryngeal nerve is a branch of the vagus nerve bundle. Functionally, the superior laryngeal nerve function can be divided into sensory and motor components. The sensory function provides a variety of afferent signals from the supraglottic larynx. Motor function involves motor supply to the ipsilateral cricothyroid muscle. Contraction of the cricothyroid muscle tilts the cricoid lamina backward at the cricothyroid joint causing lengthening, tensing and adduction of vocal folds causing an increase in the pitch of the voice generated. Dysfunction of the superior laryngeal nerve may change the pitch of the voice and causes an inability to make explosive sounds. A bilateral palsy presents as a tiring and hoarse voice.

Cervical Sympathetic Nerve—The cervical sympathetic nerve provides efferent fibers to the internal carotid nerve, external carotid nerve, and superior cervical cardiac nerve. It provides sympathetic innervation of the head, neck and heart. Organs that are innervated by the sympathetic nerves include eyes, lacrimal gland and salivary glands. Dysfunction of the cervical sympathetic nerve includes Horner's syndrome, which is very identifiable and may include the following reactions: a) partial ptosis (drooping of the upper eyelid from loss of sympathetic innervation to the superior tarsal muscle, also known as Müller's muscle); b) upside-down ptosis (slight elevation of the lower lid); c) anhidrosis (decreased sweating on the affected side of the face); d) miosis (small pupils, for example small relative to what would be expected by the amount of light the pupil receives or constriction of the pupil to a diameter of less than two millimeters, or asymmetric, one-sided constriction of pupils); e) enophthalmos (an impression that an eye is sunken in); f) loss of ciliospinal reflex (the ciliospinal reflex, or pupillary-skin reflex, consists of dilation of the ipsilateral pupil in response to pain applied to the neck, face, and upper trunk. If the right side of the neck is subjected to a painful stimulus, the right pupil dilates about 1-2 mm from baseline. This reflex is absent in Horner's syndrome and lesions involving the cervical sympathetic fibers.)

Overview:

Ablation of a target ablation site (e.g., peripheral chemoreceptor, carotid body) via directed energy in patients having sympathetically mediated disease and augmented chemoreflex (e.g., high afferent nerve signaling from a carotid body to the central nervous system as in some cases indicated by high peripheral chemosensitivity) has been conceived to reduce peripheral chemosensitivity and reduce afferent signaling from peripheral chemoreceptors to the central nervous system. Additionally, ablation of a target ablation site (e.g., peripheral chemoreceptor, carotid body) via a transvenous endovascular approach in patients having sympathetically mediated disease and augmented chemoreflex (e.g., high afferent nerve signaling from a carotid body to the central nervous system as in some cases indicated by high peripheral chemosensitivity) has been conceived to reduce peripheral chemosensitivity and reduce afferent signaling from peripheral chemoreceptors to the central nervous system. The expected reduction of chemoreflex activity and sensitivity to hypoxia and other stimuli such as blood flow, blood $CO_2$, glucose concentration or blood pH can directly reduce afferent signals from chemoreceptors and produce at least one beneficial effect such as the reduction of central sympathetic activation, reduction of the sensation of breathlessness (dyspnea), vasodilation, increase of exercise capacity, reduction of blood pressure, reduction of sodium and water retention, redistribution of blood volume to skeletal muscle, reduction of insulin resistance, reduction of hyperventilation, reduction of tachypnea, reduction of hypocapnia, increase of baroreflex and baro sensitivity of baroreceptors, increase of vagal tone, or improve symptoms of a sympathetically mediated disease and may ultimately slow down the disease progression and extend life. It is understood that a sympathetically mediated disease that may be treated with carotid body ablation may comprise elevated sympathetic tone, an elevated sympathetic/parasympathetic activity ratio, autonomic imbalance primarily attributable to central sympathetic tone being abnormally or undesirably high, or heightened sympathetic tone at least partially attributable to afferent excitation traceable to hypersensitivity or hyperactivity of a peripheral chemoreceptor (e.g., carotid body). In some important clinical cases where baseline hypocapnia or tachypnea is present, reduction of hyperventilation and breathing rate may be expected. It is understood that hyperventilation in the context herein means respiration in excess of metabolic needs on the individual that generally leads to slight but significant hypocapnea (blood $CO_2$ partial pressure below normal of approximately 40 mmHg, for example in the range of 33 to 38 mmHg).

Patients having CHF or hypertension concurrent with heightened peripheral chemoreflex activity and sensitivity often react as if their system was hypercapnic even if it is not. The reaction is often to hyperventilate, a maladaptive attempt to rid the system of $CO_2$, thus overcompensating and creating a hypocapnic and alkalotic system. Some researchers attribute this hypersensitivity/hyperactivity of the carotid body to the direct effect of catecholamines, hormones circulating in excessive quantities in the blood stream of CHF patients. The procedure may be particularly useful to treat such patients who are hypocapnic and possibly alkalotic resulting from high tonic output from carotid bodies. Such patients are particularly predisposed to periodic breathing and central apnea hypopnea type events that cause arousal, disrupt sleep, cause intermittent hypoxia and are by themselves detrimental and difficult to treat.

It is appreciated that periodic breathing of Cheyne Stokes pattern occurs in patients during sleep, exercise and even at rest as a combination of central hypersensitivity to $CO_2$, peripheral chemosensitivity to $O_2$ and $CO_2$ and prolonged circulatory delay. All these parameters are often present in CHF patients that are at high risk of death. Thus, patients with hypocapnea, CHF, high chemosensitivity and prolonged circulatory delay, and specifically ones that exhibit periodic breathing at rest or during exercise or induced by hypoxia are likely beneficiaries of the proposed therapy.

Hyperventilation is defined as breathing in excess of a person's metabolic need at a given time and level of activity. Hyperventilation is more specifically defined as minute ventilation in excess of that needed to remove CO2 from blood in order to maintain blood $CO_2$ in the normal range (e.g., around 40 mmHg partial pressure). For example, patients with arterial blood $PCO_2$ in the range of 32-37 mmHg can be considered hypocapnic and in hyperventilation.

For the purpose of this disclosure hyperventilation is equivalent to abnormally low levels of carbon dioxide in the blood (e.g., hypocapnia, hypocapnea, or hypocarbia) caused by overbreathing. Hyperventilation is the opposite of hypoventilation (e.g., underventilation) that often occurs in patients with lung disease and results in high levels of carbon dioxide in the blood (e.g., hypercapnia or hypercarbia).

A low partial pressure of carbon dioxide in the blood causes alkalosis, because CO2 is acidic in solution and reduced CO2 makes blood pH more basic, leading to lowered plasma calcium ions and nerve and muscle excitability. This condition is undesirable in cardiac patients since it can increase probability of cardiac arrhythmias.

Alkalemia may be defined as abnormal alkalinity, or increased pH of the blood. Respiratory alkalosis is a state due to excess loss of carbon dioxide from the body, usually as a result of hyperventilation. Compensated alkalosis is a form in which compensatory mechanisms have returned the pH toward normal. For example, compensation can be achieved by increased excretion of bicarbonate by the kidneys.

Compensated alkalosis at rest can become uncompensated during exercise or as a result of other changes of metabolic balance. Thus the invented method is applicable to treatment of both uncompensated and compensated respiratory alkalosis.

Tachypnea means rapid breathing. For the purpose of this disclosure a breathing rate of about 6 to 16 breaths per minute at rest is considered normal but there is a known benefit to lower rate of breathing in cardiac patients. Reduction of tachypnea can be expected to reduce respiratory dead space, increase breathing efficiency, and increase parasympathetic tone.

Therapy Example: Role of Chemoreflex and Central Sympathetic Nerve Activity in CHF Chronic elevation in sympathetic nerve activity (SNA) is associated with the development and progression of certain types of hypertension and contributes to the progression of congestive heart failure (CHF). It is also known that sympathetic excitatory cardiac, somatic, and central/peripheral chemoreceptor reflexes are abnormally enhanced in CHF and hypertension (Ponikowski, 2011 and Giannoni, 2008 and 2009).

Arterial chemoreceptors serve an important regulatory role in the control of alveolar ventilation. They also exert a powerful influence on cardiovascular function.

Delivery of Oxygen ($O_2$) and removal of Carbon Dioxide ($CO_2$) in the human body is regulated by two control systems, behavioral control and metabolic control. The metabolic ventilatory control system drives our breathing at rest and ensures optimal cellular homeostasis with respect to pH, partial pressure of carbon dioxide ($PCO_2$), and partial pressure of oxygen ($PO_2$). Metabolic control uses two sets of chemoreceptors that provide a fine-tuning function: the central chemoreceptors located in the ventral medulla of the brain and the peripheral chemoreceptors such as the aortic chemoreceptors and the carotid body chemoreceptors. The carotid body, a small, ovoid-shaped (often described as a grain of rice), and highly vascularized organ is situated in or near the carotid bifurcation, where the common carotid artery branches in to an internal carotid artery (IC) and external carotid artery (EC). The central chemoreceptors are sensitive to hypercapnia (high $PCO_2$), and the peripheral chemoreceptors are sensitive to hypercapnia and hypoxia (low blood $PO_2$). Under normal conditions activation of the sensors by their respective stimuli results in quick ventilatory responses aimed at the restoration of cellular homeostasis.

As early as 1868, Pflüger recognized that hypoxia stimulated ventilation, which spurred a search for the location of oxygen-sensitive receptors both within the brain and at various sites in the peripheral circulation. When Corneille Heymans and his colleagues observed that ventilation increased when the oxygen content of the blood flowing through the bifurcation of the common carotid artery was reduced (winning him the Nobel Prize in 1938), the search for the oxygen chemosensor responsible for the ventilatory response to hypoxia was largely considered accomplished.

The persistence of stimulatory effects of hypoxia in the absence (after surgical removal) of the carotid chemoreceptors (e.g., the carotid bodies) led other investigators, among them Julius Comroe, to ascribe hypoxic chemosensitivity to other sites, including both peripheral sites (e.g., aortic bodies) and central brain sites (e.g., hypothalamus, pons and rostral ventrolateral medulla). The aortic chemoreceptor, located in the aortic body, may also be an important chemoreceptor in humans with significant influence on vascular tone and cardiac function.

Carotid Body Chemoreflex:

The carotid body is a small cluster of chemoreceptors (also known as glomus cells) and supporting cells located near, and in most cases directly at, the medial side of the bifurcation (fork) of the carotid artery, which runs along both sides of the throat.

These organs act as sensors detecting different chemical stimuli from arterial blood and triggering an action potential in the afferent fibers that communicate this information to the Central Nervous System (CNS). In response, the CNS activates reflexes that control heart rate (HR), renal function and peripheral blood circulation to maintain the desired homeostasis of blood gases, $O_2$ and $CO_2$, and blood pH. This closed loop control function that involves blood gas chemoreceptors is known as the carotid body chemoreflex (CBC). The carotid body chemoreflex is integrated in the CNS with the carotid sinus baroreflex (CSB) that maintains arterial blood pressure. In a healthy organism these two reflexes maintain blood pressure and blood gases within a narrow physiologic range. Chemosensors and barosensors in the aortic arch contribute redundancy and fine-tuning function to the closed loop chemoreflex and baroreflex. In addition to sensing blood gasses, the carotid body is now understood to be sensitive to blood flow and velocity, blood Ph and glucose concentration. Thus it is understood that in conditions such as hypertension, CHF, insulin resistance, diabetes and other metabolic derangements afferent signaling of carotid body nerves may be elevated. Carotid body hyperactivity may be present even in the absence of detectable hypersensitivity to hypoxia and hypercapnia that are traditionally used to index carotid body function. The purpose of the proposed therapy is therefore to remove or reduce afferent neural signals from a carotid body and reduce carotid body contribution to central sympathetic tone.

The carotid sinus baroreflex is accomplished by negative feedback systems incorporating pressure sensors (e.g., baroreceptors) that sense the arterial pressure. Baroreceptors also exist in other places, such as the aorta and coronary arteries. Important arterial baroreceptors are located in the carotid sinus, a slight dilatation of the internal carotid artery 201 at its origin from the common carotid. The carotid sinus baroreceptors are close to but anatomically separate from the carotid body. Baroreceptors respond to stretching of the arterial wall and communicate blood pressure information to CNS. Baroreceptors are distributed in the arterial walls of the carotid sinus while the chemoreceptors (glomus cells) are clustered inside the carotid body. This makes the selective reduction of chemoreflex described in this application possible while substantially sparing the baroreflex.

The carotid body exhibits great sensitivity to hypoxia (low threshold and high gain). In chronic Congestive Heart Failure (CHF), the sympathetic nervous system activation that is directed to attenuate systemic hypoperfusion at the initial phases of CHF may ultimately exacerbate the progression of cardiac dysfunction that subsequently increases the extra-cardiac abnormalities, a positive feedback cycle of progressive deterioration, a vicious cycle with ominous consequences. It was thought that much of the increase in the sympathetic nerve activity (SNA) in CHF was based on an increase of sympathetic flow at a level of the CNS and on the depression of arterial baroreflex function. In the past several years, it has been demonstrated that an increase in the activity and sensitivity of peripheral chemoreceptors (heightened chemoreflex function) also plays an important role in the enhanced SNA that occurs in CHF.

Role of Altered Chemoreflex in CHF:

As often happens in chronic disease states, chemoreflexes that are dedicated under normal conditions to maintaining homeostasis and correcting hypoxia contribute to increase the sympathetic tone in patients with CHF, even under normoxic conditions. The understanding of how abnormally enhanced sensitivity of the peripheral chemosensors, particularly the carotid body, contributes to the tonic elevation in SNA in patients with CHF has come from several studies in animals. According to one theory, the local angiotensin receptor system plays a fundamental role in the enhanced carotid body chemoreceptor sensitivity in CHF. In addition, evidence in both CHF patients and animal models of CHF has clearly established that the carotid body chemoreflex is often hypersensitive in CHF patients and contributes to the tonic elevation in sympathetic function. This derangement derives from altered function at the level of both the afferent and central pathways of the reflex arc. The mechanisms responsible for elevated afferent activity from the carotid body in CHF are not yet fully understood.

Regardless of the exact mechanism behind the carotid body hypersensitivity, the chronic sympathetic activation driven from the carotid body and other autonomic pathways leads to further deterioration of cardiac function in a positive feedback cycle. As CHF ensues, the increasing severity of cardiac dysfunction leads to progressive escalation of these alterations in carotid body chemoreflex function to further elevate sympathetic activity and cardiac deterioration. The trigger or causative factors that occur in the development of CHF that sets this cascade of events in motion and the time course over which they occur remain obscure. Ultimately, however, causative factors are tied to the cardiac pump failure and reduced cardiac output. According to one theory, within the carotid body, a progressive and chronic reduction in blood flow may be the key to initiating the maladaptive changes that occur in carotid body chemoreflex function in CHF.

There is sufficient evidence that there is increased peripheral and central chemoreflex sensitivity in heart failure, which is likely to be correlated with the severity of the disease. There is also some evidence that the central chemoreflex is modulated by the peripheral chemoreflex. According to current theories, the carotid body is the predominant contributor to the peripheral chemoreflex in humans; the aortic body having a minor contribution.

Although the mechanisms responsible for altered central chemoreflex sensitivity remain obscure, the enhanced peripheral chemoreflex sensitivity can be linked to a depression of nitric oxide production in the carotid body affecting afferent sensitivity, and an elevation of central angiotensin II affecting central integration of chemoreceptor input. The enhanced chemoreflex may be responsible, in part, for the enhanced ventilatory response to exercise, dyspnea, Cheyne-Stokes breathing, and sympathetic activation observed in chronic heart failure patients. The enhanced chemoreflex may be also responsible for hyperventilation and tachypnea (e.g., fast breathing) at rest and exercise, periodic breathing during exercise, rest and sleep, hypocapnia, vasoconstriction, reduced peripheral organ perfusion and hypertension.

Dyspnea:

Shortness of breath, or dyspnea, is a feeling of difficult or labored breathing that is out of proportion to the patient's level of physical activity. It is a symptom of a variety of different diseases or disorders and may be either acute or chronic. Dyspnea is the most common complaint of patients with cardiopulmonary diseases.

Dyspnea is believed to result from complex interactions between neural signaling, the mechanics of breathing, and the related response of the central nervous system. A specific area has been identified in the mid-brain that may influence the perception of breathing difficulties.

The experience of dyspnea depends on its severity and underlying causes. The feeling itself results from a combination of impulses relayed to the brain from nerve endings in the lungs, rib cage, chest muscles, or diaphragm, combined with the perception and interpretation of the sensation by the patient. In some cases, the patient's sensation of breathlessness is intensified by anxiety about its cause. Patients describe dyspnea variously as unpleasant shortness of breath, a feeling of increased effort or tiredness in moving the chest muscles, a panicky feeling of being smothered, or a sense of tightness or cramping in the chest wall.

The four generally accepted categories of dyspnea are based on its causes: cardiac, pulmonary, mixed cardiac or pulmonary, and non-cardiac or non-pulmonary. The most common heart and lung diseases that produce dyspnea are asthma, pneumonia, COPD, and myocardial ischemia or heart attack (myocardial infarction). Foreign body inhalation, toxic damage to the airway, pulmonary embolism, congestive heart failure (CHF), anxiety with hyperventilation (panic disorder), anemia, and physical deconditioning because of sedentary lifestyle or obesity can produce dyspnea. In most cases, dyspnea occurs with exacerbation of the underlying disease. Dyspnea also can result from weakness or injury to the chest wall or chest muscles, decreased lung elasticity, obstruction of the airway, increased oxygen demand, or poor pumping action of the heart that results in increased pressure and fluid in the lungs, such as in CHF.

Acute dyspnea with sudden onset is a frequent cause of emergency room visits. Most cases of acute dyspnea involve pulmonary (lung and breathing) disorders, cardiovascular disease, or chest trauma. Sudden onset of dyspnea (acute dyspnea) is most typically associated with narrowing of the airways or airflow obstruction (bronchospasm), blockage of one of the arteries of the lung (pulmonary embolism), acute heart failure or myocardial infarction, pneumonia, or panic disorder.

Chronic dyspnea is different. Long-standing dyspnea (chronic dyspnea) is most often a manifestation of chronic or progressive diseases of the lung or heart, such as COPD, which includes chronic bronchitis and emphysema. The treatment of chronic dyspnea depends on the underlying disorder. Asthma can often be managed with a combination of medications to reduce airway spasms and removal of allergens from the patient's environment. COPD requires medication, lifestyle changes, and long-term physical rehabilitation. Anxiety disorders are usually treated with a combination of medication and psychotherapy.

Although the exact mechanism of dyspnea in different disease states is debated, there is no doubt that the CBC plays some role in most manifestations of this symptom. Dyspnea seems to occur most commonly when afferent input from peripheral receptors is enhanced or when cortical perception of respiratory work is excessive.

Surgical Removal of the Glomus and Resection of Carotid Body Nerves:

A surgical treatment for asthma, removal of the carotid body or glomus (glomectomy), was described by Japanese surgeon Komei Nakayama in 1940s. According to Nakayama in his study of 4,000 patients with asthma, approximately 80% were cured or improved six months after surgery and 58% allegedly maintained good results after five years. Komei Nakayama performed most of his surgeries while at the Chiba University during World War II. Later in the 1950s, a U.S. surgeon, Dr. Overholt, performed the Nakayama operation on 160 U.S. patients. He felt it necessary to remove both carotid bodies in only three cases. He reported that some patients feel relief the instant when the carotid body is removed, or even earlier, when it is inactivated by an injection of procaine (Novocain).

Overholt, in his paper Glomectomy for Asthma published in Chest in 1961, described surgical glomectomy the following way: "A two-inch incision is placed in a crease line in the neck, one-third of the distance between the angle of the mandible and clavicle. The platysma muscle is divided and the sternocleidomastoid retracted laterally. The dissection is carried down to the carotid sheath exposing the bifurcation. The superior thyroid artery is ligated and divided near its take-off in order to facilitate rotation of the carotid bulb and expose the medial aspect of the bifurcation. The carotid body is about the size of a grain of rice and is hidden within the adventitia of the vessel and is of the same color. The perivascular adventitia is removed from one centimeter above to one centimeter below the bifurcation. This severs connections of the nerve plexus, which surrounds the carotid body. The dissection of the adventitia is necessary in order to locate and identify the body. It is usually located exactly at the point of bifurcation on its medial aspect. Rarely, it may be found either in the center of the crotch or on the lateral wall. The small artery entering the carotid body is clamped, divided, and ligated. The upper stalk of tissue above the carotid body is then clamped, divided, and ligated."

In January 1965, the New England Journal of Medicine published a report of 15 cases in which there had been unilateral removal of the cervical glomus (carotid body) for the treatment of bronchial asthma, with no objective beneficial effect. This effectively stopped the practice of glomectomy to treat asthma in the U.S.

Winter developed a technique for separating nerves that contribute to the carotid sinus nerves into two bundles, carotid sinus (baroreflex) and carotid body (chemoreflex), and selectively cutting out the latter. The Winter technique is based on his discovery that carotid sinus (baroreflex) nerves are predominantly on the lateral side of the carotid bifurcation and carotid body (chemoreflex) nerves are predominantly on the medial side.

Neuromodulation of the Carotid Body Chemoreflex:

Hlavka in U.S. Patent Application Publication 2010/0070004 filed Aug. 7, 2009, describes implanting an electrical stimulator to apply electrical signals, which block or inhibit chemoreceptor signals in a patient suffering dyspnea. Hlavka teaches that "some patients may benefit from the ability to reactivate or modulate chemoreceptor functioning." Hlavka focuses on neuromodulation of the chemoreflex by selectively blocking conduction of nerves that connect the carotid body to the CNS. Hlavka describes a traditional approach of neuromodulation with an implantable electric pulse generator that does not modify or alter tissue of the carotid body or chemoreceptors.

The central chemoreceptors are located in the brain and are difficult to access. The peripheral chemoreflex is modulated primarily by carotid bodies that are more accessible. Previous clinical practice had very limited clinical success with the surgical removal of carotid bodies to treat asthma in 1940s and 1960s.

What is claimed is:

1. An ultrasound ablation catheter, comprising:
a distal assembly comprising an ultrasound ablation transducer, an echolucent shell, and an ablation direction fiducial marker, the echolucent shell at least partially defining a distal chamber, the ultrasound ablation transducer disposed within the distal chamber, the distal assembly adapted to house therein an ultrasound imaging transducer,
the ablation direction fiducial marker positioned relative to the ultrasound ablation transducer and adapted to, when an ultrasound imaging transducer is positioned and activated within the distal assembly, create an aiming artifact on an image created by the ultrasound imaging transducer, the aiming artifact adapted to be used to indicate a direction of ablation; and
an elongate shaft extending proximally from the distal assembly.

2. The catheter of claim 1 wherein the ablation direction fiducial marker is axially aligned with the ultrasound imaging catheter when the ultrasound image transducer is in an active position in the distal assembly.

3. The catheter of claim 1 wherein the ablation direction fiducial marker is disposed relative to the ultrasound ablation transducer such that the direction of the ablation energy emitted from the ultrasound ablation transducer can be determined based on the location of the indicator on the image.

4. The catheter of claim 3 wherein the ablation direction fiducial marker is secured to the echolucent shell.

5. The catheter of claim 4 wherein the echolucent shell comprises first and second membranes, the ablation direction fiducial marker secured between the first and second membranes.

6. The catheter of claim 5 wherein the ablation direction fiducial marker has a curved configuration.

7. The catheter of claim 1 wherein the ablation direction fiducial marker has a curved configuration.

8. The catheter of claim 1 wherein the ablation direction fiducial marker has a configuration that is a partial tubular member.

9. The catheter of claim 1 wherein the ablation direction fiducial marker is an extension of a support member disposed proximal to the ablation direction fiducial marker.

10. The catheter of claim 1 wherein the ablation direction fiducial marker is an echo-opaque material.

11. The catheter of claim 10 wherein the ablation direction fiducial marker comprises stainless steel.

12. The catheter of claim 1 wherein the ultrasound ablation catheter is configured to be inserted through a jugular vein of a patient and wherein the ultrasound ablation transducer is configured to be placed in proximity to a target ablation site including a carotid body.

13. The catheter of claim 1 wherein the distal assembly further comprises a lumen therein configured to receive therethrough an ultrasound imaging catheter.

14. The catheter of claim 1 wherein the ultrasound ablation transducer is a flat transducer with an axial axis that is parallel to the longitudinal axis of the elongate shaft in a straight configuration.

15. The catheter of claim 14 wherein the flat transducer is disposed in an outer radial portion of the distal region.

16. The catheter of claim 1 wherein the echolucent shell has a first thickness at a first axial location of the ablation ultrasound transducer, and a second thickness greater than the first thickness at a second axial location distal to the ablation ultrasound transducer.

17. The catheter of claim 16 wherein the echolucent shell comprises at least first and second membrane sections that are affixed together in the second axial location.

18. The catheter of claim 1 further comprising a fluid lumen, the fluid lumen in fluid communication with the ultrasound ablation transducer, the fluid lumen also comprising an electrical connector in electrical communication with the ablation ultrasound transducer.

19. The catheter of claim 1 further comprising a manifold secured to and extending distally from at least a portion of the elongate shaft, the ablation ultrasound transducer mounted to the manifold.

20. The catheter of claim 19 further comprising a wafer secured between the ablation ultrasound transducer and the manifold.

21. The catheter of claim 19 wherein the manifold further comprises a lumen adapted to receive an ultrasound imaging catheter therein.

22. The catheter of claim 19 wherein the manifold comprises at least one fluid exit lumen in communication with a proximal region of the catheter.

23. The catheter of claim 19 wherein the manifold comprises a recess defined by side edges and a back plate, the recess adapted to receive therein the ultrasound ablation transducer, wherein the ablation transducer is secured within the recess such that the side edges extend radially outward relative to the ablation transducer to allow the free flow of cooling fluid over the ablation transducer.

24. The catheter of claim 23 wherein the manifold is configured to induce turbulent flow of cooling fluid over the ablation transducer.

* * * * *